(12) United States Patent
Imamura et al.

(10) Patent No.: US 7,005,415 B1
(45) Date of Patent: Feb. 28, 2006

(54) HEPARIN-BINDING PROTEINS MODIFIED WITH SUGAR CHAINS, METHOD OF PRODUCING THE SAME AND PHARMACEUTICAL COMPOSITIONS CONTAINING THE SAME

(75) Inventors: Toru Imamura, Tokyo (JP); Masahiro Asada, Ibaraki (JP); Syuichi Oka, Ibaraki (JP); Masashi Suzuki, Ibaraki (JP); Atsuko Yoneda, Ibaraki (JP); Keiko Ota, Ibaraki (JP); Yuko Oda, Ibaraki (JP); Kazuko Miyakawa, Ibaraki (JP); Noriko Orikasa, Ibaraki (JP); Chie Asada, Ibaraki (JP); Tetsuhito Kojima, Aichi (JP)

(73) Assignee: Director-General Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/121,017

(22) Filed: Jul. 22, 1998

(30) Foreign Application Priority Data

Nov. 10, 1997 (JP) .................................. 9-307721

(51) Int. Cl.
*A61K 38/16* (2006.01)
*A61K 38/18* (2006.01)
*C07K 14/435* (2006.01)
*C07K 14/475* (2006.01)

(52) U.S. Cl. ..................... 514/8; 530/395; 530/396; 530/399; 530/402; 530/404; 530/411

(58) Field of Classification Search ................... 514/8; 530/395, 396, 399, 402, 404, 411, 408
See application file for complete search history.

(56) References Cited

U.S. PATENT DOCUMENTS

| | | | |
|---|---|---|---|
| 4,280,953 A | | 7/1981 | Guillemin et al. |
| 4,478,746 A | | 10/1984 | Kim et al. |
| 5,360,896 A | * | 11/1994 | Senoo et al. ............. 530/399 |
| 5,486,599 A | * | 1/1996 | Saunders et al. ......... 530/395 |

FOREIGN PATENT DOCUMENTS

| | | |
|---|---|---|
| JP | 2227075 | 9/1990 |
| WO | 8801647 | 3/1988 |
| WO | 9116335 | 10/1991 |

OTHER PUBLICATIONS

Jaye et al., Science, vol. 233, pp. 541-545 (Aug. 1986).
Imamura, et al., Science, vol. 249, pp. 1567-1570 (Sep. 1990).

\* cited by examiner

Primary Examiner—David Saunders
(74) Attorney, Agent, or Firm—Davidson, Davidson & Kappel, LLC

(57) ABSTRACT

A heparin-binding protein functionalized by covalently bonding thereto a sugar chain, a method for producing the protein and a pharmaceutical composition containing the protein as an active ingredient, as well as a method for functionalizing a natural protein having no sugar chain by covalently bonding thereto a sugar chain.

5 Claims, 9 Drawing Sheets

1) High Mannose Type

2) Complex Type

3) Hybrid Type

A) SDS-Denatured Electrophoregram of S/FGF-1a-II Protein

B) SDS-Denatured Electrophoregrams of N-FGF-1a-IV and O-FGF-1a Proteins

Lane a: FGF-1a produced in *E. coli*
Lane b: N-FGF-6/1a-II treated with peptide N-glycosidase F to remove N-linked sugar chains
Lane c: N-FGF-6/1a-II
Lane d: O-FGF-6/1a

- ■ — E. coli-Derived FGF-1a/with heparin
- □ — E. coli-Derived FGF-1a/without heparin
- ● — N-FGF-6/1a-IV/with heparin
- ○ — N-FGF-6/1a-IV/without heparin

HEPARIN-BINDING PROTEINS MODIFIED WITH SUGAR CHAINS, METHOD OF PRODUCING THE SAME AND PHARMACEUTICAL COMPOSITIONS CONTAINING THE SAME

BACKGROUND OF THE INVENTION

The present invention relates to a heparin-binding protein functionalized by covalently bonding thereto sugar chain(s), a method for producing the protein and a pharmaceutical composition containing the protein.

It has been known that heparin-binding proteins, among all, those proteins classified into the fibroblast growth factor (hereinafter, referred to as "FGF") family and fibroblast growth factor homologous factors strongly bind to heparin and heparan sulfate (sulfated polysaccharides) by a non-covalent bond. It has been also known that when a heparin-binding protein such as fibroblast growth factor is mixed with a sulfated polysaccharide such as heparin, the biological activity and physical properties of the heparin-binding protein are altered to change its function; sometimes, such a heparin-binding protein may acquire higher function. However, even if a sulfated polysaccharide was mixed with, the expected functionalization of the protein has been limited. Besides, when such a mixture is used as a pharmaceutical composition, unfavorable physiological activity attributable to a free sulfated polysaccharide has caused a problem. To date, there has been reported no protein in which a heparin-binding protein is joined with sulfated polysaccharide(s) by a covalent bond for the purpose of functionalization of the heparin-binding protein.

In addition, it has never been known to date that artificial addition of asparagine-linked sugar chain(s) (hereinafter, referred to as "N-linked sugar chain(s)") or serine/threonine-linked sugar chain(s) (hereinafter, referred to as an "O-linked sugar chain(s)") to a heparin-binding protein, particularly a protein of the FGF family or a fibroblast growth factor homologous factor, by covalent bond(s) can functionalize the protein. Furthermore, the general effect which N-linked sugar chain(s) or O-linked sugar chain(s) could give has not been known. Exceptionally, with respect to FGF-6, the role of the N-linked sugar chain(s) it naturally has was suggested in an in vitro translation system, but has not been proved directly. To date, there has been reported no example of joining a heparin-binding protein with N-linked or O-linked sugar chain(s) by covalent bond(s) for the purpose of functionalizing the heparin-binding protein.

It is an object of the present invention to improve the function of heparin-binding proteins. It is another object of the invention to establish a heparin-binding protein to which sugar chain(s) are covalently bonded and a method for producing the protein. It is still another object of the invention to provide a pharmaceutical composition containing the above protein.

SUMMARY OF THE INVENTION

The present inventors have made intensive and extensive researches toward the solution of the above problems. As a result, the inventors have noted the fact that sulfated polysaccharide(s), glycosaminoglycan(s), N-linked sugar chain(s) and O-linked sugar chain(s) are individually synthesized in living animal bodies as sugar chain(s) of a glycoprotein. Then, the inventors have found that it is possible to produce a heparin-binding protein having in its molecule sulfated polysaccharide(s), glycosaminoglycan(s), N-linked sugar chain(s) or O-linked sugar chain(s) covalently bonded thereto by ensuring that a cDNA coding for a peptide to which any of the above sugar chains can be added is ligated to a cDNA coding for the heparin-binding protein, and by then allowing an animal cell to produce the gene product of the ligated cDNA. Furthermore, the inventors have confirmed that the function of the resultant sugar chain(s)-added heparin-binding protein is improved. Thus, the present invention has been achieved based on these findings.

The present invention provides a heparin-binding protein functionalized by covalently bonding thereto sugar chain(s). The sugar chain(s) may be selected from the group consisting of sulfated polysaccharide(s), glycosaminoglycan(s), N-linked sugar chain(s), O-linked sugar chain(s) and a combination thereof. The heparin-binding protein may be a factor belonging to the FGF family or its allied factor. The heparin-binding protein may be covalently bonded to the sugar chain(s) through a peptide to which the sugar chain(s) can be added. For example, the heparin-binding protein to which the sugar chain(s) are to be covalently bonded may be the following (a) or (b):

(a) a protein consisting of the amino acid sequence of SEQ ID NO: 1, 3, 5, 17, 19, 21, 23, 25, 27 or 29;

(b) a protein which consists of the amino acid sequence of SEQ ID NO:1, 3, 5, 17, 19, 21, 23, 25, 27 or 29 having deletion, substitution, addition or modification of one or several amino acids, which has FGF activity and to which the sugar chain can be added.

In the heparin-binding protein of the invention, the sugar chain(s) may be bonded to the heparin-binding protein at a site forming a turn in the secondary structure or a site near one of the ends, or a site which would not change the tertiary structure of the protein greatly by addition of the sugar chain(s).

The present invention also provides a method for producing a heparin-binding protein functionalized by covalently bonding thereto sugar chain(s), comprising the following steps:

(a) a step in which a cDNA coding for a peptide to which sugar chain(s) can be added is ligated to a cDNA coding for a heparin-binding protein;

(b) a step of incorporating the resultant ligated cDNA into an expression vector;

(c) a step of introducing the expression vector into a host cell having sugar chain(s) addition pathway; and (d) a step of expressing in the host cell a heparin-binding protein to which sugar chain(s) are covalently bonded through the peptide to which the sugar chain(s) can be added.

When the sugar chain(s) are sulfated polysaccharide(s) or glycosaminoglycan(s), the peptide to which the sugar chain(s) can be added may be a proteoglycan core protein or a part thereof. When the sugar chain(s) are N-linked sugar chain(s), the peptide to which the sugar chain(s) can be added may be a peptide comprising N-linked sugar chain(s)-added amino acid sequence. When the sugar chain(s) are O-linked sugar chain(s), the peptide to which the sugar chain(s) can be added may be a peptide comprising O-linked sugar chain(s)-added amino acid sequence. The present invention also provides a method for producing a heparin-binding protein functionalized by covalently bonding thereto sugar chain(s), comprising a step of allowing the sugar chain(s) to bind to the heparin-binding protein by a chemical binding method. The sugar chain(s) may be selected from the group consisting of sulfated polysaccharide(s), glycosaminoglycan(s), N-linked sugar chain(s), O-linked sugar chain(s) and a combination thereof, and the heparin-binding protein may be a factor belonging to the FGF family or its allied factor. The present invention further provides a pharmaceutical composition containing, as an active ingredient, a heparin-binding protein functionalized by covalently bonding thereto sugar chain(s). The present invention also provides a method for functionalizing a natural protein having no sugar chain(s) by covalently bonding thereto sugar chain(s).

The novel sugar chain(s)-added heparin-binding protein of the invention is excellent in stabilities such as thermostability, acid resistance, alkali resistance and resistance to proteolytic enzymes. Thus, by using the sugar chain(s)-added heparin-binding protein of the invention in a pharmaceutical product, it is possible to design such a pharmaceutical product that is excellent in in vivo stabilities, in particular acid resistance and alkali resistance, and applicable to an oral medicine.

BRIEF DESCRIPTION OF THE DRAWINGS

FIG. 5B shows the DNA synthesis promoting activity on HUVEC of *E. coli*-derived FGF-1a.

FIG. 6B shows the thermostability, acid resistance and alkali resistance of *E. coli*-derived FGF-1a.

FIG. 7 shows the resistance to trypsin of S/FGF-1a-II and *E. coli*-derived FGF-1a.

FIG. 8 shows the DNA synthesis promoting activity on HUVEC of N-FGF-6/1a-IV and *E. coli*-derived FGF-1a.

DESCRIPTION OF PREFERRED EMBODIMENTS

Figure 1:
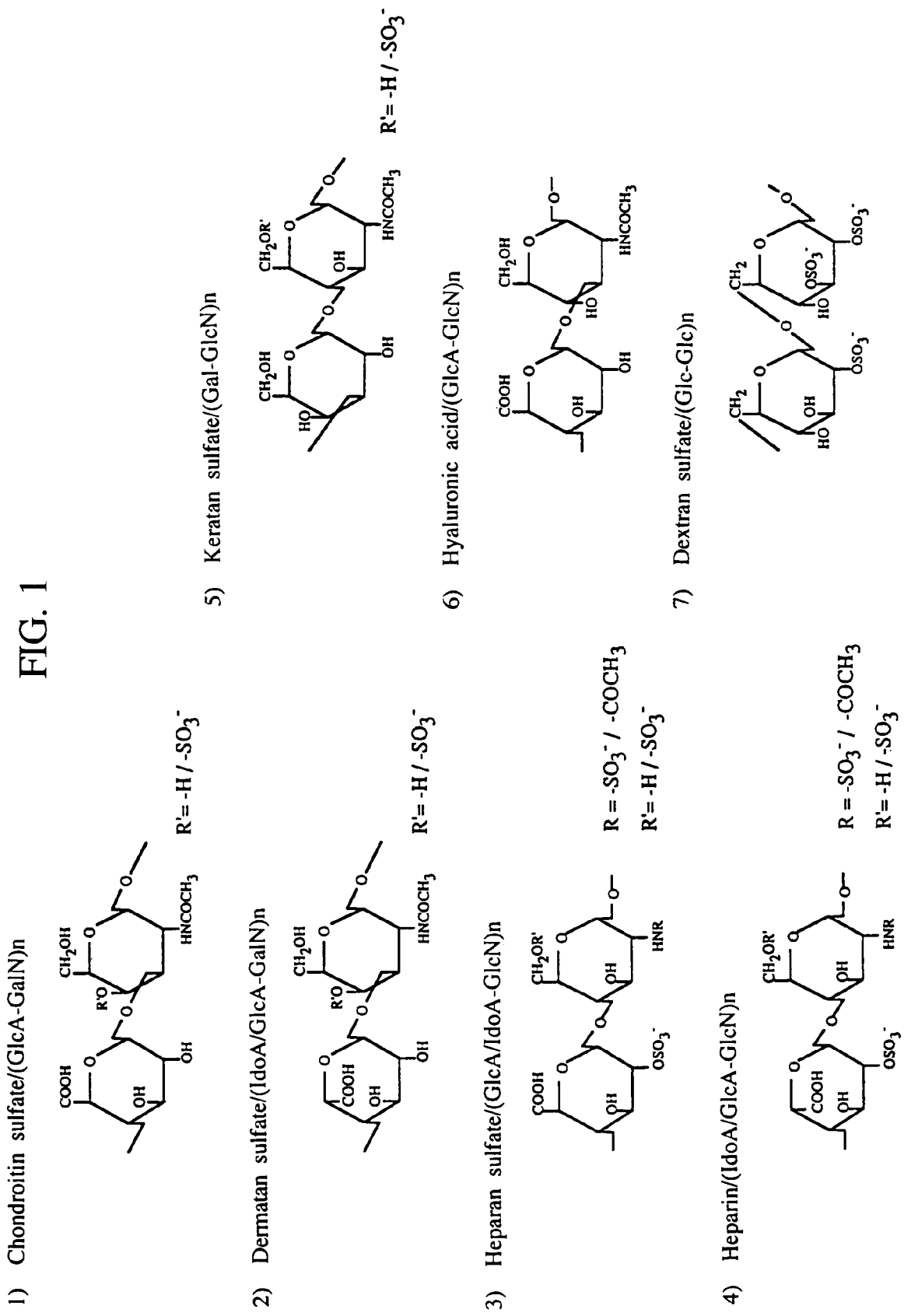
FIG. 1 shows typical examples of sulfated polysaccharide and glycosaminoglycan sugar chains.

Hereinbelow, the present invention will be described in detail.

In the present invention, the heparin-binding protein to which sugar chain(s) are to be covalently bonded is a protein having heparin binding property. For example, factors belonging to the FGF family or allied factors, or other proteins with heparin-binding property but without structural similarity to the former proteins may be enumerated. Examples of the other proteins include, but are not limited to, heparin-binding epidermal growth factor-like factor (HB-EGF) and platelet-derived growth factor (PDGF). As specific examples of the factors belonging to the FGF family or allied factors, FGF-1 to -10 and FHF (fibroblast growth factor homologous factor)-1 to -4 are known. The heparin-binding protein of the invention may be covalently bonded to sugar chain(s) through a peptide to which the sugar chain(s) can be added. For example, the heparin-binding protein to which the sugar chain(s) are to be covalently bonded may be the following (a) or (b):

(a) a protein consisting of the amino acid sequence of SEQ ID NO: 1, 3, 5, 17, 19, 21, 23, 25, 27 or 29;

(b) a protein which consists of the amino acid sequence of SEQ ID NO: 1, 3, 5, 17, 19, 21, 23, 25, 27 or 29 having deletion, substitution, addition or modification of one or several amino acids, which has FGF activity and to which the sugar chain(s) can be added.

Proteins having the amino acid sequences of SEQ ID NOS: 1, 3, 5, 17, 19, 21, 23, 25, 27 and 29 are encoded by, for example, the DNA sequences of SEQ ID NOS: 2, 4, 6, 18, 20, 22, 24, 26, 28 and 30, respectively. These proteins contain a peptide sequence to which sugar chain(s) can be added and a sequence for a signal peptide in addition to a peptide sequence for a factor belonging to the FGF family. The heparin-binding protein of the present invention includes not only the protein primarily defined by a cDNA shown in the sequence listing but also a protein in which a peptide sequence for secretion (called the signal peptide) located at the amino terminal when secreted from cells is cut off. The utility of a heparin-binding protein which is contained in the pharmaceutical composition of the invention as an active ingredient will not vary even if the protein is produced in a form lacking the signal peptide from the beginning.

The sugar chain(s) to be covalently bonded to the heparin-binding protein may be any sugar chain(s) as long as the protein is functionalized by covalently bonding the sugar chain(s). Examples of the sugar chain(s) include, but are not limited to, sulfated polysaccharides such as heparan sulfate, chondroitin sulfate, glycosaminoglycans, N-linked sugar chains and O-linked sugar chains. The term "functionalize" used herein means increasing the activity of a protein of interest. As an example of functionalization, there may be given a case in which the residual activity of a protein after treatment with heat, acid or alkali is increased by adding sugar chain(s) to the protein by covalent bond(s). The "sulfated polysaccharide(s)" used herein is a general term for various sugar chain structures which are elongating from xylose linked to a serine residue present in the primary structure of proteins or elongating on the non-reducing end side of N-linked sugar chains or O-linked sugar chains to be described later, or which are present in a free form.

Many of such sugar chains are composed of repeating disaccharides of aminosugar and uronic acid (or galactose), and some of their hydroxyl groups or amino groups are substituted with sulfate groups. Glycosaminoglycans are polysaccharides having a structure similar to those described above, but they include those which do not have any substitution with sulfate groups. All of the above-mentioned polysaccharides are designated herein generically "sulfated polysaccharides or the like".

Figure 2:
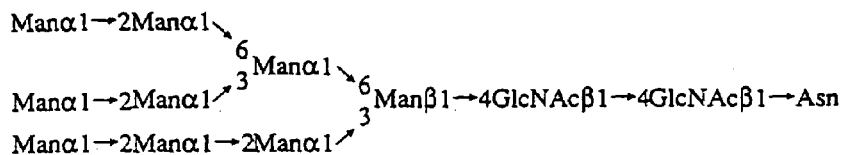
FIG. 2 shows typical examples of N-linked sugar chains.
Figure 2:
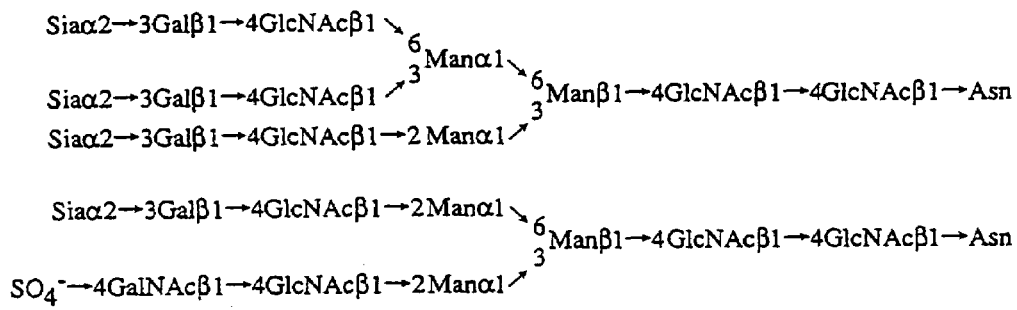
Figure 2:
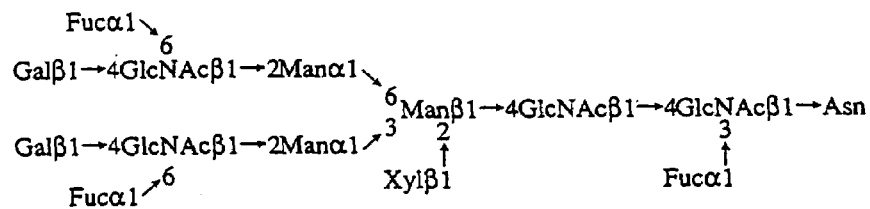
Figure 2:
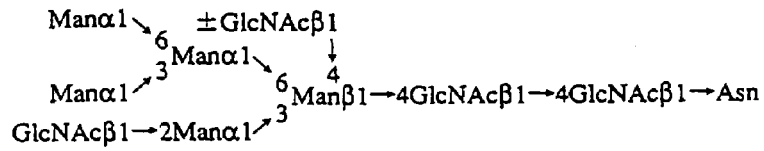

Their specific structures are described, for example, in *Destiny of Sugar Chains in Cells*, Nagai, Hakomori and Kobata (Eds.), Kodansha Scientific Co. FIG. 1 shows their typical sugar chain sequences. The "N-linked sugar chain(s)" used herein is a general term for various sugar chain(s) structures elongating from N-acetylglucosamine linked to an asparagine residue present in the primary structure of proteins. Their specific structures are described, for example, in *Destiny of Sugar Chains in Cells*, Nagai, Hakomori and Kobata (Eds.), Kodansha Scientific Co. FIG. 2 shows their typical sugar chain sequences. The "O-linked sugar chain(s)" used herein is a general term for various sugar chain(s) structures elongating from N-acetylgalactosamine linked to a serine or threonine residue present in the primary structure of proteins. Their specific structures are described, for example, in *Destiny of Sugar Chains in*

Figure 3:
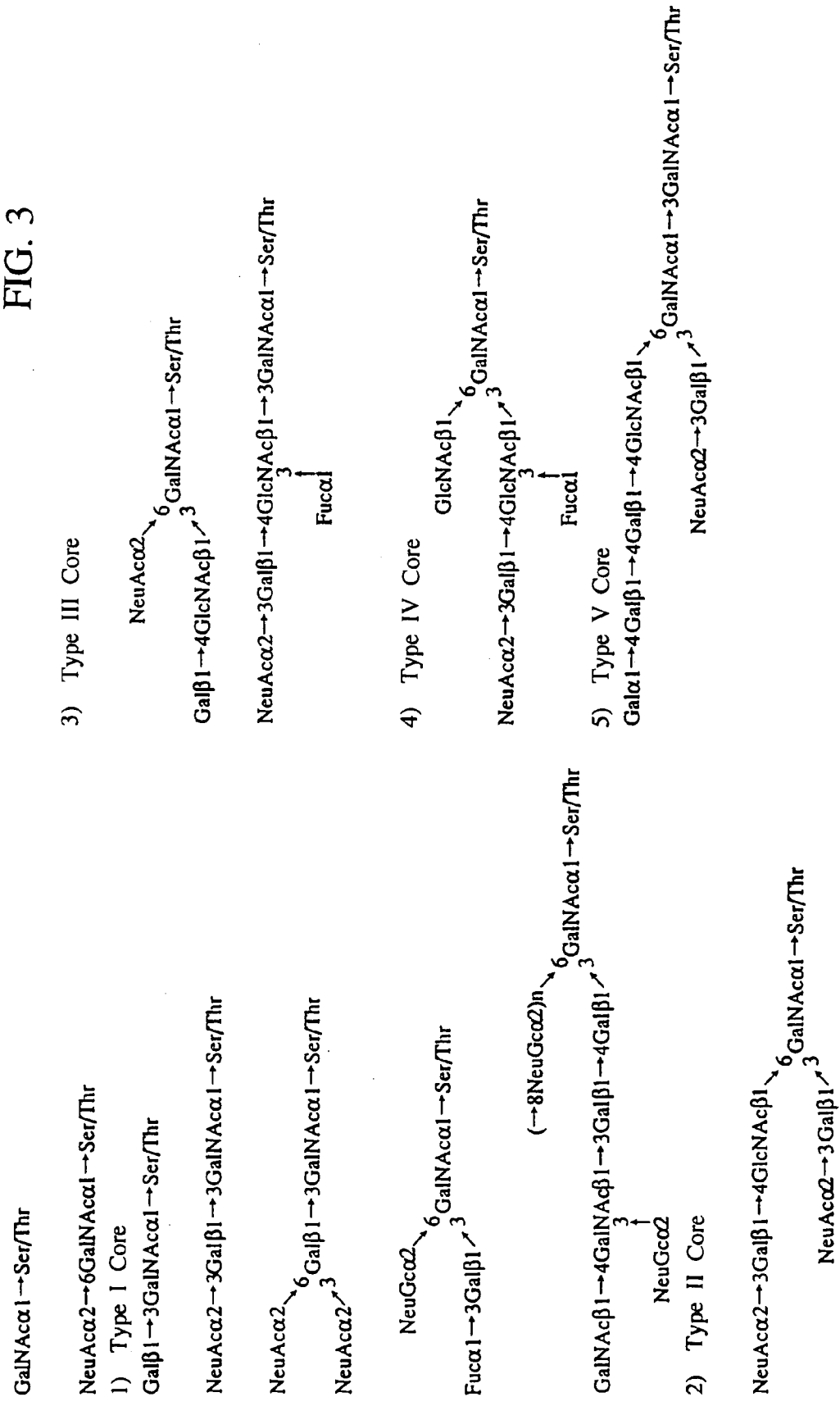
FIG. 3 shows typical examples of O-linked sugar chains.

Cells, Nagai, Hakomori and Kobata (Eds.), Kodansha Scientific Co. FIG. 3 shows their typical sugar chain sequences. These sulfated polysaccharides or the like, N-linked sugar chains and O-linked sugar chains may have addition, deletion, substitution or modification in a part of their sugar chain sequences as long as they retain their functions.

When sugar chain(s) are attached to a heparin-binding protein, the sugar chain(s) alone may be covalently bonded to the heparin-binding protein directly. Alternatively, a peptide chain of any length to which sugar chain(s) are covalently bonding may be covalently bonded to a heparin-binding protein.

In order to produce the heparin-binding protein of the invention to which sugar chain(s) are covalently bonded (hereinafter, referred to as the "sugar chain(s)-added heparin-binding protein"), first, a cDNA coding for a peptide to which sugar chain(s) can be added is ligated to a cDNA coding for a heparin-binding protein. The ligated cDNA is incorporated into an appropriate expression vector, which is then introduced into a host cell having sugar chain(s) addition pathway to thereby express sugar chain(s)-added heparin-binding protein.

cDNAs coding for various heparin-binding proteins can be obtained by designing appropriate primers from a sequence registered in a gene bank such as DDBJ (DNA Data Bank of Japan) and performing RT-PCR (reverse transcription PCR) with the primers and mRNA from the relevant tissue of the relevant animal.

In order to produce a sulfated polysaccharide or the like-added heparin-binding protein, first, a cDNA coding for a heparin-binding protein is ligated to a cDNA coding for a peptide which is known to undergo addition of a sulfated polysaccharide or the like. The ligated cDNA is incorporated into an appropriate host cell expression vector, which is then introduced into a host cell to thereby express the sulfated polysaccharide or the like-added heparin-binding protein. As the peptide which is known to undergo addition of a sulfated polysaccharide or the like, the core protein or a part thereof of various proteoglycans (e.g. syndecan, glypican, perlecan) may be used. As a part of the core protein of a proteoglycan, a peptide comprising a Ser-Gly repeat sequence (which is believed to be the sugar chain(s) addition site in proteoglycans) may be used.

In order to produce an N-linked sugar chain(s)-added heparin-binding protein, first, a cDNA coding for a heparin-binding protein is ligated to a cDNA coding for a peptide which is known to undergo addition of N-linked sugar chain(s). The ligated cDNA is incorporated into an appropriate host cell expression vector, which is then introduced into a host cell to thereby express the N-linked sugar chain(s)-added heparin-binding protein. Specific examples of the peptide which is known to undergo addition of N-linked sugar chain(s) include Asn-X-Thr and Asn-X-Ser (wherein X is any amino acid except proline).

In order to produce O-linked sugar chain(s)-added heparin-binding protein, first, a cDNA coding for a heparin-binding protein is ligated to a cDNA coding for a peptide which is known to undergo addition of O-linked sugar chain(s). The ligated cDNA is incorporated into an appropriate host cell expression vector, which is then introduced into a host cell to thereby express the O-linked sugar chain(s)-added heparin-binding protein. As a specific examples of the peptide which is known to undergo addition of O-linked sugar chain(s), Ala-Thr-Pro-Ala-Pro may be given.

As the site to which sugar chain(s) are bonded, a site forming a turn in the secondary structure of a heparin-binding protein or a site near one of the ends, or a site which would not change the tertiary structure of the protein greatly by addition of the sugar chain(s) is preferable.

One example of the method for producing sugar chain(s)-added heparin-binding protein of the invention will be described below.

First, an oligonucleotide coding for a secretion signal and a peptide which is known to undergo addition of sugar chain(s) is synthesized or amplified by PCR. The resultant oligonucleotide is incorporated at the 5' end of a plasmid coding for a heparin-binding protein.

As the secretion signal and the peptide which is known to undergo addition of sugar chain(s), an amino terminal of a typical secretion-type glycoprotein may be used, for example. Specifically, the amino acid consisting of the N terminal 40 residues of mouse FGF-6 may be used.

The plasmid coding for a heparin-binding protein can be prepared by incorporating a DNA coding for the heparin-binding protein into an appropriate plasmid. As the plasmid into which a DNA coding for a heparin-binding protein is to be incorporated, any plasmid may be used as long as it is replicated and maintained in a host. For example, pBR322 and pUC18 from *E. coli* and pET-3c which was constructed based on these plasmids may be enumerated.

As a method for incorporating the above-described oligonucleotide into the plasmid coding for a heparin-binding protein, the method described in T. Maniatis et al.: *Molecular Cloning*, Cold Spring Harbor Laboratory, p. 239 (1982) may be given, for example.

From the thus prepared plasmid, a region comprising a nucleotide sequence coding for a secretion signal, a peptide which is known to undergo addition of sugar chain(s) and a heparin-binding protein (hereinafter, referred to as a "region comprising a nucleotide sequence coding for sugar chain(s)-added heparin-binding protein") is cut out. This region is ligated to the downstream of a promoter in a vector suitable for expression to thereby obtain an expression vector.

The above-described region comprising a nucleotide sequence coding for sugar chain(s)-added heparin-binding protein may have ATG at its 5' end as a translation initiation codon and TAA, TGA or TAG at its 3' end as a translation termination codon. In order to express the protein encoded in the coding region, a promoter is ligated to the upstream of the region. As the promoter to be used in the present invention, any promoter may be used as long as it is appropriate to the host used for the expression of the gene. When the host to be transformed is a *bacillus*, SPO1 promoter, SPO2 promoter, penP promoter or the like may be used. When the host is a yeast, PHO5 promoter, PGK promoter, GAP promoter, ADH promoter or the like may be used. When the host is an animal cell, a promoter from SV40 or a promoter from a retrovirus may be used.

As the plasmid into which the thus constructed recombinant DNA comprising a nucleotide sequence coding for sugar chain(s)-added heparin-binding protein is to be incorporated, any plasmid may be used as long as it can be expressed in the host cell. For example, those vectors which were constructed based on *E. coli*-derived pBR322 and pUC18 may be given.

As a method for incorporating the recombinant DNA into a plasmid, the method described in T. Maniatis et al.: *Molecular Cloning*, Cold Spring Harbor Laboratory, p. 239 (1982) may be given, for example.

By introducing a vector comprising the above-described recombinant DNA into a host cell, a transformant carrying the vector is prepared.

As the host cell, any cell may be used as long as it has sugar chain(s) addition pathway. Specific examples include, but are not limited to, bacilli (e.g. *Bacillus subtilis* DB105), yeasts (e.g. *Pichia pastoris, Saccharomyces cerevisiae*), animal cells (e.g. COS cell, CHO cell, BHK cell, NIH3T3 cell, BALB/c3T3 cell, HUVE cell, LEII cell) and insect cells (e.g. Sf-9 cell, Tn cell).

The above-mentioned transformation may be performed by a conventional method commonly used for each host. Alternatively, an applicable method may be used though it is not commonly used. For example, when the host is a yeast, a vector comprising the recombinant DNA is introduced into competent cells (prepared by the lithium method or the like) by the temperature shock method or electroporation. When the host is an animal cell, a vector comprising the recombinant DNA is introduced into cells at the logarithmic growth phase or the like by the calcium phosphate method, lipofection or electroporation.

By culturing the thus obtained transformant in a medium, a sugar chain(s)-added heparin-binding protein is produced. As the medium for culturing the transformant, a conventional medium commonly used for each host may be used. Alternatively, an applicable medium may be used even if it is not commonly used. For example, when the host is a yeast, YPD medium or the like may be used. When the host is an animal cell, Dulbecco's MEM supplemented with animal serum, or the like may be used. The cultivation may be performed under conditions commonly employed for each host. Alternatively, applicable conditions may be used even if they are not commonly used. For example, when the host is a yeast, the cultivation is carried out at about 25–37° C. for about 12 hours to 2 weeks. If necessary, aeration or agitation may be carried out. When the host is an animal cell, the cultivation is carried out at about 32–37° C. under 5% $CO_2$ and 100% humidity for about 24 hours to 2 weeks. If necessary, the conditions of the gas phase may be changed or agitation may be carried out.

In order to obtain a sugar-chain(s) added heparin-binding protein from the culture of the above-described transformant, the protein released into the culture fluid may be directly recovered from a supernatant after centrifugation. Alternatively, when the protein is to be extracted from the cultured microorganisms or cells, the protein may be obtained by disrupting the cultured microorganisms or cells with a homogenizer, a French press, ultrasonic waves, lysozyme and/or by freeze-thawing to thereby elute the protein of interest to the outside of the cells, and then recovering the protein from soluble fractions. If the protein of interest is contained in insoluble fractions, insoluble fractions may be recovered by centrifugation after disruption of the microorganisms or cells and then solubilized with a buffer containing guanidine hydrochloride or the like, to thereby recover the protein of interest from the resultant soluble fractions. Alternatively, the cultured microorganisms or cells may be disrupted by a direct treatment with a buffer containing a protein denaturing agent such as guanidine hydrochloride to thereby elute the protein of interest to the outside of the cells.

In order to purify a sugar chain(s)-added heparin-binding protein from the above-mentioned supernatant, known separation/purification methods may be used in an appropriate combination. Specific examples of these known separation/purification methods include salting out, solvent precipitation, dialysis, ultrafiltration, gel filtration, SDS-polyacrylamide gel electrophoresis, ion exchange chromatography, affinity chromatography, reversed phase high performance liquid chromatography and isoelectric focusing. Further, affinity chromatography using heparin sepharose as a carrier may be applicable to a large number of heparin-binding proteins.

The thus obtained sample may be dialyzed and freeze-dried to obtain dry powder if the activity of the sugar chain(s)-added heparin-binding protein is not damaged by such processing. Further, in storing the sample, addition of serum albumin to the sample is effective for preventing adsorption of the sample to the container.

The inclusion of an extremely small amount of a reducing agent in the purification process or the storing process is preferable for preventing oxidation of the sample. As the reducing agent, β-mercaptoethanol, dithiothreitol, glutathione or the like may be used.

The sugar chain(s)-added heparin-binding protein of the invention may also be produced by attaching sugar chain(s) to a heparin-binding protein by a chemical method. As the specific method, the following a) or b), or a combination thereof may be used.

a) For example, first, sugar chain(s) are completed by a biological method, a chemical synthesis method or a combination thereof. At that time, a residue appropriate for protein binding may be introduced at one end of the sugar chain(s). For example, an aldehyde group is formed by reducing and partially oxidizing the reducing end of the completed sugar chain(s). Then, this aldehyde group is attached to an amino group in a protein by an amino bond to thereby complete the joining of the sugar chain(s) and the protein.

b) For example, first, an aldehyde group is formed by reducing and partially oxidizing the reducing end of a monosaccharide or a residue appropriate for protein binding which is bound to a monosaccharide. Then, this aldehyde group is attached to an amino group in a protein by an amino bond to thereby complete the joining of the monosaccharide and the protein. An additional monosaccharide or sugar chain(s) are attached to a hydroxyl group or the like of the above monosaccharide to thereby complete sugar chain(s). For this attachment, a biological method, a chemical synthesis method or a combination thereof may be considered.

A heparin-binding protein functionalized by covalently bonding thereto sugar chain(s) can be used as a medicine. For example, the sugar chain(s)-added heparin-binding protein of the invention regulates the physiological function of FGF. Specifically, the physiological function of FGF is to promote or inhibit the growth of fibroblast, vascular endothelial cell, myoblast, cartilage cell, osteoblast and glia cell. Therefore, the sugar chain(s)-added heparin-binding protein of the invention is effective for promoting cell growth and tissue regeneration in liver or the like; for curing wounds and regulating nervous function; and for regulating the growth of fibroblast or the like. The protein of the invention is useful for preventing or treating various diseases such as fibroblastoma, angioma, osteoblastoma, death of neurocytes, Alzheimer's disease, Parkinson's disease, neuroblastoma, amnesia, demensia and myocardial infarction. The protein of the invention can also be used as a trichogenous agent or a hair-growing agent.

The sugar chain(s)-added heparin-binding protein obtained as described above may be formulated into pharmaceutical compositions such as liquid, lotions, aerosols, injections, powder, granules, tablets, suppositories, enteric coated tablets and capsule, by mixing the protein with pharmaceutically acceptable solvents, vehicles, carriers, adjuvants, etc. according to conventional formulation methods.

The content of the sugar chain(s)-added heparin-binding protein, which is an active ingredient, in the pharmaceutical composition may be about 0.0000000001 to 1.0% by weight.

The pharmaceutical composition can be administered parenterally or orally to mammals, e.g. human, mouse, rat, rabbit, dog, cat, etc. in a safe manner. The dose of the pharmaceutical composition may be appropriately changed depending on the dosage form, administration route, conditions of the patient and the like. For example, for administration to mammals including human, 0.0001 to 100 mg of the sugar chain(s)-added heparin-binding protein may be applied to the diseased part several times a day.

The present invention has been described so far taking heparin-binding proteins as an example. However, it should be noted that besides the heparin-binding proteins, natural proteins having no sugar chain(s) can also be functionalized by covalently bonding thereto sugar chain(s).

Deposit of Microorganisms

Clones of *E. coli* DH5 α carrying plasmids incorporating genes coding for the sugar chain(s)-added heparin-binding proteins of the invention (having the DNA sequences of SEQ ID NOS: 2, 4, 18, 20, 22, 24, 26, 28 and 30, respectively) were deposited at the National Institute of Bioscience and Human-technology, Agency of Industrial Science and Technology under Accession Numbers of FERM BP-6428, FERM BP-6424, FERM BP-6427, FERM BP-6431, FERM BP-6429, FERM BP-6430, FERM BP-6423, FERM BP-1625 and FERM BP-6426 on Sep. 10, 1997.

Hereinbelow, the present invention will be described specifically with reference to the following Example. However, the present invention is not limited to this Examples.

EXAMPLE 1

1) Construction of S/FGF-1a-II Plasmid
   1. Preparation of a Human Ryudocan cDNA Fragment
   phR7A8 is a plasmid obtained by inserting a human ryudocan cDNA (PCR product) into the EcoR V site of pBluescript II (KS+) cloning vector. This plasmid contains a partial sequence from position 7 to position 2610 in the mRNA sequence shown under Accession No. D13292 (see B.B.R.C. Vol. 190, No. 3, pp. 814–822, 1993).

This plasmid was digested with Pvu II. Using the resultant DNA fragment of 2,232 base pairs as a template, a PCR (polymerase chain reaction) was performed. As primers, #109 (5'-TTG TCG ACC CAC CAT GGC CCC CGC CCG TCT-3') (SEQ ID NO: 7) and #111 (5'-TTG ATA TCT AGA GGC ACC AAG GGA TG-3')(SEQ ID NO: 8) were used. The specifically amplified 276 bp band was separated by electrophoresis. After extraction, this fragment was double-digested with EcoR V and Sal I. The resultant 268 bp band was separated, extracted and then used in the ligation described below.

2. FGF-1a/pBluescript II (KS+)
   A PCR was performed using human FGF-1 cDNA as a template and #967 (5'-GCG TCG ACA GCG CTA ATT ACA AGA AGC CCA AAC TC-3') (SEQ ID NO: 9) and #630 (5'-CCG AAT TCG AAT TCT TTA ATC AGA AGA GAC TGG-3')(SEQ ID NO: 10) as primers. The specifically amplified 434 bp band was separated by electrophoresis. After extraction, this fragment was double-digested with EcoR I and Sal I. The resultant 422 bp band was separated, extracted and then inserted into pBluescript II (KS+) cloning vector (2934 bp) double-digested with EcoR I and Sal I, where upon FGF-1a/pBluescript 1a/pBluescript II (KS+) was produced.

FGF-1a/pBluescript II (KS+) was digested with Aor51H I and Sal I in this order. The resultant 2626 bp band was separated, extracted and then used in the ligation described below.

3. Preparation of S/FGF-1a-II Chimeric Gene EcoR V/Sal I fragment (a PCR product from human ryudocan) and Aor51H I/Sal I fragment from FGF-1a/pBluescript II (KS+) were subjected to a DNA ligation to produce S/FGF-1a-II/pBluescript II (KS+) vector. Subsequently, this vector was double-digested with EcoR I and Sal I to give a 678 bp band, which was then separated and extracted. The resultant fragment was inserted into pMEXneo expression vector (5916 bp) double-digested with EcoR I and Sal I, where upon S/FGF-1a-II/pMEXneo was produced. This expression vector comprises the nucleotide sequence shown in SEQ ID NO: 2.

2) Expression of S/FGF-1a-II
   The resultant S/FGF-1a-II/pMEXneo was transferred into CHO-K1 cells (Chinese hamster ovary cell K1 substrain) by lipofection. Then, the cells were cultured in the presence of Geneticin to select gene-transferred cells. The selected cells were grown until the culture plate became almost full. Then, the medium was exchanged with a serum-free medium to increase the substance productivity of the cells. Thereafter, the medium was exchanged with a fresh one every two days. The resultant conditioned medium was subjected to low speed centrifugation, and the resultant supernatant was stored at 4° C.

3) Construction of N-FGF6/1a-IV Plasmid
   1. Preparation of a Mouse FGF-6 cDNA Fragment
   A PCR was performed using mouse FGF-6 cDNA as a template and #1048 (5'-GCG TCG ACC CAC CAT GTC CCG GGG AGC AGG ACG TGT TCA GGG CAC GCT-GCA GGC TCT CGT CTT C-3')(SEQ ID NO: 11) and #968 (5'-GCG ATA TCC AGT AGC GTG CCG TTG GCG CG-3')(SEQ ID NO: 12) as primers. The specifically amplified 138 bp band was separated by electrophoresis. After extraction, this fragment was double-digested with EcoR V and Sal I. The resultant 130 bp band was separated, extracted and then used in the ligation described below.

2. Preparation of N-FGF6/1a-IV Chimeric Gene
   EcoR V/Sal I fragment (a PCR product from mouse FGF-6) and Aor51H I/Sal I fragment from FGF-1a/pBluescript II (KS+) were subjected to a DNA ligation to produce N-FGF-6/1a-IV/pBluescript II (KS+) vector. Subsequently, this vector was double-digested with EcoR I and Sal I to give a 540 bp band, which was then separated and extracted. The resultant fragment was inserted into pMEXneo expression vector (5916 bp) double-digested with EcoR I and Sal I, where upon N-FGF-6/1a-IV/pMEXneo was produced. This expression vector comprises the nucleotide sequence shown in SEQ ID NO: 4.

4) Expression of N-FGF-6/1a-IV
   N-FGF-6/1a-IV was secreted into a culture supernatant by transferring N-FGF-6/1a-IV/pMEXneo into CHO-K1 cells in the same manner as described above for S/FGF6/1a-II.

5) Construction of O-FGF-6/1a Plasmid
   1. Preparation of N-FGF6/1a<NQ> Chimeric Gene
   A PCR was performed using N-FGF6/1a/pBluescript II (KS+) vector as a template and #105 (5'-GCG TCG ACC CAC CAT GTC-3') (SEQ ID NO: 13) and #124 (5'-GCG ATA TCC AGT AGC GTG CCT TGG GCG CG-3')(SEQ ID NO: 14) as primers. The specifically amplified 138 bp band was separated by electrophoresis. After extraction, this fragment was double-digested with EcoR V and Sal I. The resultant 130 bp band was subjected to the ligation described below together with Aor51H I/Sal I fragment from FGF-1a/pBluescript II (KS+), to thereby yield N-FGF-6/1a<NQ>/pBluescript II (KS+) vector.

2. Preparation of O-FGF-6/1a Chimeric Gene

A primary PCR was performed using N-FGF6/1a<NQ>/pBluescript II (KS+) vector as a template and #098 (5'-GCT GGA GGA GGC TGC TAC TCC AGC TTC AAA CCA TTA CA-3') (SEQ ID NO: 15) and #116 (5=-GCC GCT CTA GAA CTA GTG GAT-3') (SEQ ID NO: 16) as primers. The specifically amplified 210 bp band was purified. Using this PCR product and #115 (5'-AAC AAA AGC TGG GTA CCG GG-3') as primers, a secondary PCR was performed. The specifically amplified 631 bp band was separated by electrophoresis. After extraction and purification, this fragment was double-digested with EcoR I and Sal I. The resultant 558 bp band was separated, extracted and then inserted into pMEXneo expression vector (5916 bp) double-digested with EcoR I and Sal I, to thereby yield O-FGF-6/1a/pMEXneo. This expression vector comprises the nucleotide sequence shown in SEQ ID NO: 6.

6) Expression of O-FGF-6/1a

O-FGF-6/1a was secreted into a culture supernatant by transferring O-FGF6/1a/pMEXneo into CHO-K1 cells in the same manner as described above for S/FGF-1a-II.

7) Expression of FGF-1a in *E. coli*

The fragment from human FGF-1a cDNA obtained by double digestion with Eco RI and Sal I as described above was incorporated into an *E. coli* expression vector pET3c. *E. coli* BL21 (DE3)pLysS was transformed with the resultant vector. Subsequently, the transformant at the logarithmic growth phase was stimulated with IPTG (isopropylthio-β-galactoside) to induce the expression of the transferred gene. The cells were collected and sonicated for disruption to thereby release FGF-1a, which was then recovered in a centrifugation supernatant.

8) Removal of N-Linked Sugar Chains by Peptide N-Glycosidase F Treatment

N-FGF6/1a-II concentrated with heparin-Sepharose beads was boiled and eluted in an electrophoresis buffer, as will be described later (see Test Example 1). To a part of the resultant solution, NP-40 (final concentration: 1%), Tris-HCl buffer (pH 7.5) and peptide N-glycosidase F (0.3 U) were added and the mixture was kept at 37° C. overnight. Then, the solution was heated at 100° C. for 3 min to terminate the enzyme reaction. This reaction solution was analyzed by SDS-denatured electrophoresis, as will be described later.

Various S/FGF-1a and N-FGF-6/1a genes can be prepared by appropriately altering the PCR primers (#111 and #968) used in "1. Preparation of a Human Ryudocan cDNA Fragment" and "1. Preparation of a Mouse FGF-6 cDNA Fragment" in the above Example and by replacing the restriction enzyme EcoR V with an appropriate enzyme which would generate a blunt end. Examples of such cDNA sequences are shown in SEQ ID NOS: 8, 20, 22, 24, 26 and 28.

Various O-FGF-6/1a genes can be prepared by replacing the template used in the PCR in "2. Preparation of O-FGF-6/1a Chimeric Gene" above with S/FGF-1a-II/pBluescript II (KS+), N-FGF6/1a-IV/pBluescript II (KS+) or the like, or by appropriately altering the PCR primers (#098, #116 and #115), or by a combination of the both methods. An example of such a cDNA sequence is shown in SEQ ID NO: 30.

TEST EXAMPLE 1

SDS-Denatured Electrophoresis

Figure 4:
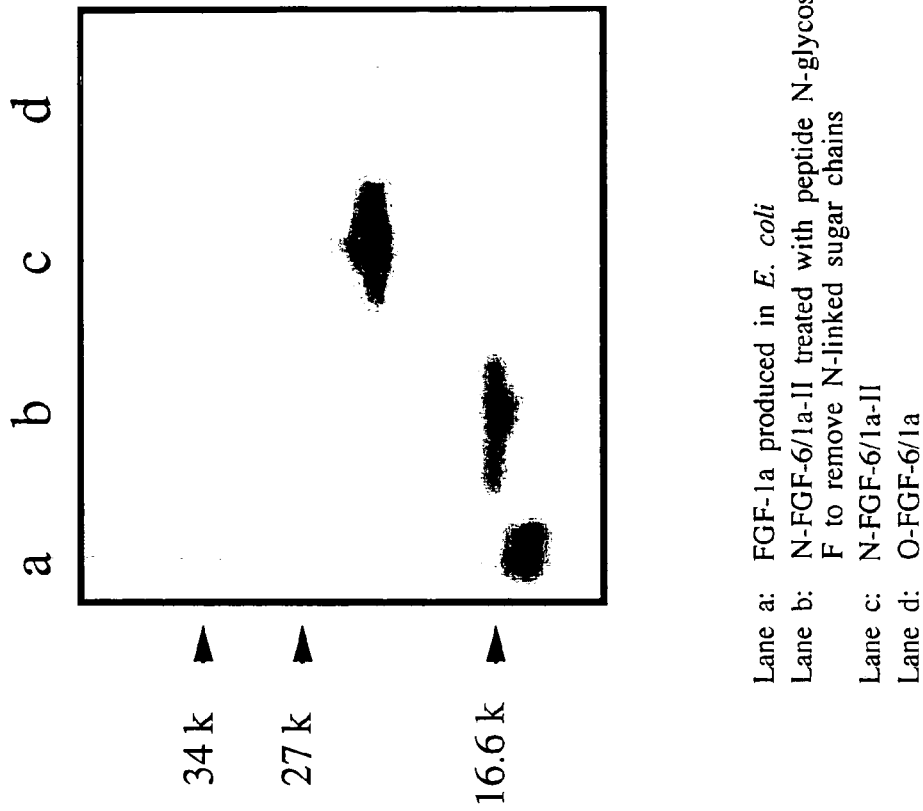
FIG. 4A shows SDS-denatured electrophoregrams of S/FGF-1a-II Protein.
FIG. 4B shows SDS-denatured electrophoregrams of N-FGF-1a-IV and O-FGF-1a Proteins.

Heparin Sepharose beads added to conditioned media of various FGF-1a-like proteins-secreting cells were individually washed and then boiled directly with an electrophoresis buffer (containing SDS and 2-' mercaptoethanol). The eluted protein was used as a sample. This sample was electrophoresed on 12.5% acrylamide gel in the presence of SDS and 2-mercaptoethanol. After being electrically transferred onto a nitrocellulose membrane, the protein was stained with anti-FGF-1 monoclonal antibody and horseradish peroxidase-labelled anti-mouse IgG antibody, followed by detection by the chemiluminescence method (FIG. 4). In the Figure, the arrows at the left side indicate the locations of standard proteins with known molecular weights and their molecular weights (in daltons). Panel A) shows an SDS-denatured electrophoregram of S/FGF-1a-II. Panel B) shows SDS-denatured electrophoregrams of FGF-1a produced in *E. coli* (lane a); N-FGF-1a-IV obtained by treating N-FGF-6/1a-IV with peptide N-glycosidase F for removal of N-linked sugar chains (lane b); N-FGF6/1a-IV (lane c) and O-FGF-6/1a (lane d).

TEST EXAMPLE 2

DNA Synthesis Promoting Activity

The cell cycle of HUVEC (human umbilical cord-derived vascular endothelial cell) stops even in the presence of 15% serum if growth factors such as FGF are lacking. S/FGF-1a-II, N-FGF6/1a-IV, O-FGF-6/1a, or FGF-1a produced in *E. coli* was added to HUVEC in such a state. Eighteen hours later, radio-labelled thymidine was allowed to be taken up for 6 hours. The amount of radioactivity taken up into DNA during this period was regarded as indicating the amount of the newly synthesized DNA.

Figure 5B:
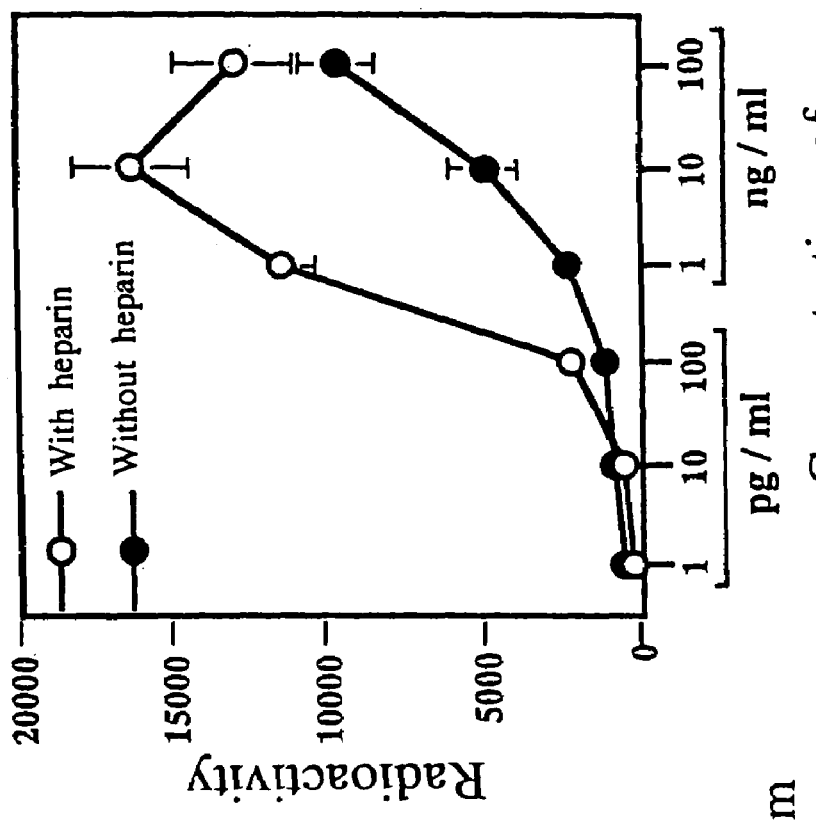
Figure 5A:
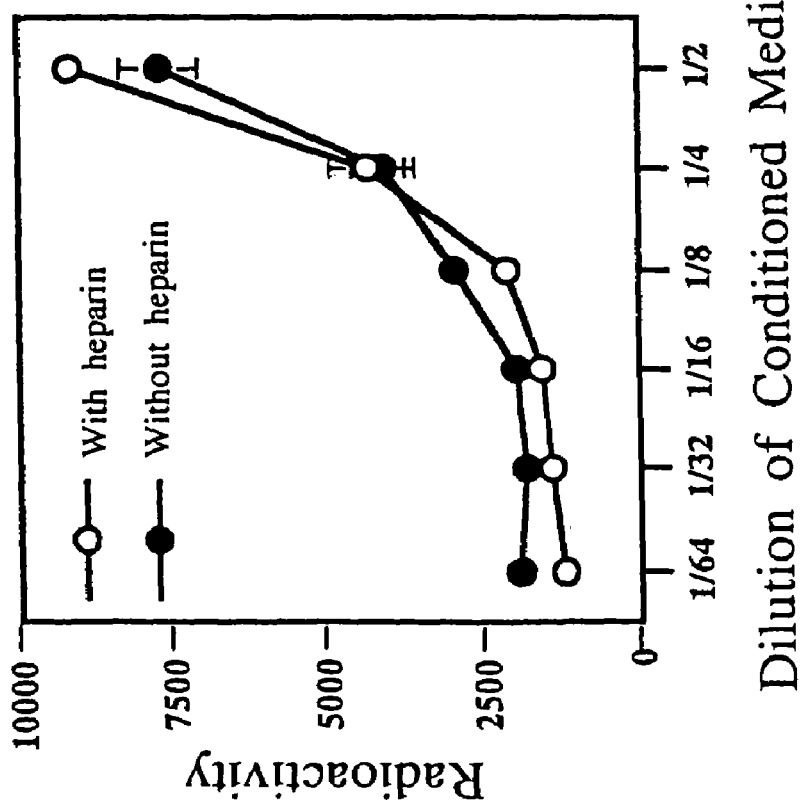
FIG. 5A shows the DNA synthesis promoting activity on HUVEC of S/FGF-1a-II.

1. DNA Synthesis Promoting Effect (Heparin Non-Dependent) of S/FGF-1a-II on Human Vascular Endothelial Cell A conditioned medium was prepared from a serum-free medium of S/FGF-1a-II gene-transferred cells. This conditioned medium was dialyzed against PBS and then added to HUVEC in the presence (5 µg/ml) or absence of heparin, for examining the DNA synthesis promoting activity of S/FGF-1a-II on HUVEC (FIG. 5A). As a result, unlike FGF-1a produced in *E. coli*(FIG. 5B), S/FGF-1a-II promoted the DNA synthesis of HUVEC in a non-heparin-dependent manner (FIG. 5).

Figure 8:
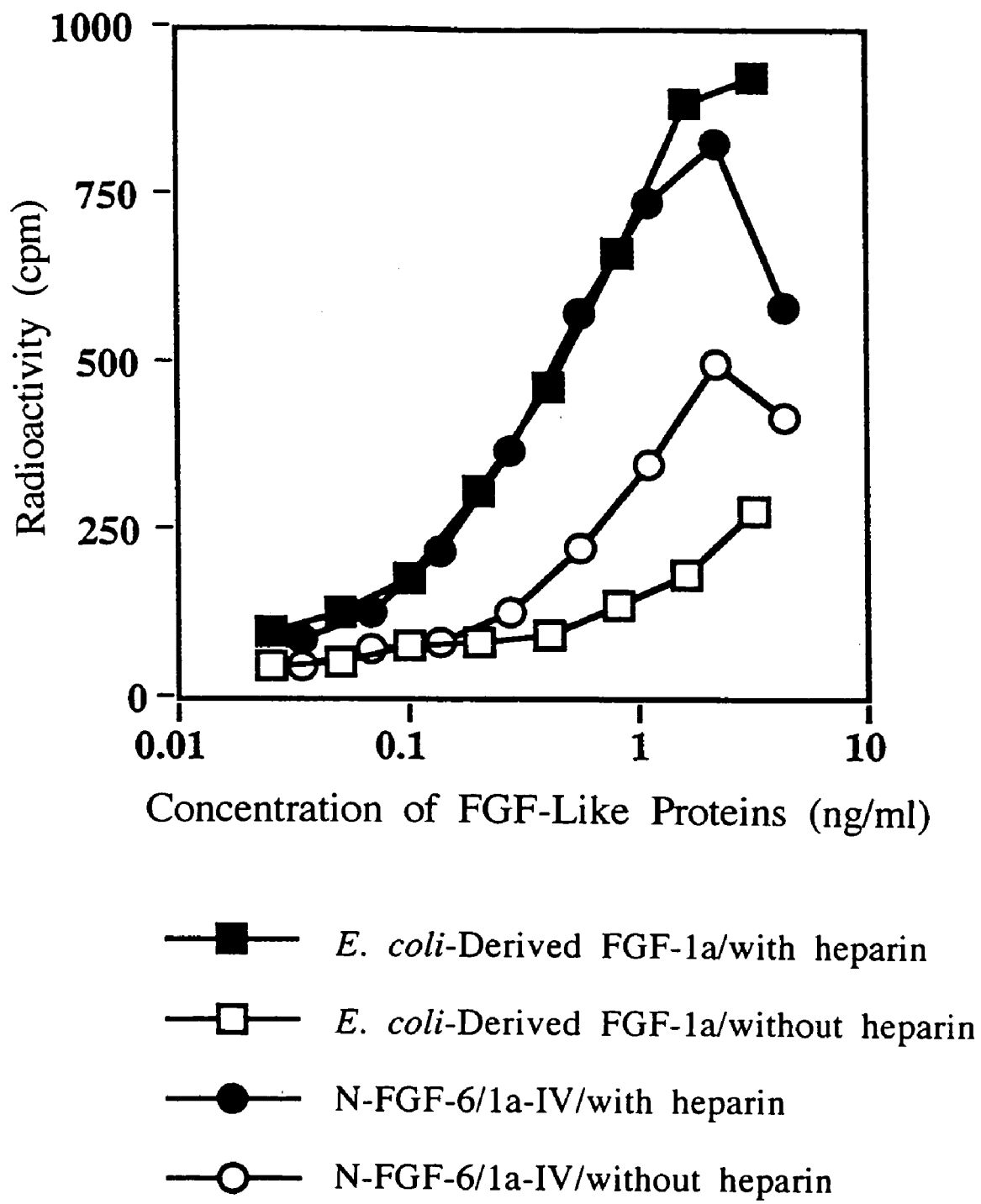

2. DNA Synthesis Promoting Effect of N-FGF6/1a-IV on Human Vascular Endothelial Cell A conditioned medium was prepared from a serum-free medium of N-FGF-6/1a-IV gene-transferred cells. This conditioned medium was dialyzed against PBS and then added to HUVEC in the presence (5 µg/ml) or absence of heparin, for examining the DNA synthesis promoting activity of N-FGF6/1a-IV on HUVEC. As a result, like FGF-1a produced in *E=coli*, N-FGF6/1a-IV promoted the DNA synthesis of HUVEC. However, its heparin dependency was weak, and N-FGF6/1a-IV exhibited stronger DNA synthesis promoting activity than FGF-1a from *E=coli* in the absence of heparin (FIG. 8).

TEST EXAMPLE 3

Heparin Affinity Chromatography

The heparin affinity of S/FGF-1a-II obtained in 2) in the above Example was examined. Heparin-Sepharose beads were added to a conditioned medium of S/FGF-1a-II-secreting cells and agitated at 4° C. for 2 hours or more. Beads precipitating by low speed centrifugation were recovered and washed sufficiently in physiological PBS (phosphate buffered saline, pH 7.4), followed by elution of the protein bound to heparin-fixed beads with PBS containing 2.5 M NaCl. After addition of distilled water to lower the salt concentration, this eluate was again applied to a high performance liquid chromatography column packed with heparin affinity beads. S/FGF-1a-II was eluted using NaCl density gradient.

Figure 9:
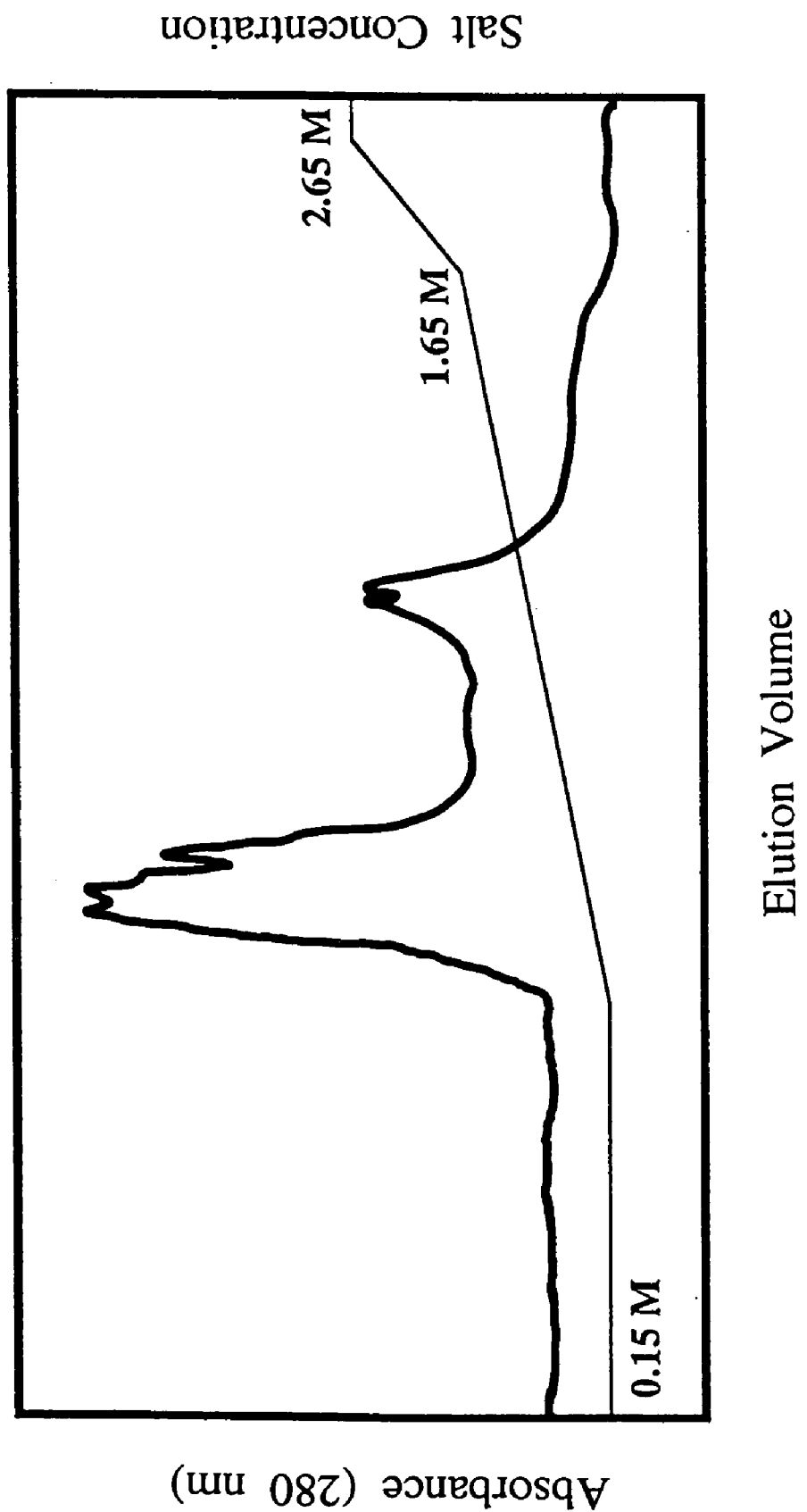
FIG. 9 shows the heparin affinity of S/FGF-1a-II.

While FGF-1a from *E. coli* was eluted at about 1.0 M NaCl, S/FGF-1a-II was eluted at about 0.4 M NaCl. Thus, it appears that affinity to the fixed heparin is lowered in S/FGF-1a-II (FIG. 9). The small peak seen around 1.0 M NaCl in FIG. 9 is considered to be a degradation product from S/FGF-1a-II as analyzed by SDS-denatured electrophoresis.

TEST EXAMPLE 4

Thermostability of FGF-1a-Like Proteins

Conditioned media of various FGF-1a-like protein-secreting cells were individually dialyzed against PBS sufficiently. A part of each of the resultant media was retained in PBS kept at 56° C. or 70° C. for 30 minutes, or retained at room temperature for 12 hours. Thereafter, the medium was re-dialyzed against PBS at 4° C. to prepare a sample. The stability of S/FGF-1a-II was determined by subjecting it to DNA synthesis promoting activity test on HUVEC after various treatments and then comparing the resultant activity with the activity of an S/FGF-1a-II sample dialyzed against PBS at 4° C. for 12 hours (FIG. 6A).

Figure 6A:
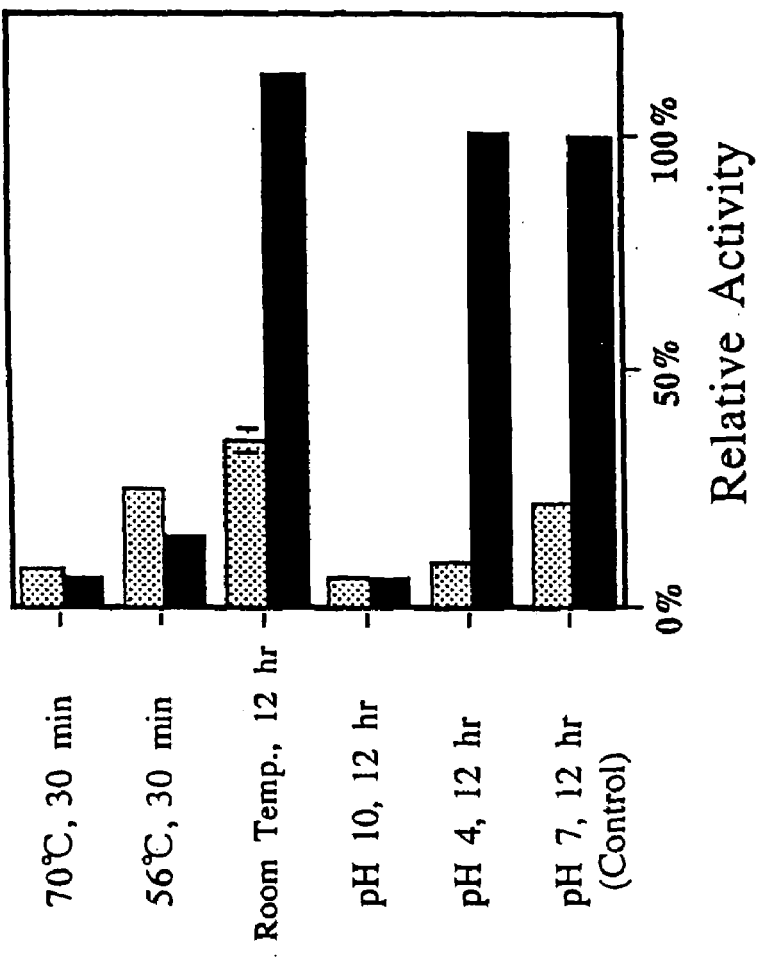
FIG. 6A shows the thermostability, acid resistance and alkali resistance of S/FGF-1a-II.

After retention at room temperature for 12 hours, even the activity of *E. coli*-derived FGF-1a was protected by heparin, but the activity of S/FGF-1a-II was protected regardless of the presence or absence of heparin (FIG. 6A).

Figure 6B:
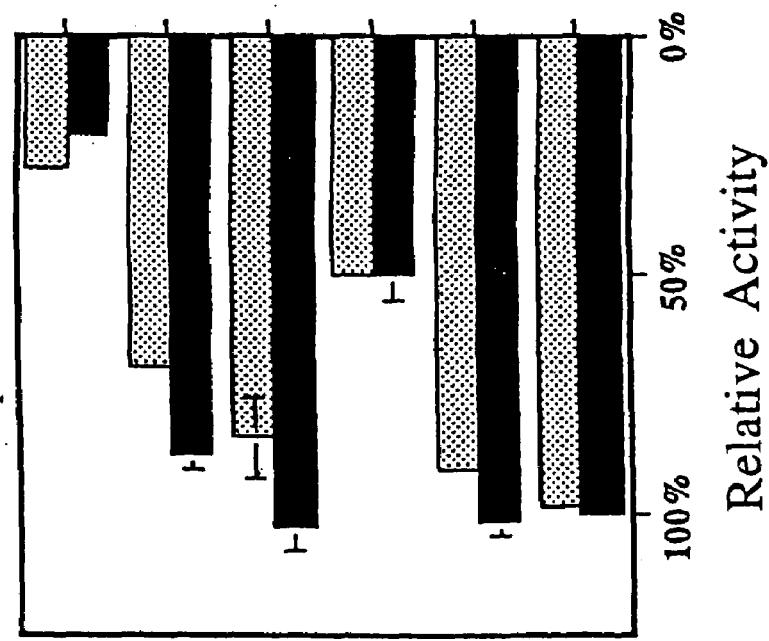

After heat treatment at 56° C. for 30 minutes, *E. coli*-derived FGF-1a was almost deactivated, but S/FGF-1a-II retained about 50% of the activity. Thus, it was considered that its thermostability was improved (FIG. 6B).

TEST EXAMPLE 5

Acid Resistance and Alkali Resistance of FGF-1a-Like Proteins

Conditioned media of various FGF-1a-like protein-secreting cells were individually dialyzed against PBS sufficiently. A part of each of the resultant media was dialyzed in a citrate buffer (pH 4.0) or a sodium carbonate buffer (pH 10.0) for 12 hours and then re-dialyzed against PBS at 4° C. to prepare a sample. The stability of S/FGF-1a-II was determined by subjecting it to DNA synthesis promoting activity test on HUVEC after various treatments and then comparing the resultant activity with the activity of an S/FGF-1a-II sample dialyzed against PBS at 4° C. for 12 hours.

The activity of S/FGF-1a-II decreased little even after acid treatment at pH 4.0 regardless of the presence or absence of heparin; thus, an improvement in acid resistance was recognized (FIG. 6A). After alkali treatment at pH 10.0, *E. coli*-derived FGF-1a was almost deactivated, but S/FGF-1a-II retained about 50% of the activity; thus, an improvement was also recognized in alkali resistance (FIGS. 6A and 6B).

TEST EXAMPLE 6

Stability of FGF-1a-Like Proteins Against Proteolytic Enzymes

Conditioned media of various FGF-1a-like protein-secreting cells were individually dialyzed against PBS sufficiently. To a part of each of the resultant media, trypsin solutions of varying concentrations (0.0001–0.1%) were added and kept at 37° C. for 1 hour. The thus obtained sample was subjected to the SDS-denatured electrophoresis described previously. The intensity of the remaining band was compared to the intensity of the band generated by the sample before trypsin treatment to give an indicator of stability.

Figure 7:
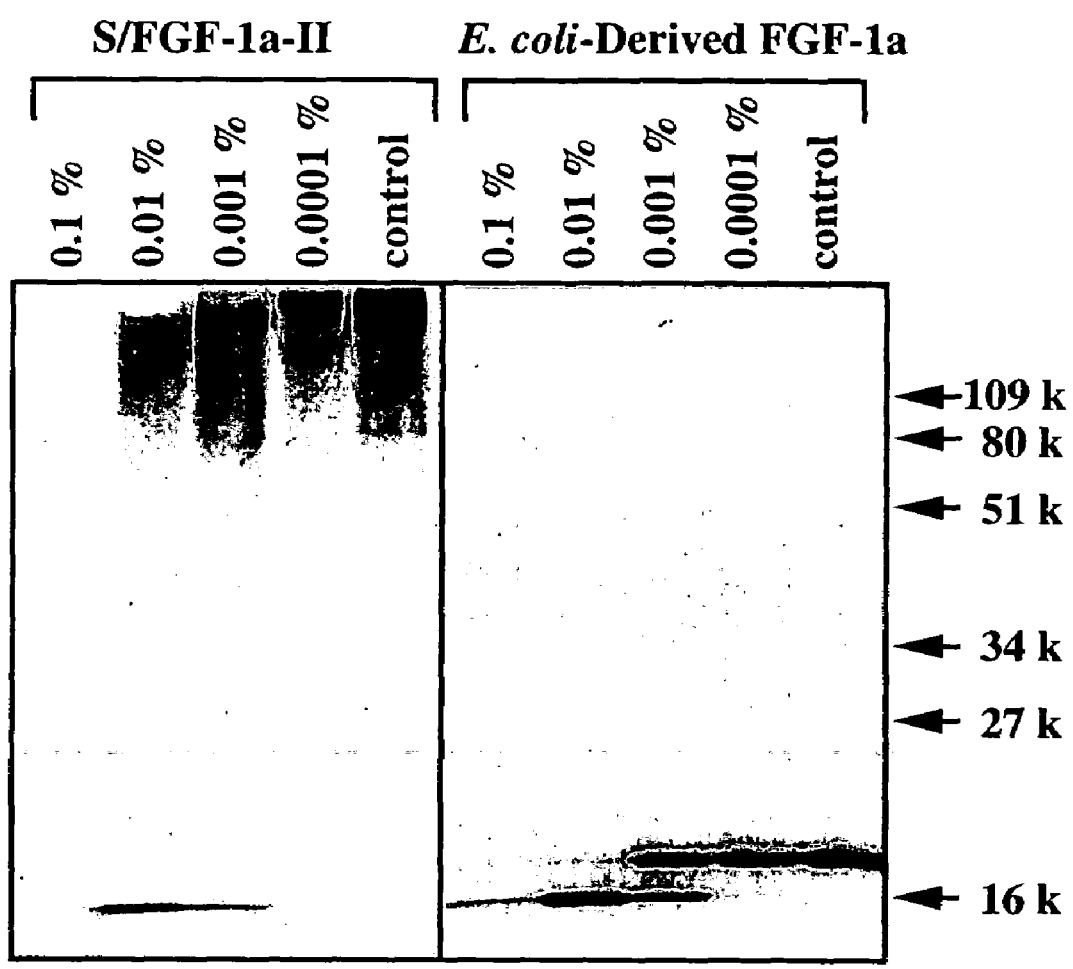

As a result, as shown in FIG. 7, 88% and 35% of the band intensity remained in S/FGF-1a-II after 0.001% and 0.01% trypsin treatment, respectively; however, the band intensity of E. coli-derived FGF-1a decreased to 58% and even to 6% after 0.001% and 0.01% trypsin treatment, respectively. Thus, it was considered that the resistance of S/FGF-1a-II to proteolytic enzymes was increased (FIG. 7).

SEQUENCE LISTING

```
<160> NUMBER OF SEQ ID NOS: 105

<210> SEQ ID NO 1
<211> LENGTH: 179
<212> TYPE: PRT
<213> ORGANISM: Homo sapiens

<400> SEQUENCE: 1

Ala Asp Arg Glu Arg Ser Ile His Asp Phe Cys Leu Val Ser Lys Val
1               5                   10                  15

Val Gly Arg Cys Arg Ala Ser Met Pro Arg Trp Trp Tyr Asn Val Thr
            20                  25                  30
```

-continued

```
Asp Gly Ser Cys Gln Leu Phe Val Tyr Gly Gly Cys Asp Gly Asn Ser
        35                  40                  45

Asn Asn Tyr Leu Thr Lys Glu Glu Cys Leu Lys Lys Cys Ala Thr Val
 50                  55                  60

Thr Glu Asn Ala Thr Gly Asp Leu Ala Thr Ser Arg Asn Ala Ala Asp
 65                  70                  75                  80

Ser Ser Val Pro Ser Ala Pro Arg Arg Gln Asp Ser Glu Asp His Ser
                 85                  90                  95

Ser Asp Met Phe Asn Tyr Glu Glu Tyr Cys Thr Ala Asn Ala Val Thr
                100                 105                 110

Gly Pro Cys Arg Ala Ser Phe Pro Arg Trp Tyr Phe Asp Val Glu Arg
            115                 120                 125

Asn Ser Cys Asn Asn Phe Ile Tyr Gly Gly Cys Arg Gly Asn Lys Asn
130                 135                 140

Ser Tyr Arg Ser Glu Glu Ala Cys Met Leu Arg Cys Phe Arg Gln Gln
145                 150                 155                 160

Glu Asn Pro Pro Leu Pro Leu Gly Ser Lys Val Val Leu Ala Gly
                165                 170                 175

Ala Val Ser

<210> SEQ ID NO 2
<211> LENGTH: 197
<212> TYPE: PRT
<213> ORGANISM: Homo sapiens
<220> FEATURE:
<221> NAME/KEY: SIGNAL
<222> LOCATION: (1)..(18)
<223> OTHER INFORMATION:

<400> SEQUENCE: 2

Ala Gly Ser Phe Leu Ala Trp Leu Gly Ser Leu Leu Ser Gly Val
 1               5                  10                  15

Leu Ala Ala Asp Arg Glu Arg Ser Ile His Asp Phe Cys Leu Val Ser
                 20                  25                  30

Lys Val Val Gly Arg Cys Arg Ala Ser Met Pro Arg Trp Trp Tyr Asn
             35                  40                  45

Val Thr Asp Gly Ser Cys Gln Leu Phe Val Tyr Gly Gly Cys Asp Gly
 50                  55                  60

Asn Ser Asn Asn Tyr Leu Thr Lys Glu Glu Cys Leu Lys Lys Cys Ala
 65                  70                  75                  80

Thr Val Thr Glu Asn Ala Thr Gly Asp Leu Ala Thr Ser Arg Asn Ala
                 85                  90                  95

Ala Asp Ser Ser Val Pro Ser Ala Pro Arg Arg Gln Asp Ser Glu Asp
            100                 105                 110

His Ser Ser Asp Met Phe Asn Tyr Glu Glu Tyr Cys Thr Ala Asn Ala
            115                 120                 125

Val Thr Gly Pro Cys Arg Ala Ser Phe Pro Arg Trp Tyr Phe Asp Val
130                 135                 140

Glu Arg Asn Ser Cys Asn Asn Phe Ile Tyr Gly Gly Cys Arg Gly Asn
145                 150                 155                 160

Lys Asn Ser Tyr Arg Ser Glu Glu Ala Cys Met Leu Arg Cys Phe Arg
                165                 170                 175

Gln Gln Glu Asn Pro Pro Leu Pro Leu Gly Ser Lys Val Val Leu
                180                 185                 190

Ala Gly Ala Val Ser
                195
```

```
<210> SEQ ID NO 3
<211> LENGTH: 153
<212> TYPE: PRT
<213> ORGANISM: Homo sapiens

<400> SEQUENCE: 3

Ile His Asp Phe Cys Leu Val Ser Lys Val Val Gly Arg Cys Arg Ala
1               5                   10                  15

Ser Met Pro Arg Trp Trp Tyr Asn Val Thr Asp Gly Ser Cys Gln Leu
            20                  25                  30

Phe Val Tyr Gly Gly Cys Asp Gly Asn Ser Asn Asn Tyr Leu Thr Lys
        35                  40                  45

Glu Glu Cys Leu Lys Lys Cys Ala Thr Val Thr Glu Asn Ala Thr Gly
50                  55                  60

Asp Leu Ala Thr Ser Arg Asn Ala Ala Asp Ser Ser Val Pro Ser Ala
65                  70                  75                  80

Pro Arg Arg Gln Asp Ser Glu Asp His Ser Ser Asp Met Phe Asn Tyr
            85                  90                  95

Glu Glu Tyr Cys Thr Ala Asn Ala Val Thr Gly Pro Cys Arg Ala Ser
        100                 105                 110

Phe Pro Arg Trp Tyr Phe Asp Val Glu Arg Asn Ser Cys Asn Asn Phe
    115                 120                 125

Ile Tyr Gly Gly Cys Arg Gly Asn Lys Asn Ser Tyr Arg Ser Glu Glu
130                 135                 140

Ala Cys Met Leu Arg Cys Phe Arg Gln
145                 150

<210> SEQ ID NO 4
<211> LENGTH: 58
<212> TYPE: PRT
<213> ORGANISM: Homo sapiens

<400> SEQUENCE: 4

Ile His Asp Phe Cys Leu Val Ser Lys Val Val Gly Arg Cys Arg Ala
1               5                   10                  15

Ser Met Pro Arg Trp Trp Tyr Asn Val Thr Asp Gly Ser Cys Gln Leu
            20                  25                  30

Phe Val Tyr Gly Gly Cys Asp Gly Asn Ser Asn Asn Tyr Leu Thr Lys
        35                  40                  45

Glu Glu Cys Leu Lys Lys Cys Ala Thr Val
50                  55

<210> SEQ ID NO 5
<211> LENGTH: 51
<212> TYPE: PRT
<213> ORGANISM: Homo sapiens

<400> SEQUENCE: 5

Cys Leu Val Ser Lys Val Val Gly Arg Cys Arg Ala Ser Met Pro Arg
1               5                   10                  15

Trp Trp Tyr Asn Val Thr Asp Gly Ser Cys Gln Leu Phe Val Tyr Gly
            20                  25                  30

Gly Cys Asp Gly Asn Ser Asn Asn Tyr Leu Thr Lys Glu Glu Cys Leu
        35                  40                  45

Lys Lys Cys
    50
```

<210> SEQ ID NO 6
<211> LENGTH: 58
<212> TYPE: PRT
<213> ORGANISM: Homo sapiens

<400> SEQUENCE: 6

Tyr Glu Glu Tyr Cys Thr Ala Asn Ala Val Thr Gly Pro Cys Arg Ala
1               5                   10                  15

Ser Phe Pro Arg Trp Tyr Phe Asp Val Glu Arg Asn Ser Cys Asn Asn
            20                  25                  30

Phe Ile Tyr Gly Gly Cys Arg Gly Asn Lys Asn Ser Tyr Arg Ser Glu
        35                  40                  45

Glu Ala Cys Met Leu Arg Cys Phe Arg Gln
    50                  55

<210> SEQ ID NO 7
<211> LENGTH: 51
<212> TYPE: PRT
<213> ORGANISM: Homo sapiens

<400> SEQUENCE: 7

Cys Thr Ala Asn Ala Val Thr Gly Pro Cys Arg Ala Ser Phe Pro Arg
1               5                   10                  15

Trp Tyr Phe Asp Val Glu Arg Asn Ser Cys Asn Asn Phe Ile Tyr Gly
            20                  25                  30

Gly Cys Arg Gly Asn Lys Asn Ser Tyr Arg Ser Glu Glu Ala Cys Met
        35                  40                  45

Leu Arg Cys
    50

<210> SEQ ID NO 8
<211> LENGTH: 92
<212> TYPE: PRT
<213> ORGANISM: Homo sapiens

<400> SEQUENCE: 8

Ala Asp Arg Glu Arg Ser Ile His Asp Phe Cys Leu Val Ser Lys Val
1               5                   10                  15

Val Gly Arg Cys Arg Ala Ser Met Pro Arg Trp Trp Tyr Asn Val Thr
            20                  25                  30

Asp Gly Ser Cys Gln Leu Phe Val Tyr Gly Gly Cys Asp Gly Asn Ser
        35                  40                  45

Asn Asn Tyr Leu Thr Lys Glu Glu Cys Leu Lys Lys Cys Ala Thr Val
    50                  55                  60

Thr Glu Asn Ala Thr Gly Asp Leu Ala Thr Ser Arg Asn Ala Ala Asp
65                  70                  75                  80

Ser Ser Val Pro Ser Ala Pro Arg Arg Gln Asp Ser
            85                  90

<210> SEQ ID NO 9
<211> LENGTH: 708
<212> TYPE: DNA
<213> ORGANISM: Artificial Sequence
<220> FEATURE:
<223> OTHER INFORMATION: Consensus DNA sequence of human Bikunin
      (Fig. 3).
<220> FEATURE:
<221> NAME/KEY: misc_feature
<222> LOCATION: (679)..(679)
<223> OTHER INFORMATION: "n" is any nucleotide.
<220> FEATURE:

<221> NAME/KEY: misc_feature
<222> LOCATION: (707)..(707)
<223> OTHER INFORMATION: "n" is any nucleotide.

<400> SEQUENCE: 9

```
ggccgggtcg tttctcgcct ggctgggatc gctgctcctc tctgggtcc tggcggccga     60
ccgagaacgc agcatccacg acttctgcct ggtgtcgaag gtggtgggca gatgccgggc    120
ctccatgcct aggtggtggt acaatgtcac tgacggatcc tgccagctgt ttgtgtatgg    180
gggctgtgac ggaaacagca ataattacct gaccaaggag gagtgcctca agaaatgtgc    240
cactgtcaca gagaatgcca cgggtgacct ggccaccagc aggaatgcag cggattcctc    300
tgtcccaagt gctcccagaa ggcaggattc tgaagaccac tccagcgata tgttcaacta    360
tgaagaatac tgcaccgcca acgcagtcac tgggccttgc cgtgcatcct tcccacgctg    420
gtactttgac gtggagagga actcctgcaa taacttcatc tatggaggct gccggggcaa    480
taagaacagc taccgctctg aggaggcctg catgctccgc tgcttccgcc agcaggagaa    540
tcctcccctg ccccttggct caaaggtggt ggttctggcc ggggctgttt cgtgatggtg    600
ttgatccttt tcctggggag catccatggt cttactgatt ccgggtggca aggaggaacc    660
aggagcgtgc cctgcgganc gtctggagct tcggagatga caagggnt               708
```

<210> SEQ ID NO 10
<211> LENGTH: 197
<212> TYPE: PRT
<213> ORGANISM: Artificial Sequence
<220> FEATURE:
<223> OTHER INFORMATION: Amino acids -18 to 179 of translation of
      consensus sequence in Fig. 3.

<400> SEQUENCE: 10

```
Ala Gly Ser Phe Leu Ala Trp Leu Gly Ser Leu Leu Ser Gly Val
1               5                   10                  15

Leu Ala Ala Asp Arg Glu Arg Ser Ile His Asp Phe Cys Leu Val Ser
                20                  25                  30

Lys Val Val Gly Arg Cys Arg Ala Ser Met Pro Arg Trp Trp Tyr Asn
            35                  40                  45

Val Thr Asp Gly Ser Cys Gln Leu Phe Val Tyr Gly Gly Cys Asp Gly
        50                  55                  60

Asn Ser Asn Asn Tyr Leu Thr Lys Glu Glu Cys Leu Lys Lys Cys Ala
65                  70                  75                  80

Thr Val Thr Glu Asn Ala Thr Gly Asp Leu Ala Thr Ser Arg Asn Ala
                85                  90                  95

Ala Asp Ser Ser Val Pro Ser Ala Pro Arg Arg Gln Asp Ser Glu Asp
            100                 105                 110

His Ser Ser Asp Met Phe Asn Tyr Glu Glu Tyr Cys Thr Ala Asn Ala
        115                 120                 125

Val Thr Gly Pro Cys Arg Ala Ser Phe Pro Arg Trp Tyr Phe Asp Val
    130                 135                 140

Glu Arg Asn Ser Cys Asn Asn Phe Ile Tyr Gly Gly Cys Arg Gly Asn
145                 150                 155                 160

Lys Asn Ser Tyr Arg Ser Glu Glu Ala Cys Met Leu Arg Cys Phe Arg
                165                 170                 175

Gln Gln Glu Asn Pro Pro Leu Pro Leu Gly Ser Lys Val Val Val Leu
            180                 185                 190

Ala Gly Ala Val Ser
        195
```

<210> SEQ ID NO 11
<211> LENGTH: 179
<212> TYPE: PRT
<213> ORGANISM: Artificial Sequence
<220> FEATURE:
<223> OTHER INFORMATION: Variants of human Bikunin.
<220> FEATURE:
<221> NAME/KEY: MISC_FEATURE
<222> LOCATION: (8)..(8)
<223> OTHER INFORMATION: Each "Xaa" independently represents a naturally occurring amino acid residue except Cys, with the proviso that at least one "Xaa" in SEQ ID NO:11 is different from the corresponding amino acid residue of the native sequence (see page 10 of specification).
<220> FEATURE:
<221> NAME/KEY: MISC_FEATURE
<222> LOCATION: (17)..(17)
<223> OTHER INFORMATION: Each "Xaa" independently represents a naturally occurring amino acid residue except Cys, with the proviso that at least one "Xaa" in SEQ ID NO:11 is different from the corresponding amino acid residue of the native sequence (see page 10 of specification).
<220> FEATURE:
<221> NAME/KEY: MISC_FEATURE
<222> LOCATION: (19)..(19)
<223> OTHER INFORMATION: Each "Xaa" independently represents a naturally occurring amino acid residue except Cys, with the proviso that at least one "Xaa" in SEQ ID NO:11 is different from the corresponding amino acid residue of the native sequence (see page 10 of specification).
<220> FEATURE:
<221> NAME/KEY: MISC_FEATURE
<222> LOCATION: (21)..(26)
<223> OTHER INFORMATION: Each "Xaa" independently represents a naturally occurring amino acid residue except Cys, with the proviso that at least one "Xaa" in SEQ ID NO:11 is different from the corresponding amino acid residue of the native sequence (see page 10 of specification).
<220> FEATURE:
<221> NAME/KEY: MISC_FEATURE
<222> LOCATION: (40)..(40)
<223> OTHER INFORMATION: Each "Xaa" independently represents a naturally occurring amino acid residue except Cys, with the proviso that at least one "Xaa" in SEQ ID NO:11 is different from the corresponding amino acid residue of the native sequence (see page 10 of specification).
<220> FEATURE:
<221> NAME/KEY: MISC_FEATURE
<222> LOCATION: (42)..(42)
<223> OTHER INFORMATION: Each "Xaa" independently represents a naturally occurring amino acid residue except Cys, with the proviso that at least one "Xaa" in SEQ ID NO:11 is different from the corresponding amino acid residue of the native sequence (see page 10 of specification).
<220> FEATURE:
<221> NAME/KEY: MISC_FEATURE
<222> LOCATION: (45)..(47)
<223> OTHER INFORMATION: Each "Xaa" independently represents a naturally occurring amino acid residue except Cys, with the proviso that at least one "Xaa" in SEQ ID NO:11 is different from the corresponding amino acid residue of the native sequence (see page 10 of specification).
<220> FEATURE:
<221> NAME/KEY: MISC_FEATURE
<222> LOCATION: (52)..(52)
<223> OTHER INFORMATION: Each "Xaa" independently represents a naturally occurring amino acid residue except Cys, with the proviso that at least one "Xaa" in SEQ ID NO:11 is different from the corresponding amino acid residue of the native sequence (see page 10 of specification).
<220> FEATURE:
<221> NAME/KEY: MISC_FEATURE
<222> LOCATION: (64)..(64)
<223> OTHER INFORMATION: Each "Xaa" independently represents a naturally occurring amino acid residue except Cys, with the proviso that at least one "Xaa" in SEQ ID NO:11 is different from the corresponding amino acid residue of the native sequence (see page

```
       10 of specification).
<220> FEATURE:
<221> NAME/KEY: MISC_FEATURE
<222> LOCATION: (103)..(103)
<223> OTHER INFORMATION: Each "Xaa" independently represents a naturally
      occurring amino acid residue except Cys, with the proviso that at
      least one "Xaa" in SEQ ID NO:11 is different from the
      corresponding amino acid residue of the native sequence (see page
      10 of specification).
<220> FEATURE:
<221> NAME/KEY: MISC_FEATURE
<222> LOCATION: (112)..(112)
<223> OTHER INFORMATION: Each "Xaa" independently represents a naturally
      occurring amino acid residue except Cys, with the proviso that at
      least one "Xaa" in SEQ ID NO:11 is different from the
      corresponding amino acid residue of the native sequence (see page
      10 of specification).
<220> FEATURE:
<221> NAME/KEY: MISC_FEATURE
<222> LOCATION: (114)..(114)
<223> OTHER INFORMATION: Each "Xaa" independently represents a naturally
      occurring amino acid residue except Cys, with the proviso that at
      least one "Xaa" in SEQ ID NO:11 is different from the
      corresponding amino acid residue of the native sequence (see page
      10 of specification).
<220> FEATURE:
<221> NAME/KEY: MISC_FEATURE
<222> LOCATION: (116)..(121)
<223> OTHER INFORMATION: Each "Xaa" independently represents a naturally
      occurring amino acid residue except Cys, with the proviso that at
      least one "Xaa" in SEQ ID NO:11 is different from the
      corresponding amino acid residue of the native sequence (see page
      10 of specification).
<220> FEATURE:
<221> NAME/KEY: MISC_FEATURE
<222> LOCATION: (135)..(135)
<223> OTHER INFORMATION: Each "Xaa" independently represents a naturally
      occurring amino acid residue except Cys, with the proviso that at
      least one "Xaa" in SEQ ID NO:11 is different from the
      corresponding amino acid residue of the native sequence (see page
      10 of specification).
<220> FEATURE:
<221> NAME/KEY: MISC_FEATURE
<222> LOCATION: (137)..(137)
<223> OTHER INFORMATION: Each "Xaa" independently represents a naturally
      occurring amino acid residue except Cys, with the proviso that at
      least one "Xaa" in SEQ ID NO:11 is different from the
      corresponding amino acid residue of the native sequence (see page
      10 of specification).
<220> FEATURE:
<221> NAME/KEY: MISC_FEATURE
<222> LOCATION: (140)..(142)
<223> OTHER INFORMATION: Each "Xaa" independently represents a naturally
      occurring amino acid residue except Cys, with the proviso that at
      least one "Xaa" in SEQ ID NO:11 is different from the
      corresponding amino acid residue of the native sequence (see page
      10 of specification).
<220> FEATURE:
<221> NAME/KEY: MISC_FEATURE
<222> LOCATION: (147)..(147)
<223> OTHER INFORMATION: Each "Xaa" independently represents a naturally
      occurring amino acid residue except Cys, with the proviso that at
      least one "Xaa" in SEQ ID NO:11 is different from the
      corresponding amino acid residue of the native sequence (see page
      10 of specification).
<220> FEATURE:
<221> NAME/KEY: MISC_FEATURE
<222> LOCATION: (159)..(159)
<223> OTHER INFORMATION: Each "Xaa" independently represents a naturally
      occurring amino acid residue except Cys, with the proviso that at
      least one "Xaa" in SEQ ID NO:11 is different from the
      corresponding amino acid residue of the native sequence (see page
      10 of specification).

<400> SEQUENCE: 11

Ala Asp Arg Glu Arg Ser Ile Xaa Asp Phe Cys Leu Val Ser Lys Val
1               5                   10                  15
```

Xaa Gly Xaa Cys Xaa Xaa Xaa Xaa Xaa Trp Trp Tyr Asn Val Thr
        20                  25                  30

Asp Gly Ser Cys Gln Leu Phe Xaa Tyr Xaa Gly Cys Xaa Xaa Xaa Ser
 35                      40                  45

Asn Asn Tyr Xaa Thr Lys Glu Glu Cys Leu Lys Lys Cys Ala Thr Xaa
 50                      55                  60

Thr Glu Asn Ala Thr Gly Asp Leu Ser Thr Ser Arg Asn Ala Ala Asp
65                   70                  75                  80

Ser Ser Val Pro Ser Ala Pro Arg Arg Gln Asp Ser Glu His Asp Ser
             85                  90                  95

Ser Asp Met Phe Asn Tyr Xaa Glu Tyr Cys Thr Ala Asn Ala Val Xaa
            100                 105                 110

Gly Xaa Cys Xaa Xaa Xaa Xaa Xaa Xaa Trp Tyr Phe Asp Val Glu Arg
        115                 120                 125

Asn Ser Cys Asn Asn Phe Xaa Tyr Xaa Gly Cys Xaa Xaa Xaa Lys Asn
130                 135                 140

Ser Tyr Xaa Ser Glu Glu Ala Cys Met Leu Arg Cys Phe Arg Xaa Gln
145             150                 155                 160

Glu Asn Pro Pro Leu Pro Leu Gly Ser Lys Val Val Val Leu Ala Gly
                165                 170                 175

Ala Val Ser

<210> SEQ ID NO 12
<211> LENGTH: 393
<212> TYPE: DNA
<213> ORGANISM: Homo sapiens
<220> FEATURE:
<221> NAME/KEY: misc_feature
<222> LOCATION: (361)..(361)
<223> OTHER INFORMATION: "n" is any nucleotide.
<220> FEATURE:
<221> NAME/KEY: misc_feature
<222> LOCATION: (367)..(367)
<223> OTHER INFORMATION: "n" is any nucleotide.
<220> FEATURE:
<221> NAME/KEY: misc_feature
<222> LOCATION: (384)..(384)
<223> OTHER INFORMATION: "n" is any nucleotide.
<220> FEATURE:
<221> NAME/KEY: misc_feature
<222> LOCATION: (390)..(390)
<223> OTHER INFORMATION: "n" is any nucleotide.

<400> SEQUENCE: 12
ggccgggtcg tttctcgcct ggctgggatc gctgctcctc tctggggtcc tggccggccg      60
accgagaacg cagcatccac gacttctgcc tggtgtcgaa ggtggtgggc agattccggg     120
cctccatgcc taggtggtgg tacaatgtca ctgacggatc ctgccagctg tttgtgtatg     180
ggggctgtga cggaaacagc aataattacc tgaccaagga ggagtgcctc aagaaatgtg     240
ccactgtcac agagaatgcc acgggtgacc tggccaccag caggaatgca gcggattcct     300
ctgtcccaag tgctcccaga aggcaggatt cttgaagacc acttcagcga tatgtttcaa     360
ntattgnaag aataattgca ccgncaacgn att                                  393

<210> SEQ ID NO 13
<211> LENGTH: 110
<212> TYPE: PRT
<213> ORGANISM: Homo sapiens
<220> FEATURE:
<221> NAME/KEY: SIGNAL
<222> LOCATION: (1)..(18)
<223> OTHER INFORMATION:

<400> SEQUENCE: 13

```
Pro Gly Arg Phe Ser Pro Gly Trp Asp Arg Cys Ser Ser Leu Gly Ser
1               5                  10                  15
Trp Pro Ala Asp Arg Glu Arg Ser Ile His Asp Phe Cys Leu Val Ser
            20                  25                  30
Lys Val Val Gly Arg Glu Arg Ala Ser Met Pro Arg Trp Trp Tyr Asn
        35                  40                  45
Val Thr Asp Gly Ser Cys Gln Leu Phe Val Tyr Gly Gly Cys Asp Gly
    50                  55                  60
Asn Ser Asn Asn Tyr Leu Thr Lys Glu Glu Cys Leu Lys Lys Cys Ala
65                  70                  75                  80
Thr Val Thr Glu Asn Ala Thr Gly Asp Leu Ala Thr Ser Arg Asn Ala
                85                  90                  95
Ala Asp Ser Ser Val Pro Ser Ala Pro Arg Arg Gln Asp Ser
            100                 105                 110
```

<210> SEQ ID NO 14
<211> LENGTH: 510
<212> TYPE: DNA
<213> ORGANISM: Homo sapiens
<220> FEATURE:
<221> NAME/KEY: misc_feature
<222> LOCATION: (424)..(424)
<223> OTHER INFORMATION: "n" is any nucleotide.
<220> FEATURE:
<221> NAME/KEY: misc_feature
<222> LOCATION: (481)..(481)
<223> OTHER INFORMATION: "n" is any nucleotide.
<220> FEATURE:
<221> NAME/KEY: misc_feature
<222> LOCATION: (509)..(509)
<223> OTHER INFORMATION: "n" is any nucleotide.

<400> SEQUENCE: 14

```
gcaataatta cctgaccaag gaggagtgcc tcaagaaatg tgccactgtc acagagaatg      60
ccacgggtga cctggccacc agcaggaatg cagcggattc ctctgtccca agtctcccag     120
aaggcaggat tctgaagacc actccagcga tatgttcaac tatgaagaat actgcaccgc     180
caacgcagtc actgggcctt gccgtgcatc cttcccacgc tggtactttg acgtggagag     240
gaactcctgc aataacttca tctatggagg ctgccggggc aataagaaca gctaccgctc     300
tgaggaggcc tgcatgctcc gctgcttccg ccagcaggag aatcctcccc tgccccttgg     360
ctcaaaggtg gtggttctgg ccggggctgt tcgtgatgg tgttgatcct tttcctgggg     420
agcntccatg gtcttactga ttccgggtgg caaggaggaa ccaggagcgt gccctgcgga     480
ncgtctggag cttcggagat gacaagggnt                                      510
```

<210> SEQ ID NO 15
<211> LENGTH: 20
<212> TYPE: PRT
<213> ORGANISM: Homo sapiens

<400> SEQUENCE: 15

```
Leu Pro Asp Gln Gly Gly Val Pro Gln Glu Met Cys His Cys His Arg
1               5                  10                  15
Glu Cys His Gly
            20
```

<210> SEQ ID NO 16
<211> LENGTH: 428

```
<212> TYPE: DNA
<213> ORGANISM: Homo sapiens
<220> FEATURE:
<221> NAME/KEY: misc_feature
<222> LOCATION: (3)..(3)
<223> OTHER INFORMATION: "n" is any nucleotide.
<220> FEATURE:
<221> NAME/KEY: misc_feature
<222> LOCATION: (11)..(12)
<223> OTHER INFORMATION: "n" is any nucleotide.
<220> FEATURE:
<221> NAME/KEY: misc_feature
<222> LOCATION: (17)..(17)
<223> OTHER INFORMATION: "n" is any nucleotide.
<220> FEATURE:
<221> NAME/KEY: misc_feature
<222> LOCATION: (48)..(48)
<223> OTHER INFORMATION: "n" is any nucleotide.
<220> FEATURE:
<221> NAME/KEY: misc_feature
<222> LOCATION: (425)..(425)
<223> OTHER INFORMATION: "n" is any nucleotide.

<400> SEQUENCE: 16
gcngcgcgtt nntcgcntgc tgggatcgct gcacctctct ggggtcgngg cggccgaccg      60
agaacgcagc atccacgact tctgcctggt gtcgaaggtg gtgggcagat gccgggcctc     120
catgcctagg tggtggtaca atgtcactga cggatcctgc cagctgtttg tgtatggggg     180
ctgtgacgga acagcaata attacctgac caaggaggag tgcctcaaga aatgtgccac     240
tgtcacagag aatgccacgg gtgacctggc caccagcagg aatgcagcgg attcctctgt     300
cccaagtgct cccagaaggc aggattctga agaccactcc agcgatatgt tcaactatga     360
agaatactgg caccgccaac gcattcactg ggcctgcgtg catccttccc acgctggtac     420 tttgncgt                                                             428

<210> SEQ ID NO 17
<211> LENGTH: 425
<212> TYPE: DNA
<213> ORGANISM: Homo sapiens
<220> FEATURE:
<221> NAME/KEY: misc_feature
<222> LOCATION: (7)..(7)
<223> OTHER INFORMATION: "n" is any nucleotide.
<220> FEATURE:
<221> NAME/KEY: misc_feature
<222> LOCATION: (403)..(403)
<223> OTHER INFORMATION: "n" is any nucleotide.
<220> FEATURE:
<221> NAME/KEY: misc_feature
<222> LOCATION: (409)..(409)
<223> OTHER INFORMATION: "n" is any nucleotide.

<400> SEQUENCE: 17
ctgggantcg ctgctcctct ctggggtcct ggcggccgac cgagaacgca gcatccacga      60
cttctgcctg gtgtcgaagg tggtgggcag atgccgggcc tccatgccta ggtggtggta     120
caatgtcact gacggatcct gccagctgtt tgtgtatggg ggctgtgacg gaaacagcaa     180
taattacctg accaaggagg agtgcctcaa gaaatgtgcc actgtcacag agaatgccac     240
gggtgacctg gccaccagca ggaatgcagc ggattcctct gtcccaagtg ctcccagaag     300
gcaggattct gaagaccact ccagcgatat gttcaactat gaagaatact gcaccgccaa     360
cgcagtcact ggggccttgc gtggaatcct ttcccacgct ggnaatttng acgttgagaa     420
ggaac                                                                425

<210> SEQ ID NO 18
```

-continued

```
<211> LENGTH: 57
<212> TYPE: PRT
<213> ORGANISM: Unknown
<220> FEATURE:
<223> OTHER INFORMATION: Kunitz-like domain of tissue factor pathway
      inhibitor precursor 1.

<400> SEQUENCE: 18

His Ser Phe Cys Ala Phe Lys Ala Asp Asp Gly Pro Cys Lys Ala Ile
1               5                   10                  15

Met Lys Arg Phe Phe Phe Asn Ile Phe Thr Arg Gln Cys Glu Glu Phe
            20                  25                  30

Ile Tyr Gly Gly Cys Glu Gly Asn Gln Asn Arg Phe Glu Ser Leu Glu
        35                  40                  45

Glu Cys Lys Lys Met Cys Thr Arg Asp
    50                  55

<210> SEQ ID NO 19
<211> LENGTH: 57
<212> TYPE: PRT
<213> ORGANISM: Unknown
<220> FEATURE:
<223> OTHER INFORMATION: Kunitz-like domain of tissue factor pathway
      inhibitor precursor 1.

<400> SEQUENCE: 19

Pro Asp Phe Cys Phe Leu Glu Glu Asp Pro Gly Ile Cys Arg Gly Tyr
1               5                   10                  15

Ile Thr Arg Tyr Phe Tyr Asn Asn Gln Thr Lys Gln Cys Glu Arg Phe
            20                  25                  30

Lys Tyr Gly Gly Cys Leu Gly Asn Met Asn Asn Phe Glu Thr Leu Glu
        35                  40                  45

Glu Cys Lys Asn Ile Cys Glu Asp Gly
    50                  55

<210> SEQ ID NO 20
<211> LENGTH: 57
<212> TYPE: PRT
<213> ORGANISM: Unknown
<220> FEATURE:
<223> OTHER INFORMATION: Kunitz-like domain of tissue factor pathway
      inhibitor precursor.

<400> SEQUENCE: 20

Pro Ser Trp Cys Leu Thr Pro Ala Asp Arg Gly Leu Cys Arg Ala Asn
1               5                   10                  15

Glu Asn Arg Phe Tyr Tyr Asn Ser Val Ile Gly Lys Cys Arg Pro Phe
            20                  25                  30

Lys Tyr Ser Gly Cys Gly Asn Glu Asn Asn Phe Thr Ser Lys Gln
        35                  40                  45

Glu Cys Leu Arg Ala Cys Lys Lys Gly
    50                  55

<210> SEQ ID NO 21
<211> LENGTH: 57
<212> TYPE: PRT
<213> ORGANISM: Unknown
<220> FEATURE:
<223> OTHER INFORMATION: Kunitz-like domain of tissue factor pathway
      inhibitor precursor 2.

<400> SEQUENCE: 21

Ala Glu Ile Cys Leu Leu Pro Leu Asp Tyr Gly Pro Cys Arg Ala Leu
```

```
                1               5              10              15

Leu Leu Arg Tyr Tyr Arg Tyr Arg Thr Gln Ser Cys Arg Gln Phe
                    20              25              30

Leu Tyr Gly Gly Cys Glu Gly Asn Ala Asn Asn Phe Tyr Thr Trp Glu
            35              40              45

Ala Cys Asp Asp Ala Cys Trp Arg Ile
        50              55
```

<210> SEQ ID NO 22
<211> LENGTH: 57
<212> TYPE: PRT
<213> ORGANISM: Unknown
<220> FEATURE:
<223> OTHER INFORMATION: Kunitz-like domain of tissue factor pathway
      inhibitor precursor 2.

<400> SEQUENCE: 22

```
Pro Ser Phe Cys Tyr Ser Pro Lys Asp Glu Gly Leu Cys Ser Ala Asn
1               5              10              15

Val Thr Arg Tyr Tyr Phe Asn Pro Arg Tyr Arg Thr Cys Asp Ala Phe
                20              25              30

Thr Tyr Thr Gly Cys Gly Asn Asn Asp Asn Asn Phe Val Ser Arg Glu
            35              40              45

Asp Ser Lys Arg Ala Cys Ala Lys Ala
        50              55
```

<210> SEQ ID NO 23
<211> LENGTH: 57
<212> TYPE: PRT
<213> ORGANISM: Unknown
<220> FEATURE:
<223> OTHER INFORMATION: Kunitz-like domain of amyloid precursor protein
      homologue.

<400> SEQUENCE: 23

```
Lys Ala Val Cys Ser Gln Glu Ala Met Thr Gly Pro Cys Arg Ala Val
1               5              10              15

Met Pro Arg Thr Thr Phe Asp Leu Ser Lys Gly Lys Cys Val Arg Phe
                20              25              30

Ile Thr Gly Gly Cys Gly Gly Asn Arg Asn Asn Phe Glu Ser Glu Asp
            35              40              45

Tyr Cys Met Ala Val Cys Lys Ala Met
        50              55
```

<210> SEQ ID NO 24
<211> LENGTH: 58
<212> TYPE: PRT
<213> ORGANISM: Unknown
<220> FEATURE:
<223> OTHER INFORMATION: Kunitz-like domain of aprotinin.

<400> SEQUENCE: 24

```
Arg Pro Asp Phe Cys Leu Glu Pro Pro Tyr Thr Gly Pro Cys Lys Ala
1               5              10              15

Arg Ile Ile Arg Tyr Phe Tyr Asn Ala Lys Ala Gly Leu Cys Gln Thr
                20              25              30

Phe Val Tyr Gly Gly Cys Arg Ala Lys Arg Asn Asn Phe Lys Ser Ala
            35              40              45

Glu Asp Cys Met Arg Thr Cys Gly Gly Ala
        50              55
```

<210> SEQ ID NO 25
<211> LENGTH: 51
<212> TYPE: PRT
<213> ORGANISM: Unknown
<220> FEATURE:
<223> OTHER INFORMATION: Kunitz-like domain of inter-alpha-trypsin
      inhibitor precursor.

<400> SEQUENCE: 25

Cys Gln Leu Gly Tyr Ser Ala Gly Pro Cys Met Gly Met Thr Ser Arg
1               5                   10                  15

Tyr Phe Tyr Asn Gly Thr Ser Met Ala Cys Glu Thr Phe Gln Tyr Gly
            20                  25                  30

Gly Cys Met Gly Asn Gly Asn Asn Phe Val Thr Glu Lys Glu Cys Leu
        35                  40                  45

Gln Thr Cys
    50

<210> SEQ ID NO 26
<211> LENGTH: 57
<212> TYPE: PRT
<213> ORGANISM: Unknown
<220> FEATURE:
<223> OTHER INFORMATION: Kunitz-like domain of inter-alpha-trypsin
      inhibitor precursor.

<400> SEQUENCE: 26

Val Ala Ala Cys Asn Leu Pro Ile Val Arg Gly Pro Cys Arg Ala Phe
1               5                   10                  15

Ile Gln Leu Trp Ala Phe Asp Ala Val Lys Gly Lys Cys Val Leu Phe
            20                  25                  30

Pro Tyr Gly Gly Cys Gln Gly Asn Gly Asn Lys Phe Tyr Ser Glu Lys
        35                  40                  45

Glu Cys Arg Glu Tyr Cys Gly Val Pro
    50                  55

<210> SEQ ID NO 27
<211> LENGTH: 57
<212> TYPE: PRT
<213> ORGANISM: Unknown
<220> FEATURE:
<223> OTHER INFORMATION: Kunitz-like domain of amyloid precursor
      protein.

<400> SEQUENCE: 27

Glu Val Cys Cys Ser Glu Gln Ala Glu Thr Gly Pro Cys Arg Ala Met
1               5                   10                  15

Ile Ser Arg Trp Tyr Phe Asp Val Thr Glu Gly Lys Cys Ala Pro Phe
            20                  25                  30

Phe Tyr Gly Gly Cys Gly Gly Asn Arg Asn Asn Phe Asp Thr Glu Glu
        35                  40                  45

Tyr Cys Met Ala Val Cys Gly Ser Ala
    50                  55

<210> SEQ ID NO 28
<211> LENGTH: 51
<212> TYPE: PRT
<213> ORGANISM: Unknown
<220> FEATURE:
<223> OTHER INFORMATION: Kunitz-like domain of collagen alpha-3(VI)
      precursor.

<400> SEQUENCE: 28

```
Cys Lys Leu Pro Lys Asp Glu Gly Thr Cys Arg Asp Phe Ile Leu Lys
1               5                   10                  15

Trp Tyr Tyr Asp Pro Asn Thr Lys Ser Cys Ala Arg Phe Trp Tyr Gly
            20                  25                  30

Gly Cys Gly Gly Asn Glu Asn Lys Phe Gly Ser Gln Lys Glu Cys Glu
        35                  40                  45

Lys Val Cys
    50

<210> SEQ ID NO 29
<211> LENGTH: 57
<212> TYPE: PRT
<213> ORGANISM: Unknown
<220> FEATURE:
<223> OTHER INFORMATION: Kunitz-like domain of HKI-B9.

<400> SEQUENCE: 29

Pro Asn Val Cys Ala Phe Pro Met Glu Lys Gly Pro Cys Gln Thr Tyr
1               5                   10                  15

Met Thr Arg Trp Phe Phe Asn Phe Glu Thr Gly Glu Cys Glu Leu Phe
            20                  25                  30

Ala Tyr Gly Gly Cys Gly Gly Asn Ser Asn Asn Phe Leu Arg Lys Glu
        35                  40                  45

Lys Cys Glu Lys Phe Cys Lys Phe Thr
    50                  55

<210> SEQ ID NO 30
<211> LENGTH: 46
<212> TYPE: DNA
<213> ORGANISM: Artificial Sequence
<220> FEATURE:
<223> OTHER INFORMATION: 5' sense oligonucleotide used in Example 6.

<400> SEQUENCE: 30
gccaagcttg gataaaagat atgaagaata ctgcaccgcc aacgca                46

<210> SEQ ID NO 31
<211> LENGTH: 35
<212> TYPE: DNA
<213> ORGANISM: Artificial Sequence
<220> FEATURE:
<223> OTHER INFORMATION: 3' antisense oligonucleotide used in Example 6.

<400> SEQUENCE: 31
ggggatcctc actgctggcg gaagcagcgg agcat                            35

<210> SEQ ID NO 32
<211> LENGTH: 206
<212> TYPE: DNA
<213> ORGANISM: Artificial Sequence
<220> FEATURE:
<223> OTHER INFORMATION: Cloned bikunin cDNA fragment in Example 6.

<400> SEQUENCE: 32
ccaagcttgg ataaaagata tgaagaatac tgcaccgcca acgcagtcac tgggccttgc    60
cgtgcatcct tcccacgctg gtactttgac gtggagagga actcctgcaa taacttcatc   120
tatggaggct gccggggcaa taagaacagc taccgctctg aggaggcctg catgctccgc   180
tgcttccgcc agcagtgagg atcccc                                       206

<210> SEQ ID NO 33
```

```
<211> LENGTH: 28
<212> TYPE: DNA
<213> ORGANISM: Artificial Sequence
<220> FEATURE:
<223> OTHER INFORMATION: 3' PCR primer used to amplify EST R74593.

<400> SEQUENCE: 33
cgaagcttca tctccgaagc tccagacg                                    28

<210> SEQ ID NO 34
<211> LENGTH: 31
<212> TYPE: DNA
<213> ORGANISM: Artificial Sequence
<220> FEATURE:
<223> OTHER INFORMATION: 5' PCR primer used to amplify EST R74593.

<400> SEQUENCE: 34
aggatctaga caataattac ctgaccaagg a                                31

<210> SEQ ID NO 35
<211> LENGTH: 37
<212> TYPE: DNA
<213> ORGANISM: Artificial Sequence
<220> FEATURE:
<223> OTHER INFORMATION: 5' PCR primer used to amplify EST R35464.

<400> SEQUENCE: 35
ggtctagagg ccgggtccgt ttctcgcctg gctggga                          37

<210> SEQ ID NO 36
<211> LENGTH: 19
<212> TYPE: DNA
<213> ORGANISM: Artificial Sequence
<220> FEATURE:
<223> OTHER INFORMATION: 5' PCR primer used to amplify EST R34808.

<400> SEQUENCE: 36
cacctgatcg cgagacccc                                              19

<210> SEQ ID NO 37
<211> LENGTH: 19
<212> TYPE: DNA
<213> ORGANISM: Artificial Sequence
<220> FEATURE:
<223> OTHER INFORMATION: Vector specific DNA sequencing primer (SP6).

<400> SEQUENCE: 37
gatttaggtg acactatag                                              19

<210> SEQ ID NO 38
<211> LENGTH: 20
<212> TYPE: DNA
<213> ORGANISM: Artificial Sequence
<220> FEATURE:
<223> OTHER INFORMATION: Vector specific DNA sequencing primer (T7).

<400> SEQUENCE: 38
taatacgact cactataggg                                             20

<210> SEQ ID NO 39
<211> LENGTH: 22
<212> TYPE: DNA
<213> ORGANISM: Artificial Sequence
<220> FEATURE:
<223> OTHER INFORMATION: Gene specific DNA sequencing primer.

<400> SEQUENCE: 39
```

-continued ttacctgacc aaggaggagt gc                                              22

<210> SEQ ID NO 40
<211> LENGTH: 23
<212> TYPE: DNA
<213> ORGANISM: Artificial Sequence
<220> FEATURE:
<223> OTHER INFORMATION: Gene specific DNA sequencing primer.

<400> SEQUENCE: 40
aatccgctgc attcctgctg gtg                                             23

<210> SEQ ID NO 41
<211> LENGTH: 20
<212> TYPE: DNA
<213> ORGANISM: Artificial Sequence
<220> FEATURE:
<223> OTHER INFORMATION: Gene specific DNA sequencing primer.

<400> SEQUENCE: 41
cagtcactgg gccttgccgt                                                 20

<210> SEQ ID NO 42
<211> LENGTH: 105
<212> TYPE: DNA
<213> ORGANISM: Artificial Sequence
<220> FEATURE:
<223> OTHER INFORMATION: 5' sense oligonucleotide used in Example 5.

<400> SEQUENCE: 42 gaagggtaa gcttggataa aagatatgaa gaatactgca ccgccaacgc agtcactggg      60
ccttgccgtg catccttccc acgctggtac tttgacgtgg agagg                    105

<210> SEQ ID NO 43
<211> LENGTH: 129
<212> TYPE: DNA
<213> ORGANISM: Artificial Sequence
<220> FEATURE:
<223> OTHER INFORMATION: 3' antisense oligonucleotide used in Example 5.

<400> SEQUENCE: 43
cgcggatccc tactggcgga agcagcggag catgcaggcc tcctcagagc ggtagctgtt     60
cttattgccc cggcagcctc catagatgaa gttattgcag gagttcctct ccacgtcaaa    120
gtaccagcg                                                            129

<210> SEQ ID NO 44
<211> LENGTH: 207
<212> TYPE: DNA
<213> ORGANISM: Artificial Sequence
<220> FEATURE:
<223> OTHER INFORMATION: Cloned bikunin fragment in Example 5.

<400> SEQUENCE: 44 gaagggtaa gcttggataa aagatatgaa gaatactgca ccgccaacgc agtcactggg      60
ccttgccgtg catccttccc acgctggtac tttgacgtgg agaggaactc ctgcaataac    120
ttcatctatg gaggctgccg gggcaataag aacagctacc gctctgagga ggcctgcatg    180
ctccgctgct ccgccagta gggatcc                                         207

<210> SEQ ID NO 45
<211> LENGTH: 248
<212> TYPE: PRT

```
<213> ORGANISM: Artificial Sequence
<220> FEATURE:
<223> OTHER INFORMATION: EST derived consensus sequence of human Bikunin
      (Figs. 4D and 4G).
<220> FEATURE:
<221> NAME/KEY: SIGNAL
<222> LOCATION: (1)..(23)
<223> OTHER INFORMATION:

<400> SEQUENCE: 45

Met Leu Arg Ala Glu Ala Asp Gly Val Ser Arg Leu Leu Gly Ser Leu
1               5                   10                  15

Leu Leu Ser Gly Val Leu Ala Ala Asp Arg Glu Arg Ser Ile His Asp
            20                  25                  30

Phe Cys Leu Val Ser Lys Val Val Gly Arg Cys Arg Ala Ser Met Pro
        35                  40                  45

Arg Trp Trp Tyr Asn Val Thr Asp Gly Ser Cys Gln Leu Phe Val Tyr
    50                  55                  60

Gly Gly Cys Asp Gly Asn Ser Asn Asn Tyr Leu Thr Lys Glu Glu Cys
65                  70                  75                  80

Leu Lys Lys Cys Ala Thr Val Thr Glu Asn Ala Thr Gly Asp Leu Ala
                85                  90                  95

Thr Ser Arg Asn Ala Ala Asp Ser Ser Val Pro Ser Ala Pro Arg Arg
            100                 105                 110

Gln Asp Ser Glu Asp His Ser Ser Asp Met Phe Asn Tyr Glu Glu Tyr
        115                 120                 125

Cys Thr Ala Asn Ala Val Thr Gly Pro Cys Arg Ala Ser Phe Pro Arg
130                 135                 140

Trp Tyr Phe Asp Val Glu Arg Asn Ser Cys Asn Asn Phe Ile Tyr Gly
145                 150                 155                 160

Gly Cys Arg Gly Asn Lys Asn Ser Tyr Arg Ser Glu Glu Ala Cys Met
                165                 170                 175

Leu Arg Cys Phe Arg Gln Gln Glu Asn Pro Pro Leu Pro Leu Gly Ser
            180                 185                 190

Lys Val Val Leu Ala Gly Leu Phe Val Met Val Leu Ile Leu Phe
        195                 200                 205

Leu Gly Ala Ser Met Val Tyr Leu Ile Arg Val Ala Arg Arg Asn Gln
    210                 215                 220

Glu Arg Ala Leu Arg Thr Val Trp Ser Ser Gly Asp Asp Lys Glu Gln
225                 230                 235                 240

Leu Val Lys Asn Thr Tyr Val Leu
                245

<210> SEQ ID NO 46
<211> LENGTH: 782
<212> TYPE: DNA
<213> ORGANISM: Homo sapiens
<220> FEATURE:
<221> NAME/KEY: exon
<222> LOCATION: (61)..(780)
<223> OTHER INFORMATION:

<400> SEQUENCE: 46
acctgatcgc gagaccccaa cggctggtgg cgtcgcctgc gcgtctcggc tgagctggcc      60 atg gcg cag ctg tgc ggg ctg agg cgg agc cgg gcg ttt ctc gcc ctg      108
Met Ala Gln Leu Cys Gly Leu Arg Arg Ser Arg Ala Phe Leu Ala Leu
1               5                   10                  15 ctg gga tcg ctg ctc ctc tct ggg gtc ctg gcg gcc gac cga gaa cgc      156
Leu Gly Ser Leu Leu Leu Ser Gly Val Leu Ala Ala Asp Arg Glu Arg
```

|  |  |  |  |  |  |  |  |  |  |  |  |  |  |  |  |  |
|---|---|---|---|---|---|---|---|---|---|---|---|---|---|---|---|---|
|  |  |  |  | 20 |  |  |  |  | 25 |  |  |  |  | 30 |  |  |

```
agc atc cac gac ttc tgc ctg gtg tcg aag gtg gtg ggc aga tgc cgg      204
Ser Ile His Asp Phe Cys Leu Val Ser Lys Val Val Gly Arg Cys Arg
            35                  40                  45 gcc tcc atg cct agg tgg tgg tac aat gtc act gac gga tcc tgc cag      252
Ala Ser Met Pro Arg Trp Trp Tyr Asn Val Thr Asp Gly Ser Cys Gln
 50                  55                  60 ctg ttt gtg tat ggg ggc tgt gac gga aac agc aat aat tac ctg acc      300
Leu Phe Val Tyr Gly Gly Cys Asp Gly Asn Ser Asn Asn Tyr Leu Thr
 65                  70                  75                  80 aag gag gag tgc ctc aag aaa tgt gcc act gtc aca gag aat gcc acg      348
Lys Glu Glu Cys Leu Lys Lys Cys Ala Thr Val Thr Glu Asn Ala Thr
                85                  90                  95 ggt gac ctg gcc acc agc agg aat gca gcg gat tcc tct gtc cca agt      396
Gly Asp Leu Ala Thr Ser Arg Asn Ala Ala Asp Ser Ser Val Pro Ser
            100                 105                 110 gct ccc aga agg cag gat tct gaa gac cac tcc agc gat atg ttc aac      444
Ala Pro Arg Arg Gln Asp Ser Glu Asp His Ser Ser Asp Met Phe Asn
        115                 120                 125 tat gaa gaa tac tgc acc gcc aac gca gtc act ggg cct tgc cgt gca      492
Tyr Glu Glu Tyr Cys Thr Ala Asn Ala Val Thr Gly Pro Cys Arg Ala
130                 135                 140 tcc ttc cca cgc tgg tac ttt gac gtg gag agg aac tcc tgc aat aac      540
Ser Phe Pro Arg Trp Tyr Phe Asp Val Glu Arg Asn Ser Cys Asn Asn
145                 150                 155                 160 ttc atc tat gga ggc tgc cgg ggc aat aag aac agc tac cgc tct gag      588
Phe Ile Tyr Gly Gly Cys Arg Gly Asn Lys Asn Ser Tyr Arg Ser Glu
                165                 170                 175 gag gcc tgc atg ctc cgc tgc ttc cgc cag cag gag aat cct ccc ctg      636
Glu Ala Cys Met Leu Arg Cys Phe Arg Gln Gln Glu Asn Pro Pro Leu
            180                 185                 190 ccc ctt ggc tca aag gtg gtg gtt ctg gcg ggg ctg ttc gtg atg gtg      684
Pro Leu Gly Ser Lys Val Val Val Leu Ala Gly Leu Phe Val Met Val
        195                 200                 205 ttg atc ctc ttc ctg gga gcc tcc atg gtc tac ctg atc cgg gtg gca      732
Leu Ile Leu Phe Leu Gly Ala Ser Met Val Tyr Leu Ile Arg Val Ala
210                 215                 220 cgg agg aac cag gag cgt gcc ctg cgc acc gtc tgg agc ttc gga gat      780
Arg Arg Asn Gln Glu Arg Ala Leu Arg Thr Val Trp Ser Phe Gly Asp
225                 230                 235                 240 ga                                                                    782
```

<210> SEQ ID NO 47
<211> LENGTH: 240
<212> TYPE: PRT
<213> ORGANISM: Homo sapiens
<220> FEATURE:
<221> NAME/KEY: SIGNAL
<222> LOCATION: (1)..(27)
<223> OTHER INFORMATION:

<400> SEQUENCE: 47

```
Met Ala Gln Leu Cys Gly Leu Arg Arg Ser Arg Ala Phe Leu Ala Leu
 1               5                  10                  15

Leu Gly Ser Leu Leu Leu Ser Gly Val Leu Ala Ala Asp Arg Glu Arg
            20                  25                  30

Ser Ile His Asp Phe Cys Leu Val Ser Lys Val Val Gly Arg Cys Arg
        35                  40                  45

Ala Ser Met Pro Arg Trp Trp Tyr Asn Val Thr Asp Gly Ser Cys Gln
 50                  55                  60
```

```
Leu Phe Val Tyr Gly Gly Cys Asp Gly Asn Ser Asn Asn Tyr Leu Thr
 65                  70                  75                  80

Lys Glu Glu Cys Leu Lys Lys Cys Ala Thr Val Thr Glu Asn Ala Thr
                 85                  90                  95

Gly Asp Leu Ala Thr Ser Arg Asn Ala Ala Asp Ser Ser Val Pro Ser
            100                 105                 110

Ala Pro Arg Arg Gln Asp Ser Glu Asp His Ser Ser Asp Met Phe Asn
        115                 120                 125

Tyr Glu Glu Tyr Cys Thr Ala Asn Ala Val Thr Gly Pro Cys Arg Ala
    130                 135                 140

Ser Phe Pro Arg Trp Tyr Phe Asp Val Glu Arg Asn Ser Cys Asn Asn
145                 150                 155                 160

Phe Ile Tyr Gly Gly Cys Arg Gly Asn Lys Asn Ser Tyr Arg Ser Glu
                165                 170                 175

Glu Ala Cys Met Leu Arg Cys Phe Arg Gln Gln Glu Asn Pro Pro Leu
            180                 185                 190

Pro Leu Gly Ser Lys Val Val Val Leu Ala Gly Leu Phe Val Met Val
        195                 200                 205

Leu Ile Leu Phe Leu Gly Ala Ser Met Val Tyr Leu Ile Arg Val Ala
    210                 215                 220

Arg Arg Asn Gln Glu Arg Ala Leu Arg Thr Val Trp Ser Phe Gly Asp
225                 230                 235                 240

<210> SEQ ID NO 48
<211> LENGTH: 1544
<212> TYPE: DNA
<213> ORGANISM: Homo sapiens
<220> FEATURE:
<221> NAME/KEY: misc_feature
<222> LOCATION: (1358)..(1358)
<223> OTHER INFORMATION: "n" is any nucleotide.
<220> FEATURE:
<221> NAME/KEY: exon
<222> LOCATION: (301)..(1056)
<223> OTHER INFORMATION:

<400> SEQUENCE: 48
gcacgagttg ggaggtgtag cgcggctctg aacgcgctga gggccgttga gtgtcgcagg      60
cggcgagggc gcgagtgagg agcagaccca ggcatcgcgc gccgagaagg ccgggcgtcc     120
ccacactgaa ggtccggaaa ggcgacttcc ggggctttg gcacctggcg gaccctcccg     180
gagcgtcggc acctgaacgc gaggcgctcc attgcgcgtg cgcgttgagg ggcttcccgc     240
acctgatcgc gagaccccaa cggctggtgg cgtcgcctgc gcgtctcggc tgagctggcc     300 atg gcg cag ctg tgc ggg ctg agg cgg agc cgg gcg ttt ctc gcc ctg       348
Met Ala Gln Leu Cys Gly Leu Arg Arg Ser Arg Ala Phe Leu Ala Leu
1               5                   10                  15 ctg gga tcg ctg ctc ctc tct ggg gtc ctg gcg gcc gac cga gaa cgc       396
Leu Gly Ser Leu Leu Leu Ser Gly Val Leu Ala Ala Asp Arg Glu Arg
            20                  25                  30 agc atc cac gac ttc tgc ctg gtg tcg aag gtg gtg ggc aga tgc cgg       444
Ser Ile His Asp Phe Cys Leu Val Ser Lys Val Val Gly Arg Cys Arg
        35                  40                  45 gcc tcc atg cct agg tgg tgg tac aat gtc act gac gga tcc tgc cag       492
Ala Ser Met Pro Arg Trp Trp Tyr Asn Val Thr Asp Gly Ser Cys Gln
    50                  55                  60 ctg ttt gtg tat ggg ggc tgt gac gga aac agc aat aat tac ctg acc       540
Leu Phe Val Tyr Gly Gly Cys Asp Gly Asn Ser Asn Asn Tyr Leu Thr
65                  70                  75                  80
```

```
aag gag gag tgc ctc aag aaa tgt gcc act gtc aca gag aat gcc acg      588
Lys Glu Glu Cys Leu Lys Lys Cys Ala Thr Val Thr Glu Asn Ala Thr
                85                  90                  95 ggt gac ctg gcc acc agc agg aat gca gcg gat tcc tct gtc cca agt      636
Gly Asp Leu Ala Thr Ser Arg Asn Ala Ala Asp Ser Ser Val Pro Ser
            100                 105                 110 gct ccc aga agg cag gat tct gaa gac cac tcc agc gat atg ttc aac      684
Ala Pro Arg Arg Gln Asp Ser Glu Asp His Ser Ser Asp Met Phe Asn
        115                 120                 125 tat gaa gaa tac tgc acc gcc aac gca gtc act ggg cct tgc cgt gca      732
Tyr Glu Glu Tyr Cys Thr Ala Asn Ala Val Thr Gly Pro Cys Arg Ala
    130                 135                 140 tcc ttc cca cgc tgg tac ttt gac gtg gag agg aac tcc tgc aat aac      780
Ser Phe Pro Arg Trp Tyr Phe Asp Val Glu Arg Asn Ser Cys Asn Asn
145                 150                 155                 160 ttc atc tat gga ggc tgc cgg ggc aat aag aac agc tac cgc tct gag      828
Phe Ile Tyr Gly Gly Cys Arg Gly Asn Lys Asn Ser Tyr Arg Ser Glu
                165                 170                 175 gag gcc tgc atg ctc cgc tgc ttc cgc cag cag gag aat cct ccc ctg      876
Glu Ala Cys Met Leu Arg Cys Phe Arg Gln Gln Glu Asn Pro Pro Leu
            180                 185                 190 ccc ctt ggc tca aag gtg gtg gtt ctg gcg ggg ctg ttc gtg atg gtg      924
Pro Leu Gly Ser Lys Val Val Val Leu Ala Gly Leu Phe Val Met Val
        195                 200                 205 ttg atc ctc ttc ctg gga gcc tcc atg gtc tac ctg atc cgg gtg gca      972
Leu Ile Leu Phe Leu Gly Ala Ser Met Val Tyr Leu Ile Arg Val Ala
    210                 215                 220 cgg agg aac cag gag cgt gcc ctg cgc acc gtc tgg agc tcc gga gat     1020
Arg Arg Asn Gln Glu Arg Ala Leu Arg Thr Val Trp Ser Ser Gly Asp
225                 230                 235                 240 gac aag gag cag ctg gtg aag aac aca tat gtc ctg tgaccgccct          1066
Asp Lys Glu Gln Leu Val Lys Asn Thr Tyr Val Leu
                245                 250 gtcgccaaga ggactgggga agggagggga gactatgtgt gagcttttt taaatagagg    1126 gattgactcg gatttgagtg atcattaggg ctgaggtctg tttctctggg aggtaggacg   1186
gctgcttcct ggtctggcag ggatgggttt gctttggaaa tcctctagga ggctcctcct   1246
cgcatggcct gcagtctggc agcagccccg agttgtttcc tcgctgatcg atttctttcc   1306
tccaggtaga gttttctttg cttatgttga attccattgc ctccttttct cnatcacaga   1366
agtgatgttg gaatcgtttc ttttgtttgt ctgatttatg gttttttta gtataaacaa    1426 aagttttta ttagcattct gaaagaagga agtaaaatg tacaagttta ataaaaggg      1486 gccttcccct ttagaataaa tttccagcat gttgctttca aaaaaaaaaa aaaaaaa      1544
```

<210> SEQ ID NO 49
<211> LENGTH: 252
<212> TYPE: PRT
<213> ORGANISM: Homo sapiens
<220> FEATURE:
<221> NAME/KEY: SIGNAL
<222> LOCATION: (1)..(27)
<223> OTHER INFORMATION:

<400> SEQUENCE: 49

Met Ala Gln Leu Cys Gly Leu Arg Arg Ser Arg Ala Phe Leu Ala Leu
1               5                   10                  15

Leu Gly Ser Leu Leu Leu Ser Gly Val Leu Ala Ala Asp Arg Glu Arg
            20                  25                  30

```
Ser Ile His Asp Phe Cys Leu Val Ser Lys Val Val Gly Arg Cys Arg
        35                  40                  45

Ala Ser Met Pro Arg Trp Trp Tyr Asn Val Thr Asp Gly Ser Cys Gln
 50                  55                  60

Leu Phe Val Tyr Gly Gly Cys Asp Gly Asn Ser Asn Tyr Leu Thr
 65                  70                  75                  80

Lys Glu Glu Cys Leu Lys Lys Cys Ala Thr Val Thr Glu Asn Ala Thr
                 85                  90                  95

Gly Asp Leu Ala Thr Ser Arg Asn Ala Ala Asp Ser Ser Val Pro Ser
                100                 105                 110

Ala Pro Arg Arg Gln Asp Ser Glu Asp His Ser Ser Asp Met Phe Asn
            115                 120                 125

Tyr Glu Glu Tyr Cys Thr Ala Asn Ala Val Thr Gly Pro Cys Arg Ala
130                 135                 140

Ser Phe Pro Arg Trp Tyr Phe Asp Val Glu Arg Asn Ser Cys Asn Asn
145                 150                 155                 160

Phe Ile Tyr Gly Gly Cys Arg Gly Asn Lys Asn Ser Tyr Arg Ser Glu
                165                 170                 175

Glu Ala Cys Met Leu Arg Cys Phe Arg Gln Gln Glu Asn Pro Pro Leu
            180                 185                 190

Pro Leu Gly Ser Lys Val Val Leu Ala Gly Leu Phe Val Met Val
            195                 200                 205

Leu Ile Leu Phe Leu Gly Ala Ser Met Val Tyr Leu Ile Arg Val Ala
    210                 215                 220

Arg Arg Asn Gln Glu Arg Ala Leu Arg Thr Val Trp Ser Ser Gly Asp
225                 230                 235                 240

Asp Lys Glu Gln Leu Val Lys Asn Thr Tyr Val Leu
                245                 250

<210> SEQ ID NO 50
<211> LENGTH: 146
<212> TYPE: PRT
<213> ORGANISM: Homo sapiens

<400> SEQUENCE: 50

Cys Leu Val Ser Lys Val Val Gly Arg Cys Arg Ala Ser Met Pro Arg
 1               5                  10                  15

Trp Trp Tyr Asn Val Thr Asp Gly Ser Cys Gln Leu Phe Val Tyr Gly
                 20                  25                  30

Gly Cys Asp Gly Asn Ser Asn Tyr Leu Thr Lys Glu Glu Cys Leu
             35                  40                  45

Lys Lys Cys Ala Thr Val Thr Glu Asn Ala Thr Gly Asp Leu Ala Thr
 50                  55                  60

Ser Arg Asn Ala Ala Asp Ser Ser Val Pro Ser Ala Pro Arg Arg Gln
 65                  70                  75                  80

Asp Ser Glu Asp His Ser Ser Asp Met Phe Asn Tyr Glu Glu Tyr Cys
                 85                  90                  95

Thr Ala Asn Ala Val Thr Gly Pro Cys Arg Ala Ser Phe Pro Arg Trp
            100                 105                 110

Tyr Phe Asp Val Glu Arg Asn Ser Cys Asn Asn Phe Ile Tyr Gly Gly
        115                 120                 125

Cys Arg Gly Asn Lys Asn Ser Tyr Arg Ser Glu Glu Ala Cys Met Leu
130                 135                 140

Arg Cys
145
```

<210> SEQ ID NO 51
<211> LENGTH: 1530
<212> TYPE: DNA
<213> ORGANISM: Artificial Sequence
<220> FEATURE:
<223> OTHER INFORMATION: Consensus bikunin sequence of Fig. 4C.
<220> FEATURE:
<221> NAME/KEY: misc_feature
<222> LOCATION: (46)..(46)
<223> OTHER INFORMATION: "n" is any nucleotide.
<220> FEATURE:
<221> NAME/KEY: misc_feature
<222> LOCATION: (117)..(117)
<223> OTHER INFORMATION: "n" is any nucleotide.
<220> FEATURE:
<221> NAME/KEY: misc_feature
<222> LOCATION: (313)..(313)
<223> OTHER INFORMATION: "n" is any nucleotide.

<400> SEQUENCE: 51

```
gcgacctccg cgcgttggga ggtgtagcgc ggctctgaac gcgtgnaggg ccgttgagtg      60
tcgcaggcgg cgagggcgcg agtgaggagc agacccaggc atcgcgcgcc gagaagncgg     120
gcgtccccac actgaaggtc cggaaaggcg acttccgggg gctttggcac ctggcggacc     180
ctcccggagc gtcggcacct gaacgcgagg cgctccattg cgcgtgcgtt tgagggcttt     240
cccgcacctg atcgcgagac cccaacggct ggtggcgtcg ctgcgcgtct cggctgagct     300
ggccatggcg cantgttgcg ggctgaggcg gacggcgttt ctcgcctgct gggatcgctg     360
ctcctctctg gggtcctggc ggccgaccga gaacgcagca tccacgactt ctgcctggtg     420
tcgaaggtgg tgggcagatg ccgggcctcc atgcctaggt ggtggtacaa tgtcactgac     480
ggatcctgcc agctgtttgt gtatgggggc tgtgacggaa acagcaataa ttacctgacc     540
aaggaggagt gcctcaagaa atgtgccact gtcacagaga atgccacggg tgacctggcc     600
accagcagga atgcagcgga ttcctctgtc ccaagtgctc ccagaaggca ggattctgaa     660
gaccactcca gcgatatgtt caactatgaa gaatactgca ccgccaacgc agtcactggg     720
ccttgccgtg catccttccc acgctggtac tttgacgtgg agaggaactc ctgcaataac     780
ttcatctatg gaggctgccg gggcaataag aacagctacc gctctgagga ggcctgcatg     840
ctccgctgct tccgccagca ggagaatcct ccctgcccc ttggctcaaa ggtggtggtt     900
ctggcggggc tgttcgtgat ggtgttgatc ctcttcctgg gagcctccat ggtctacctg     960
atccgggtgg cacggaggaa ccaggagcgt gccctgcgca ccgtctggag ctccggagat    1020
gacaaggagc agctggtgaa gaacacatat gtcctgtgac cgccctgtcg ccaagaggac    1080
tggggaaggg aggggagact atgtgtgagc ttttttttaaa tagagggatt gactcggatt    1140
tgagtgatca ttagggctga ggtctgtttc tctgggaggt aggacggctg cttcctggtc    1200
tggcagggat gggtttgctt tggaaatcct ctaggaggct cctcctcgca tggcctgcag    1260
tctggcagca gccccgagtt gtttcctcgc tgatcgattt ctttcctcca ggtagagttt    1320
tctttgctta tgttgaattc cattgcctct tttctcatca cagaagtgat gttggaatcg    1380
tttcttttgt ttgtctgatt tatggttttt ttaagtataa acaaaagttt tttattagca    1440
ttctgaaaga aggaaagtaa aatgtacaag tttaataaaa aggggccttc ccctttagaa    1500
taaaaaaaaa aaaaaaaaa aaaaaaaaa                                        1530
```

<210> SEQ ID NO 52
<211> LENGTH: 170
<212> TYPE: PRT

<210> SEQ ID NO 52
<211> LENGTH: (not shown)
<212> TYPE: PRT
<213> ORGANISM: Homo sapiens

<400> SEQUENCE: 52

```
Ala Asp Arg Glu Arg Ser Ile His Asp Phe Cys Leu Val Ser Lys Val
1               5                   10                  15

Val Gly Arg Cys Arg Ala Ser Met Pro Arg Trp Trp Tyr Asn Val Thr
            20                  25                  30

Asp Gly Ser Cys Gln Leu Phe Val Tyr Gly Gly Cys Asp Gly Asn Ser
        35                  40                  45

Asn Asn Tyr Leu Thr Lys Glu Glu Cys Leu Lys Lys Cys Ala Thr Val
    50                  55                  60

Thr Glu Asn Ala Thr Gly Asp Leu Ala Thr Ser Arg Asn Ala Ala Asp
65                  70                  75                  80

Ser Ser Val Pro Ser Ala Pro Arg Arg Gln Asp Ser Glu Asp His Ser
                85                  90                  95

Ser Asp Met Phe Asn Tyr Glu Glu Tyr Cys Thr Ala Asn Ala Val Thr
            100                 105                 110

Gly Pro Cys Arg Ala Ser Phe Pro Arg Trp Tyr Phe Asp Val Glu Arg
        115                 120                 125

Asn Ser Cys Asn Asn Phe Ile Tyr Gly Gly Cys Arg Gly Asn Lys Asn
    130                 135                 140

Ser Tyr Arg Ser Glu Glu Ala Cys Met Leu Arg Cys Phe Arg Gln Gln
145                 150                 155                 160

Glu Asn Pro Pro Leu Pro Leu Gly Ser Lys
                165                 170
```

<210> SEQ ID NO 53
<211> LENGTH: 27
<212> TYPE: PRT
<213> ORGANISM: Homo sapiens

<400> SEQUENCE: 53

```
Met Ala Gln Leu Cys Gly Leu Arg Arg Ser Arg Ala Phe Leu Ala Leu
1               5                   10                  15

Leu Gly Ser Leu Leu Leu Ser Gly Val Leu Ala
            20                  25
```

<210> SEQ ID NO 54
<211> LENGTH: 23
<212> TYPE: PRT
<213> ORGANISM: Homo sapiens

<400> SEQUENCE: 54

```
Met Leu Arg Ala Glu Ala Asp Gly Val Ser Arg Leu Leu Gly Ser Leu
1               5                   10                  15

Leu Leu Ser Gly Val Leu Ala
            20
```

<210> SEQ ID NO 55
<211> LENGTH: 102
<212> TYPE: DNA
<213> ORGANISM: Artificial Sequence
<220> FEATURE:
<223> OTHER INFORMATION: 5' sense oligonucleotide used for construct #2 in Example 5.

<400> SEQUENCE: 55

```
gaagggtaa gcttggataa aagagaagaa tactgtactg ctaatgctgt tactggtcca    60
tgtagagctt cttttccaag atggtacttt gatgttgaaa ga                    102
```

<210> SEQ ID NO 56
<211> LENGTH: 129
<212> TYPE: DNA
<213> ORGANISM: Artificial Sequence
<220> FEATURE:
<223> OTHER INFORMATION: 3' antisense oligonucleotide used for construct
    #2 in Example 5.

<400> SEQUENCE: 56
actggatcct cattggcgaa aacatctcaa catacaggct tcttcagatc tgtaagaatt     60
tttattacct ctacaaccac cgtaaataaa attattacaa gaatttcttt caacatcaaa    120
gtaccatct                                                            129

<210> SEQ ID NO 57
<211> LENGTH: 108
<212> TYPE: DNA
<213> ORGANISM: Artificial Sequence
<220> FEATURE:
<223> OTHER INFORMATION: 5' sense oligonucleotide used for construct #3
    in Example 5.

<400> SEQUENCE: 57 gaagggtaa gcttggataa aagaaattac gaagaatact gtactgctaa tgctgttact      60
ggtccatgta gagcttcttt tccaagatgg tactttgatg ttgaaaga                 108

<210> SEQ ID NO 58
<211> LENGTH: 117
<212> TYPE: DNA
<213> ORGANISM: Artificial Sequence
<220> FEATURE:
<223> OTHER INFORMATION: 5' sense oligonucleotide used for construct #4
    in Example 5.

<400> SEQUENCE: 58 gaagggtaa gcttggataa aagagatatg tttaattacg aagaatactg tactgctaat      60
gctgttactg gtccatgtag agcttctttt ccaagatggt actttgatgt tgaaaga       117

<210> SEQ ID NO 59
<211> LENGTH: 19
<212> TYPE: DNA
<213> ORGANISM: Artificial Sequence
<220> FEATURE:
<223> OTHER INFORMATION: Sense oligonucleotide used in PCR in Example 8.

<400> SEQUENCE: 59
cacctgatcg cgagacccc                                                  19

<210> SEQ ID NO 60
<211> LENGTH: 23
<212> TYPE: DNA
<213> ORGANISM: Artificial Sequence
<220> FEATURE:
<223> OTHER INFORMATION: Antisense oligonucleotide used in PCR in
    Example 8.

<400> SEQUENCE: 60
ctggcggaag cagcggagca tgc                                             23

<210> SEQ ID NO 61
<211> LENGTH: 45
<212> TYPE: DNA
<213> ORGANISM: Artificial Sequence
<220> FEATURE:

```
<223> OTHER INFORMATION: Oligonucleotide used in in vitro mutagenesis in
      Example 9.

<400> SEQUENCE: 61
cgcgtctcgg ctgacctggc cctgcagatg gcgcacgtgt gcggg                45

<210> SEQ ID NO 62
<211> LENGTH: 60
<212> TYPE: DNA
<213> ORGANISM: Artificial Sequence
<220> FEATURE:
<223> OTHER INFORMATION: Oligonucleotide used in in vitro mutagenesis in
      Example 9.

<400> SEQUENCE: 62
ctgccccttg gctcaaagta ggaagatctt cccccgggg gggtggttct ggcggggctg    60

<210> SEQ ID NO 63
<211> LENGTH: 14
<212> TYPE: PRT
<213> ORGANISM: Homo sapiens

<400> SEQUENCE: 63

Leu Arg Cys Phe Arg Gln Gln Glu Asn Pro Pro Pro Leu Gly
1               5                   10

<210> SEQ ID NO 64
<211> LENGTH: 20
<212> TYPE: PRT
<213> ORGANISM: Homo sapiens

<400> SEQUENCE: 64

Ala Asp Arg Glu Arg Ser Ile His Asp Phe Cys Leu Val Ser Lys Val
1               5                   10                  15

Val Gly Arg Cys
            20

<210> SEQ ID NO 65
<211> LENGTH: 20
<212> TYPE: PRT
<213> ORGANISM: Homo sapiens

<400> SEQUENCE: 65

Phe Asn Tyr Glu Glu Tyr Cys Thr Ala Asn Ala Val Thr Gly Pro Cys
1               5                   10                  15

Arg Ala Ser Phe
            20

<210> SEQ ID NO 66
<211> LENGTH: 11
<212> TYPE: PRT
<213> ORGANISM: Homo sapiens

<400> SEQUENCE: 66

Pro Arg Tyr Val Asp Gly Ser Gln Phe Tyr Gly
1               5                   10

<210> SEQ ID NO 67
<211> LENGTH: 55
<212> TYPE: PRT
<213> ORGANISM: Homo sapiens

<400> SEQUENCE: 67

Val Val Val Leu Ala Gly Leu Phe Val Met Val Leu Ile Leu Phe Leu
```

```
            1               5                  10                 15
Gly Ala Ser Met Val Tyr Leu Ile Arg Val Ala Arg Arg Asn Gln Glu
                20                  25                 30

Arg Ala Leu Arg Thr Val Trp Ser Ser Gly Asp Asp Lys Glu Gln Leu
                35                  40                 45

Val Lys Asn Thr Tyr Val Leu
                50                  55
```

<210> SEQ ID NO 68
<211> LENGTH: 43
<212> TYPE: PRT
<213> ORGANISM: Homo sapiens

<400> SEQUENCE: 68

```
Val Val Val Leu Ala Gly Leu Phe Val Met Val Leu Ile Leu Phe Leu
1                5                  10                 15

Gly Ala Ser Met Val Tyr Leu Ile Arg Val Ala Arg Arg Asn Gln Glu
                20                  25                 30

Arg Ala Leu Arg Thr Val Trp Ser Phe Gly Asp
                35                  40
```

<210> SEQ ID NO 69
<211> LENGTH: 55
<212> TYPE: PRT
<213> ORGANISM: Homo sapiens

<400> SEQUENCE: 69

```
Val Val Val Leu Ala Gly Leu Phe Val Met Val Leu Ile Leu Phe Leu
1                5                  10                 15

Gly Ala Ser Met Val Tyr Leu Ile Arg Val Ala Arg Arg Asn Gln Glu
                20                  25                 30

Arg Ala Leu Arg Thr Val Trp Ser Ser Gly Asp Asp Lys Glu Gln Leu
                35                  40                 45

Val Lys Asn Thr Tyr Val Leu
                50                  55
```

<210> SEQ ID NO 70
<211> LENGTH: 213
<212> TYPE: PRT
<213> ORGANISM: Homo sapiens

<400> SEQUENCE: 70

```
Ala Asp Arg Glu Arg Ser Ile His Asp Phe Cys Leu Val Ser Lys Val
1                5                  10                 15

Val Gly Arg Cys Arg Ala Ser Met Pro Arg Trp Trp Tyr Asn Val Thr
                20                  25                 30

Asp Gly Ser Cys Gln Leu Phe Val Tyr Gly Gly Cys Asp Gly Asn Ser
                35                  40                 45

Asn Asn Tyr Leu Thr Lys Glu Glu Cys Leu Lys Lys Cys Ala Thr Val
                50                  55                 60

Thr Glu Asn Ala Thr Gly Asp Leu Ala Thr Ser Arg Asn Ala Ala Asp
65                  70                  75                 80

Ser Ser Val Pro Ser Ala Pro Arg Arg Gln Asp Ser Glu Asp His Ser
                85                  90                 95

Ser Asp Met Phe Asn Tyr Glu Glu Tyr Cys Thr Ala Asn Ala Val Thr
                100                 105                110

Gly Pro Cys Arg Ala Ser Phe Pro Arg Trp Tyr Phe Asp Val Glu Arg
                115                 120                125
```

```
Asn Ser Cys Asn Asn Phe Ile Tyr Gly Gly Cys Arg Gly Asn Lys Asn
        130                 135                 140

Ser Tyr Arg Ser Glu Glu Ala Cys Met Leu Arg Cys Phe Arg Gln Gln
145                 150                 155                 160

Glu Asn Pro Pro Leu Pro Leu Gly Ser Lys Val Val Leu Ala Gly
                165                 170                 175

Leu Phe Val Met Val Leu Ile Leu Phe Leu Gly Ala Ser Met Val Tyr
                180                 185                 190

Leu Ile Arg Val Ala Arg Arg Asn Gln Glu Arg Ala Leu Arg Thr Val
                195                 200                 205

Trp Ser Phe Gly Asp
        210

<210> SEQ ID NO 71
<211> LENGTH: 225
<212> TYPE: PRT
<213> ORGANISM: Homo sapiens

<400> SEQUENCE: 71

Ala Asp Arg Glu Arg Ser Ile His Asp Phe Cys Leu Val Ser Lys Val
1               5                   10                  15

Val Gly Arg Cys Arg Ala Ser Met Pro Arg Trp Trp Tyr Asn Val Thr
                20                  25                  30

Asp Gly Ser Cys Gln Leu Phe Val Tyr Gly Gly Cys Asp Gly Asn Ser
                35                  40                  45

Asn Asn Tyr Leu Thr Lys Glu Glu Cys Leu Lys Lys Cys Ala Thr Val
        50                  55                  60

Thr Glu Asn Ala Thr Gly Asp Leu Ala Thr Ser Arg Asn Ala Ala Asp
65                  70                  75                  80

Ser Ser Val Pro Ser Ala Pro Arg Arg Gln Asp Ser Glu Asp His Ser
                85                  90                  95

Ser Asp Met Phe Asn Tyr Glu Glu Tyr Cys Thr Ala Asn Ala Val Thr
                100                 105                 110

Gly Pro Cys Arg Ala Ser Phe Pro Arg Trp Tyr Phe Asp Val Glu Arg
                115                 120                 125

Asn Ser Cys Asn Asn Phe Ile Tyr Gly Gly Cys Arg Gly Asn Lys Asn
        130                 135                 140

Ser Tyr Arg Ser Glu Glu Ala Cys Met Leu Arg Cys Phe Arg Gln Gln
145                 150                 155                 160

Glu Asn Pro Pro Leu Pro Leu Gly Ser Lys Val Val Leu Ala Gly
                165                 170                 175

Leu Phe Val Met Val Leu Ile Leu Phe Leu Gly Ala Ser Met Val Tyr
                180                 185                 190

Leu Ile Arg Val Ala Arg Arg Asn Gln Glu Arg Ala Leu Arg Thr Val
                195                 200                 205

Trp Ser Ser Gly Asp Asp Lys Glu Gln Leu Val Lys Asn Thr Tyr Val
        210                 215                 220

Leu
225

<210> SEQ ID NO 72
<211> LENGTH: 19
<212> TYPE: PRT
<213> ORGANISM: Homo sapiens
<220> FEATURE:
<221> NAME/KEY: MISC_FEATURE
```

-continued

```
<222> LOCATION: (9)..(9)
<223> OTHER INFORMATION: "Xaa" is Ile, Thr, Asn, or Ser.
<220> FEATURE:
<221> NAME/KEY: MISC_FEATURE
<222> LOCATION: (11)..(11)
<223> OTHER INFORMATION: "Xaa" is Val, Ala, Glu, or Gly.
<220> FEATURE:
<221> NAME/KEY: MISC_FEATURE
<222> LOCATION: (17)..(17)
<223> OTHER INFORMATION: "Xaa" is Ser, Pro, Thr, or Ala.
<220> FEATURE:
<221> NAME/KEY: MISC_FEATURE
<222> LOCATION: (19)..(19)
<223> OTHER INFORMATION: "Xaa" is Tyr, His, Asn, or Asp.

<400> SEQUENCE: 72

Arg Pro Leu Gln Arg Tyr Val Ser Xaa Ile Xaa Arg Ile Ile Ala Pro
1               5                   10                  15

Xaa Thr Xaa

<210> SEQ ID NO 73
<211> LENGTH: 108
<212> TYPE: PRT
<213> ORGANISM: Homo sapiens

<400> SEQUENCE: 73

Pro Gly His Gln Gln Glu Cys Ser Gly Phe Leu Cys Pro Lys Ser Pro
1               5                   10                  15

Arg Arg Gln Asp Ser Glu Asp His Ser Ser Asp Met Phe Asn Tyr Glu
                20                  25                  30

Glu Tyr Cys Thr Ala Asn Ala Val Thr Gly Pro Cys Arg Ala Ser Phe
            35                  40                  45

Pro Arg Trp Tyr Phe Asp Val Glu Arg Asn Ser Cys Asn Asn Phe Ile
        50                  55                  60

Tyr Gly Gly Cys Arg Gly Asn Lys Asn Ser Tyr Arg Ser Glu Ala
65                  70                  75                  80

Cys Met Leu Arg Cys Phe Arg Gln Gln Glu Asn Pro Leu Pro Leu
                85                  90                  95

Gly Ser Lys Val Val Val Leu Ala Gly Ala Val Ser
            100                 105

<210> SEQ ID NO 74
<211> LENGTH: 31
<212> TYPE: PRT
<213> ORGANISM: Homo sapiens
<220> FEATURE:
<221> NAME/KEY: MISC_FEATURE
<222> LOCATION: (25)..(25)
<223> OTHER INFORMATION: "Xaa" is Asp or Glu.

<400> SEQUENCE: 74

Ser Phe Ser Trp Gly Ala Ser Met Val Leu Leu Ile Pro Gly Gly Lys
1               5                   10                  15

Glu Glu Pro Gly Ala Cys Pro Ala Xaa Arg Leu Glu Leu Arg Arg
                20                  25                  30

<210> SEQ ID NO 75
<211> LENGTH: 511
<212> TYPE: DNA
<213> ORGANISM: Artificial Sequence
<220> FEATURE:
<223> OTHER INFORMATION: Corrected version of EST R74593 (see Fig. 3 and
      page 28).
<220> FEATURE:
<221> NAME/KEY: misc_feature
```

```
<222> LOCATION: (425)..(425)
<223> OTHER INFORMATION: "n" is any nucleotide.
<220> FEATURE:
<221> NAME/KEY: misc_feature
<222> LOCATION: (482)..(482)
<223> OTHER INFORMATION: "n" is any nucleotide.
<220> FEATURE:
<221> NAME/KEY: misc_feature
<222> LOCATION: (510)..(510)
<223> OTHER INFORMATION: "n" is any nucleotide.

<400> SEQUENCE: 75
gcaataatta cctgaccaag gaggagtgcc tcaagaaatg tgccactgtc acagagaatg      60
ccacgggtga cctggccacc agcaggaatg cagcggattc ctctgtccca agtgctccca     120
gaaggcagga ttctgaagac cactccagcg atatgttcaa ctatgaagaa tactgcaccg     180
ccaacgcagt cactgggcct tgccgtgcat ccttcccacg ctggtacttt gacgtggaga     240
ggaactcctg caataacttc atctatggag gctgccgggg caataagaac agctaccgct     300
ctgaggaggc ctgcatgctc cgctgcttcc gccagcagga gaatcctccc ctgccccttg     360
gctcaaaggt ggtggttctg gccggggctg tttcgtgatg gtgttgatcc ttttcctggg     420
gagcntccat ggtcttactg attccgggtg gcaaggagga accaggagcg tgccctgcgg     480
ancgtctgga gcttcggaga tgacaagggn t                                    511

<210> SEQ ID NO 76
<211> LENGTH: 31
<212> TYPE: PRT
<213> ORGANISM: Artificial Sequence
<220> FEATURE:
<223> OTHER INFORMATION: Amino acids 184-214 of translation of consensus
      sequence in Fig. 3.
<220> FEATURE:
<221> NAME/KEY: MISC_FEATURE
<222> LOCATION: (25)..(25)
<223> OTHER INFORMATION: "Xaa" is Asp or Glu.

<400> SEQUENCE: 76

Ser Phe Ser Trp Gly Ala Ser Met Val Leu Leu Ile Pro Gly Gly Lys
1               5                   10                  15

Glu Glu Pro Gly Ala Cys Pro Ala Xaa Arg Leu Glu Leu Arg Arg
            20                  25                  30

<210> SEQ ID NO 77
<211> LENGTH: 312
<212> TYPE: DNA
<213> ORGANISM: Homo sapiens
<220> FEATURE:
<221> NAME/KEY: misc_feature
<222> LOCATION: (45)..(45)
<223> OTHER INFORMATION: "n" is any nucleotide.
<220> FEATURE:
<221> NAME/KEY: misc_feature
<222> LOCATION: (49)..(49)
<223> OTHER INFORMATION: "n" is any nucleotide.
<220> FEATURE:
<221> NAME/KEY: misc_feature
<222> LOCATION: (118)..(118)
<223> OTHER INFORMATION: "n" is any nucleotide.
<220> FEATURE:
<221> NAME/KEY: misc_feature
<222> LOCATION: (231)..(231)
<223> OTHER INFORMATION: "n" is any nucleotide.
<220> FEATURE:
<221> NAME/KEY: misc_feature
<222> LOCATION: (305)..(305)
<223> OTHER INFORMATION: "n" is any nucleotide.

<400> SEQUENCE: 77
```

-continued

```
gcgacctccg cgcgttggga ggtgtagcgc ggctctgaac gcgtngagng gccgttgagt    60
gtcgcaggcg gcgagggcgc gagtgaggag cagacccagg catcgcgcgc cgagaagncg    120
ggcgtcccca cactgaaggt ccggaaaggc gacttccggg ggctttggca cctggcggac    180
cctcccggag cgtcggcacc tgaacgcgag gcgctccatt gcgcgtgcgt ntgaggggct    240
tcccgcacct gatcgcgaga ccccaacggc tggtggcgtc gcctgcgcgt ctcggctgag    300
ctggncatgt cg                                                       312
```

<210> SEQ ID NO 78
<211> LENGTH: 330
<212> TYPE: DNA
<213> ORGANISM: Homo sapiens
<220> FEATURE:
<221> NAME/KEY: misc_feature
<222> LOCATION: (117)..(117)
<223> OTHER INFORMATION: "n" is any nucleotide.
<220> FEATURE:
<221> NAME/KEY: misc_feature
<222> LOCATION: (123)..(123)
<223> OTHER INFORMATION: "n" is any nucleotide.
<220> FEATURE:
<221> NAME/KEY: misc_feature
<222> LOCATION: (321)..(321)
<223> OTHER INFORMATION: "n" is any nucleotide.

<400> SEQUENCE: 78

```
gcgacctccg cgcgttggga ggtgtagcgc ggctctgaac gcgtgcaggg ccgttgagtg    60
tcgcaggcgg cgagggcgcg agtgaggagc agacccaggc atcgcgcgcc gagaagncgg    120
gcntccccac actgaaggtc cggaaaggcg acttccgggg ctttggcac ctggcggacc    180 ctcccggagc gtggcacctg aacgcgaggc gctccattgc gcgtgcgttt gagggcttc    240 ccgcacctga tcgcgagacc ccaacggctg gtggcgtcgc ctgcgcgtct cggctgagct    300
ggccatggcg cactgtgcgg ngctgaggcg                                    330
```

<210> SEQ ID NO 79
<211> LENGTH: 283
<212> TYPE: DNA
<213> ORGANISM: Homo sapiens
<220> FEATURE:
<221> NAME/KEY: misc_feature
<222> LOCATION: (9)..(9)
<223> OTHER INFORMATION: "n" is any nucleotide.
<220> FEATURE:
<221> NAME/KEY: misc_feature
<222> LOCATION: (11)..(11)
<223> OTHER INFORMATION: "n" is any nucleotide.
<220> FEATURE:
<221> NAME/KEY: misc_feature
<222> LOCATION: (222)..(222)
<223> OTHER INFORMATION: "n" is any nucleotide.
<220> FEATURE:
<221> NAME/KEY: misc_feature
<222> LOCATION: (231)..(231)
<223> OTHER INFORMATION: "n" is any nucleotide.
<220> FEATURE:
<221> NAME/KEY: misc_feature
<222> LOCATION: (262)..(262)
<223> OTHER INFORMATION: "n" is any nucleotide.
<220> FEATURE:
<221> NAME/KEY: misc_feature
<222> LOCATION: (267)..(274)
<223> OTHER INFORMATION: "n" is any nucleotide.

<400> SEQUENCE: 79

```
ttgagtgtng naggcggcga gggcgcgagt gaggagcaga cccaggcatc gcgcgccgag    60
```

| aaggccgggc gtccccacac tgaaggtccg gaaaggcgac ttccgggggc tttggcacct | 120 |
|---|---|
| ggcggaccct cccggagcgt cggcacctga acgcgaggcg ctccattgcg cgtgcgtttg | 180 |
| aggggcttcc cgcacctgat cgcgagaccc aacggctgg tngcgtcgct ncgcgtctcg | 240 |
| gctgagcttg gccatggcgc antgttncgg gctnaggcgg acg | 283 |

<210> SEQ ID NO 80
<211> LENGTH: 423
<212> TYPE: DNA
<213> ORGANISM: Homo sapiens
<220> FEATURE:
<221> NAME/KEY: misc_feature
<222> LOCATION: (44)..(44)
<223> OTHER INFORMATION: "n" is any nucleotide.
<220> FEATURE:
<221> NAME/KEY: misc_feature
<222> LOCATION: (46)..(46)
<223> OTHER INFORMATION: "n" is any nucleotide.
<220> FEATURE:
<221> NAME/KEY: misc_feature
<222> LOCATION: (76)..(76)
<223> OTHER INFORMATION: "n" is any nucleotide.
<220> FEATURE:
<221> NAME/KEY: misc_feature
<222> LOCATION: (114)..(114)
<223> OTHER INFORMATION: "n" is any nucleotide.
<220> FEATURE:
<221> NAME/KEY: misc_feature
<222> LOCATION: (187)..(187)
<223> OTHER INFORMATION: "n" is any nucleotide.
<220> FEATURE:
<221> NAME/KEY: misc_feature
<222> LOCATION: (268)..(268)
<223> OTHER INFORMATION: "n" is any nucleotide.
<220> FEATURE:
<221> NAME/KEY: misc_feature
<222> LOCATION: (309)..(309)
<223> OTHER INFORMATION: "n" is any nucleotide.
<220> FEATURE:
<221> NAME/KEY: misc_feature
<222> LOCATION: (317)..(317)
<223> OTHER INFORMATION: "n" is any nucleotide.
<220> FEATURE:
<221> NAME/KEY: misc_feature
<222> LOCATION: (332)..(332)
<223> OTHER INFORMATION: "n" is any nucleotide.
<220> FEATURE:
<221> NAME/KEY: misc_feature
<222> LOCATION: (370)..(370)
<223> OTHER INFORMATION: "n" is any nucleotide.

<400> SEQUENCE: 80

| ggcgacctcc gcgcgttggg aggtgtagcg cgctctgaac gggnanggc cgttgagtgt | 60 |
|---|---|
| cgcaggcggc agggcngagt gaggagcaga cccaggcatc gcgcgccgag aagncgggcg | 120 |
| tccccacact gaaggtccgg aaaggcgact tccgggggct ttggcacctg gcggacgtcc | 180 |
| cggagcnggc acctgaacgc gaggcgctcc attgcgcgtg cgtttgaggg gcttcccgca | 240 |
| cctgatcgcg agaccccaac ggctggtngc gtcgctggcc cgttctcggc tgagctggcc | 300 |
| atggcgcant gttgcgngct gaggcggacc gncgtttttc ttcgccttgc tgggattcgc | 360 |
| ttgcttcctn tctgggggtt cctgggcggc cgaccgagaa cgcagcatcc aagaatttt | 420 |
| gcc | 423 |

<210> SEQ ID NO 81
<211> LENGTH: 344
<212> TYPE: DNA
<213> ORGANISM: Homo sapiens
<220> FEATURE:
<221> NAME/KEY: misc_feature

```
<222> LOCATION: (35)..(35)
<223> OTHER INFORMATION: "n" is any nucleotide.
<220> FEATURE:
<221> NAME/KEY: misc_feature
<222> LOCATION: (148)..(148)
<223> OTHER INFORMATION: "n" is any nucleotide.
<220> FEATURE:
<221> NAME/KEY: misc_feature
<222> LOCATION: (235)..(235)
<223> OTHER INFORMATION: "n" is any nucleotide.
<220> FEATURE:
<221> NAME/KEY: misc_feature
<222> LOCATION: (261)..(261)
<223> OTHER INFORMATION: "n" is any nucleotide.
<220> FEATURE:
<221> NAME/KEY: misc_feature
<222> LOCATION: (272)..(272)
<223> OTHER INFORMATION: "n" is any nucleotide.
<220> FEATURE:
<221> NAME/KEY: misc_feature
<222> LOCATION: (293)..(293)
<223> OTHER INFORMATION: "n" is any nucleotide.
<220> FEATURE:
<221> NAME/KEY: misc_feature
<222> LOCATION: (300)..(300)
<223> OTHER INFORMATION: "n" is any nucleotide.
<220> FEATURE:
<221> NAME/KEY: misc_feature
<222> LOCATION: (313)..(313)
<223> OTHER INFORMATION: "n" is any nucleotide.
<220> FEATURE:
<221> NAME/KEY: misc_feature
<222> LOCATION: (320)..(320)
<223> OTHER INFORMATION: "n" is any nucleotide.

<400> SEQUENCE: 81
ggaggagcag acccaggcat cgcgcgccga gaagncgggc gtccccacac tgaaggtccg      60
gaaaggcgac ttccgggggc tttggcacct ggcggaccct cccggagcgt cggcacctga     120
acgcgaggcg ctccattgcg cgtgcgtntg gagggcttc ccgcacctga tcgcgagacc     180
ccaacggctg gtgggcgtcg ctgcgcgtct tcggctgagc tgggccatgg cgcanttgtt     240
gcgggctgag gcggacgcgg ncgttttttc gnccttgctg ggattcgttg ttnctctctn     300
ggggttctgg ggnggccgan cgagaacgca agcattcacg attt                     344

<210> SEQ ID NO 82
<211> LENGTH: 253
<212> TYPE: DNA
<213> ORGANISM: Homo sapiens
<220> FEATURE:
<221> NAME/KEY: misc_feature
<222> LOCATION: (56)..(56)
<223> OTHER INFORMATION: "n" is any nucleotide.
<220> FEATURE:
<221> NAME/KEY: misc_feature
<222> LOCATION: (137)..(137)
<223> OTHER INFORMATION: "n" is any nucleotide.
<220> FEATURE:
<221> NAME/KEY: misc_feature
<222> LOCATION: (145)..(145)
<223> OTHER INFORMATION: "n" is any nucleotide.
<220> FEATURE:
<221> NAME/KEY: misc_feature
<222> LOCATION: (159)..(159)
<223> OTHER INFORMATION: "n" is any nucleotide.
<220> FEATURE:
<221> NAME/KEY: misc_feature
<222> LOCATION: (233)..(233)
<223> OTHER INFORMATION: "n" is any nucleotide.

<400> SEQUENCE: 82
ggaccctccc ggagcgtcgg cacctgaacg cgaggcctcc attgcggtgc gtgtgnaggg      60
```

| | |
|---|---|
| gcttcccgca cctgatcgcg agaccccaac ggctggtggc gtcgctgcgc gtctcggctg | 120 |
| agctggccat ggcgcantgt tgcgngctga ggcggcggnc gttttctcgc ctgctgggat | 180 |
| cgctgctcct ctctggggtc ctggcggccg accgagaacg cagcatccac ganttcttcc | 240 |
| tggtgttcga agg | 253 |

<210> SEQ ID NO 83
<211> LENGTH: 419
<212> TYPE: DNA
<213> ORGANISM: Homo sapiens
<220> FEATURE:
<221> NAME/KEY: misc_feature
<222> LOCATION: (20)..(20)
<223> OTHER INFORMATION: "n" is any nucleotide.
<220> FEATURE:
<221> NAME/KEY: misc_feature
<222> LOCATION: (26)..(26)
<223> OTHER INFORMATION: "n" is any nucleotide.
<220> FEATURE:
<221> NAME/KEY: misc_feature
<222> LOCATION: (95)..(95)
<223> OTHER INFORMATION: "n" is any nucleotide.
<220> FEATURE:
<221> NAME/KEY: misc_feature
<222> LOCATION: (292)..(292)
<223> OTHER INFORMATION: "n" is any nucleotide.
<220> FEATURE:
<221> NAME/KEY: misc_feature
<222> LOCATION: (313)..(315)
<223> OTHER INFORMATION: "n" is any nucleotide.

<400> SEQUENCE: 83

| | |
|---|---|
| ttagcgcggc tctgaacgcn agaagnggcc gttgagtgtc gcaggcggcg agggcgcgag | 60 |
| tgaggagcag acccaggcat cgcgcgccga gaagncgggc gtccccacac tgaaggtccg | 120 |
| gaaaggcgac ttccggggc tttggcacct ggcggaccct cccggagcgt cggcacctga | 180 |
| acgcgaggcg ctccattgcg cgtgcgtttg aggggcttcc cgcacctgat cgcgagaccc | 240 |
| caacggctgg tggcgtcgcc tgcgcgtctc ggctgagctg gccatggcgc antggtgcgg | 300 |
| gcttgaggcg gannngccgt ttctcgcctg ctgggatcgc tgctcctctc tggggtcctg | 360 |
| gcggccgacc gagaacgcag catccacgac ttctgcctgg tgtcgaaggt ggtgggcag | 419 |

<210> SEQ ID NO 84
<211> LENGTH: 477
<212> TYPE: DNA
<213> ORGANISM: Homo sapiens
<220> FEATURE:
<221> NAME/KEY: misc_feature
<222> LOCATION: (27)..(27)
<223> OTHER INFORMATION: "n" is any nucleotide.
<220> FEATURE:
<221> NAME/KEY: misc_feature
<222> LOCATION: (139)..(139)
<223> OTHER INFORMATION: "n" is any nucleotide.
<220> FEATURE:
<221> NAME/KEY: misc_feature
<222> LOCATION: (223)..(223)
<223> OTHER INFORMATION: "n" is any nucleotide.
<220> FEATURE:
<221> NAME/KEY: misc_feature
<222> LOCATION: (232)..(232)
<223> OTHER INFORMATION: "n" is any nucleotide.
<220> FEATURE:
<221> NAME/KEY: misc_feature
<222> LOCATION: (302)..(302)
<223> OTHER INFORMATION: "n" is any nucleotide.
<220> FEATURE:
<221> NAME/KEY: misc_feature
<222> LOCATION: (310)..(310)
<223> OTHER INFORMATION: "n" is any nucleotide.

```
<220> FEATURE:
<221> NAME/KEY: misc_feature
<222> LOCATION: (322)..(322)
<223> OTHER INFORMATION: "n" is any nucleotide.
<220> FEATURE:
<221> NAME/KEY: misc_feature
<222> LOCATION: (328)..(328)
<223> OTHER INFORMATION: "n" is any nucleotide.
<220> FEATURE:
<221> NAME/KEY: misc_feature
<222> LOCATION: (357)..(357)
<223> OTHER INFORMATION: "n" is any nucleotide.
<220> FEATURE:
<221> NAME/KEY: misc_feature
<222> LOCATION: (375)..(375)
<223> OTHER INFORMATION: "n" is any nucleotide.
<220> FEATURE:
<221> NAME/KEY: misc_feature
<222> LOCATION: (392)..(392)
<223> OTHER INFORMATION: "n" is any nucleotide.
<220> FEATURE:
<221> NAME/KEY: misc_feature
<222> LOCATION: (398)..(398)
<223> OTHER INFORMATION: "n" is any nucleotide.
<220> FEATURE:
<221> NAME/KEY: misc_feature
<222> LOCATION: (405)..(405)
<223> OTHER INFORMATION: "n" is any nucleotide.
<220> FEATURE:
<221> NAME/KEY: misc_feature
<222> LOCATION: (427)..(427)
<223> OTHER INFORMATION: "n" is any nucleotide.
<220> FEATURE:
<221> NAME/KEY: misc_feature
<222> LOCATION: (437)..(437)
<223> OTHER INFORMATION: "n" is any nucleotide.
<220> FEATURE:
<221> NAME/KEY: misc_feature
<222> LOCATION: (449)..(449)
<223> OTHER INFORMATION: "n" is any nucleotide.
<220> FEATURE:
<221> NAME/KEY: misc_feature
<222> LOCATION: (458)..(458)
<223> OTHER INFORMATION: "n" is any nucleotide.
<220> FEATURE:
<221> NAME/KEY: misc_feature
<222> LOCATION: (474)..(474)
<223> OTHER INFORMATION: "n" is any nucleotide.

<400> SEQUENCE: 84
agacccaggc atcgcgcgcc gagaagncgg gcgtccccac actgaaggtc cggaaaggcg      60
acttccgggg gctttggcac ctggcggacc ctcccggagc gtcggcacct gaacgcgagg     120
cctccattgc cgtgcgttng agggcttcc cggaacttga tcgcgagacc ccaacggctg      180
gtggcgtcgc tgcgcgtcct cggctgagct ggccatggcg cantggtgcc gngctgaggc     240
cggagggccg gtttctcgcc ttgctgggat cgctgctcct ctctgggtc ctggcggccg      300 ancgaagaan gcagcaatcc angaattnct gcctggtgtt cgaaagttgg tgggcanatt     360
ccggggcctt catgnctaag gttggttggt anaatgtnaa ttaangattc ttgcaactgt     420
ttgtgtnatt ggggctntta aacggaaana caataatnac ctgaccaaag aagnaat       477

<210> SEQ ID NO 85
<211> LENGTH: 393
<212> TYPE: DNA
<213> ORGANISM: Homo sapiens
<220> FEATURE:
<221> NAME/KEY: misc_feature
<222> LOCATION: (361)..(361)
<223> OTHER INFORMATION: "n" is any nucleotide.
<220> FEATURE:
<221> NAME/KEY: misc_feature
<222> LOCATION: (367)..(367)
```

```
<223> OTHER INFORMATION: "n" is any nucleotide.
<220> FEATURE:
<221> NAME/KEY: misc_feature
<222> LOCATION: (384)..(384)
<223> OTHER INFORMATION: "n" is any nucleotide.
<220> FEATURE:
<221> NAME/KEY: misc_feature
<222> LOCATION: (390)..(390)
<223> OTHER INFORMATION: "n" is any nucleotide.

<400> SEQUENCE: 85
ggccgggtcg tttctcgcct ggctgggatc gctgctcctc tctggggtcc tggccggccg      60
accgagaacg cagcatccac gacttctgcc tggtgtcgaa ggtggtgggc agattccggg     120
cctccatgcc taggtggtgg tacaatgtca ctgacggatc ctgccagctg tttgtgtatg     180
ggggctgtga cggaaacagc aataattacc tgaccaagga ggagtgcctc aagaaatgtg     240
ccactgtcac agagaatgcc acgggtgacc tggccaccag caggaatgca gcggattcct     300
ctgtcccaag tgctcccaga aggcaggatt cttgaagacc acttcagcga tatgtttcaa     360
ntattgnaag aataattgca ccgncaacgn att                                  393

<210> SEQ ID NO 86
<211> LENGTH: 428
<212> TYPE: DNA
<213> ORGANISM: Homo sapiens
<220> FEATURE:
<221> NAME/KEY: misc_feature
<222> LOCATION: (3)..(3)
<223> OTHER INFORMATION: "n" is any nucleotide.
<220> FEATURE:
<221> NAME/KEY: misc_feature
<222> LOCATION: (11)..(12)
<223> OTHER INFORMATION: "n" is any nucleotide.
<220> FEATURE:
<221> NAME/KEY: misc_feature
<222> LOCATION: (17)..(17)
<223> OTHER INFORMATION: "n" is any nucleotide.
<220> FEATURE:
<221> NAME/KEY: misc_feature
<222> LOCATION: (48)..(48)
<223> OTHER INFORMATION: "n" is any nucleotide.
<220> FEATURE:
<221> NAME/KEY: misc_feature
<222> LOCATION: (425)..(425)
<223> OTHER INFORMATION: "n" is any nucleotide.

<400> SEQUENCE: 86
gcngcgcgtt nntcgcntgc tgggatcgct gcacctctct ggggtcgngg cggccgaccg      60
agaacgcagc atccacgact tctgcctggt gtcgaaggtg gtgggcagat gccgggcctc     120
catgcctagg tggtggtaca atgtcactga cggatcctgc cagctgtttg tgtatggggg     180
ctgtgacgga aacagcaata attacctgac caaggaggag tgcctcaaga aatgtgccac     240
tgtcacagag aatgccacgg gtgacctggc caccagcagg aatgcagcgg attcctctgt     300
cccaagtgct cccagaaggc aggattctga agaccactcc agcgatatgt tcaactatga     360
agaatactgg caccgccaac gcattcactg ggcctgcgtg catccttccc acgctggtac     420 tttgncgt                                                             428

<210> SEQ ID NO 87
<211> LENGTH: 425
<212> TYPE: DNA
<213> ORGANISM: Homo sapiens
<220> FEATURE:
<221> NAME/KEY: misc_feature
<222> LOCATION: (7)..(7)
<223> OTHER INFORMATION: "n" is any nucleotide.
```

```
<220> FEATURE:
<221> NAME/KEY: misc_feature
<222> LOCATION: (403)..(403)
<223> OTHER INFORMATION: "n" is any nucleotide.
<220> FEATURE:
<221> NAME/KEY: misc_feature
<222> LOCATION: (409)..(409)
<223> OTHER INFORMATION: "n" is any nucleotide.

<400> SEQUENCE: 87
ctgggantcg ctgctcctct ctggggtcct ggcggccgac cgagaacgca gcatccacga      60
cttctgcctg gtgtcgaagg tggtgggcag atgccgggcc tccatgccta ggtggtggta     120
caatgtcact gacggatcct gccagctgtt tgtgtatggg ggctgtgacg aaacagcaa     180 taattacctg accaaggagg agtgcctcaa gaaatgtgcc actgtcacag agaatgccac     240
gggtgacctg gccaccagca ggaatgcagc ggattcctct gtcccaagtg ctcccagaag     300
gcaggattct gaagaccact ccagcgatat gttcaactat gaagaatact gcaccgccaa     360
cgcagtcact ggggccttgc gtggaatcct ttcccacgct ggnaatttng acgttgagaa     420
ggaac                                                                 425

<210> SEQ ID NO 88
<211> LENGTH: 343
<212> TYPE: DNA
<213> ORGANISM: Homo sapiens
<220> FEATURE:
<221> NAME/KEY: misc_feature
<222> LOCATION: (48)..(48)
<223> OTHER INFORMATION: "n" is any nucleotide.
<220> FEATURE:
<221> NAME/KEY: misc_feature
<222> LOCATION: (62)..(62)
<223> OTHER INFORMATION: "n" is any nucleotide.
<220> FEATURE:
<221> NAME/KEY: misc_feature
<222> LOCATION: (211)..(211)
<223> OTHER INFORMATION: "n" is any nucleotide.
<220> FEATURE:
<221> NAME/KEY: misc_feature
<222> LOCATION: (232)..(232)
<223> OTHER INFORMATION: "n" is any nucleotide.
<220> FEATURE:
<221> NAME/KEY: misc_feature
<222> LOCATION: (245)..(245)
<223> OTHER INFORMATION: "n" is any nucleotide.
<220> FEATURE:
<221> NAME/KEY: misc_feature
<222> LOCATION: (309)..(309)
<223> OTHER INFORMATION: "n" is any nucleotide.
<220> FEATURE:
<221> NAME/KEY: misc_feature
<222> LOCATION: (318)..(318)
<223> OTHER INFORMATION: "n" is any nucleotide.

<400> SEQUENCE: 88
gattcggcac agggggaaaca gcaataatta cctgaccaag gaggagtncc tcaagaaatg      60
tnccactgtc acagagaatg ccacgggtga cctggccacc agcaggaatg cagcggattc     120
ctctgtccca agtgctccca gaaggcagga ttctgaagac cactccagcg atatgttcaa     180
ctatgaagaa tactgcaccg ccaacgcagt ncactgggcc ttgcgtggca tnccttccca     240
cgctngtact ttgacgtgga gaggaactcc tggcaataac ttcatctatg gaggcttgcc     300
ggggcaatna agaacagntt accgctcttt aggaggcctg cat                       343

<210> SEQ ID NO 89
<211> LENGTH: 510
<212> TYPE: DNA
```

```
<213> ORGANISM: Homo sapiens
<220> FEATURE:
<221> NAME/KEY: misc_feature
<222> LOCATION: (424)..(424)
<223> OTHER INFORMATION: "n" is any nucleotide.
<220> FEATURE:
<221> NAME/KEY: misc_feature
<222> LOCATION: (481)..(481)
<223> OTHER INFORMATION: "n" is any nucleotide.
<220> FEATURE:
<221> NAME/KEY: misc_feature
<222> LOCATION: (509)..(509)
<223> OTHER INFORMATION: "n" is any nucleotide.

<400> SEQUENCE: 89
gcaataatta cctgaccaag gaggagtgcc tcaagaaatg tgccactgtc acagagaatg      60
ccacgggtga cctggccacc agcaggaatg cagcggattc ctctgtccca agtctcccag     120
aaggcaggat tctgaagacc actccagcga tatgttcaac tatgaagaat actgcaccgc     180
caacgcagtc actgggcctt ccgtgcatc cttcccacgc tggtactttg acgtggagag      240
gaactcctgc aataacttca tctatggagg ctgccggggc aataagaaca gctaccgctc     300
tgaggaggcc tgcatgctcc gctgcttccg ccagcaggaa aatcctcccc tgccccttgg     360
ctcaaaggtg gtggttctgg ccggggctgt ttcgtgatgg tgttgatcct tttcctgggg    420
agcntccatg gtcttactga ttccgggtgg caaggaggaa ccaggagcgt gccctgcgga     480
ncgtctggag cttcggagat gacaagggnt                                     510

<210> SEQ ID NO 90
<211> LENGTH: 293
<212> TYPE: DNA
<213> ORGANISM: Homo sapiens
<220> FEATURE:
<221> NAME/KEY: misc_feature
<222> LOCATION: (257)..(257)
<223> OTHER INFORMATION: "n" is any nucleotide.

<400> SEQUENCE: 90
gctaccgctc tgaggaggcc tgcatgctcc gctgcttccg ccagcaggag aatcctcccc      60
tgccccttgg ctcaaaggtg gtggttctgg cggggctgtt cgtgatggtg ttgatcctct     120
tcctggggag cctccatggt ctacctgatc cgggtggcac ggagggaacc agggagcgtg     180
ccctgcgcac cgtctgggag ctccggagat gacaaggag cagctgggtg aagaacacat      240
atgttcctgt tgaccgncct gttcgccaag aggattgggg gaagggaggg gga           293

<210> SEQ ID NO 91
<211> LENGTH: 282
<212> TYPE: DNA
<213> ORGANISM: Homo sapiens
<220> FEATURE:
<221> NAME/KEY: misc_feature
<222> LOCATION: (19)..(19)
<223> OTHER INFORMATION: "n" is any nucleotide.
<220> FEATURE:
<221> NAME/KEY: misc_feature
<222> LOCATION: (147)..(147)
<223> OTHER INFORMATION: "n" is any nucleotide.

<400> SEQUENCE: 91
ttccgccaag caggaaaant cctcccctcc cccttggctc aaaggtggtg gttcctggcg      60
gggctgttcg tgatggtgtt gatccctcct tcccgggagc ctcccatggt cctaccctga     120
tccgggtggc acgaggaac ccaggancgt gccctgcgca ccgtctggag ctccggagat      180
gacaaggagc agctggtgaa gaacacatat gtcctgtgac cgccctgtcg ccaagaggac     240
```

<210> SEQ ID NO 92
<211> LENGTH: 390
<212> TYPE: DNA
<213> ORGANISM: Homo sapiens
<220> FEATURE:
<221> NAME/KEY: misc_feature
<222> LOCATION: (33)..(33)
<223> OTHER INFORMATION: "n" is any nucleotide.
<220> FEATURE:
<221> NAME/KEY: misc_feature
<222> LOCATION: (55)..(55)
<223> OTHER INFORMATION: "n" is any nucleotide.
<220> FEATURE:
<221> NAME/KEY: misc_feature
<222> LOCATION: (118)..(118)
<223> OTHER INFORMATION: "n" is any nucleotide.
<220> FEATURE:
<221> NAME/KEY: misc_feature
<222> LOCATION: (213)..(213)
<223> OTHER INFORMATION: "n" is any nucleotide.
<220> FEATURE:
<221> NAME/KEY: misc_feature
<222> LOCATION: (228)..(228)
<223> OTHER INFORMATION: "n" is any nucleotide.
<220> FEATURE:
<221> NAME/KEY: misc_feature
<222> LOCATION: (259)..(259)
<223> OTHER INFORMATION: "n" is any nucleotide.
<220> FEATURE:
<221> NAME/KEY: misc_feature
<222> LOCATION: (267)..(267)
<223> OTHER INFORMATION: "n" is any nucleotide.
<220> FEATURE:
<221> NAME/KEY: misc_feature
<222> LOCATION: (324)..(324)
<223> OTHER INFORMATION: "n" is any nucleotide.
<220> FEATURE:
<221> NAME/KEY: misc_feature
<222> LOCATION: (333)..(333)
<223> OTHER INFORMATION: "n" is any nucleotide.
<220> FEATURE:
<221> NAME/KEY: misc_feature
<222> LOCATION: (344)..(344)
<223> OTHER INFORMATION: "n" is any nucleotide.
<220> FEATURE:
<221> NAME/KEY: misc_feature
<222> LOCATION: (387)..(387)
<223> OTHER INFORMATION: "n" is any nucleotide.

<400> SEQUENCE: 92

```
tggggaaggg aggggagact atgtgtgagc ttttttaaa ta                    282 gagaggaact cctgcaataa cttcatctat ggnggctgcc ggggaataag aacanctacc  60
gctctgagga ggcctgcgtg ctccgctgct tccgctgtgt gttctcttcc aggccagcag  120
gagaatcctc ccctgcccct tggctcaaag gtggtggttc tggcggggct gttcgtgatg  180
gtgttgatcc tcttcctggg agcctccatg gtntacctga tccgggtngc acggaggaac  240
cagggagcgt gccctgcgna ccgtctngga gctccggaga tgacaaggag cagctggtga  300
agaacacata tgtcctgtga ccgncctgtt cgncaagagg actngggaa agggagggg   360 agattatgtg ttgagttttt tttaaantag                                  390
```

<210> SEQ ID NO 93
<211> LENGTH: 406
<212> TYPE: DNA
<213> ORGANISM: Homo sapiens
<220> FEATURE:
<221> NAME/KEY: misc_feature
<222> LOCATION: (306)..(306)
<223> OTHER INFORMATION: "n" is any nucleotide.
<220> FEATURE:

```
<221> NAME/KEY: misc_feature
<222> LOCATION: (328)..(328)
<223> OTHER INFORMATION: "n" is any nucleotide.
<220> FEATURE:
<221> NAME/KEY: misc_feature
<222> LOCATION: (342)..(342)
<223> OTHER INFORMATION: "n" is any nucleotide.
<220> FEATURE:
<221> NAME/KEY: misc_feature
<222> LOCATION: (365)..(365)
<223> OTHER INFORMATION: "n" is any nucleotide.
<220> FEATURE:
<221> NAME/KEY: misc_feature
<222> LOCATION: (370)..(370)
<223> OTHER INFORMATION: "n" is any nucleotide.
<220> FEATURE:
<221> NAME/KEY: misc_feature
<222> LOCATION: (377)..(377)
<223> OTHER INFORMATION: "n" is any nucleotide.
<220> FEATURE:
<221> NAME/KEY: misc_feature
<222> LOCATION: (382)..(382)
<223> OTHER INFORMATION: "n" is any nucleotide.
<220> FEATURE:
<221> NAME/KEY: misc_feature
<222> LOCATION: (402)..(402)
<223> OTHER INFORMATION: "n" is any nucleotide.

<400> SEQUENCE: 93
gattcggaac gaggagccgg ggcaataaga acagctaccg ctctgaggag gcctgcatgc      60
tccgctgctt ccgccagcag gagaatcctc ccctgcccct tggctcaaag gtggtggttc     120
tggcggggct gttcgtgatg gtgttgatcc tcttcctggg agcctccatg gtctacctga     180
tccgggtggc acggaggaac cagggagcgt gccctgcgca ccgtctggga gctccggaga     240
tgacaaggga gcagctggtg aagaacacat atgttcctgt tgaccgccct gttcgccaag     300
agggantggg ggaaggggag ggggaganta ttgttgttga gnttttttt aaaattagga     360 ggggnttgan ttcgggnttt tnagttgatc catttagggg gntgag                    406

<210> SEQ ID NO 94
<211> LENGTH: 360
<212> TYPE: DNA
<213> ORGANISM: Homo sapiens
<220> FEATURE:
<221> NAME/KEY: misc_feature
<222> LOCATION: (1)..(1)
<223> OTHER INFORMATION: "n" is any nucleotide.
<220> FEATURE:
<221> NAME/KEY: misc_feature
<222> LOCATION: (142)..(142)
<223> OTHER INFORMATION: "n" is any nucleotide.
<220> FEATURE:
<221> NAME/KEY: misc_feature
<222> LOCATION: (339)..(339)
<223> OTHER INFORMATION: "n" is any nucleotide.
<220> FEATURE:
<221> NAME/KEY: misc_feature
<222> LOCATION: (347)..(347)
<223> OTHER INFORMATION: "n" is any nucleotide.

<400> SEQUENCE: 94
nggccttgca gtgctccgct gcttccgcca gcaggagaat cctcccctgc cccttggctc      60
aaaggtggtg gttctggcgg ggctgttcgt gatggtgttg atcctcttcc tgggagcctc     120
catggtctac ctgatccggg tngcacggag gaaccaggag cgtgccctgc gcaccgtctg     180
gagctccgga gatgacaagg agcagctggt gaagaacaca tatgtcctgt gaccgccctg     240
tcgccaagag gactggggaa gggaggggag actatgtgtg agcttttttt aaatagaggg     300
attgactcgg atttgagtga tcattagggc tgaggtctnt ttctctngga ggtaggacga     360
```

<210> SEQ ID NO 95
<211> LENGTH: 438
<212> TYPE: DNA
<213> ORGANISM: Homo sapiens
<220> FEATURE:
<221> NAME/KEY: misc_feature
<222> LOCATION: (334)..(334)
<223> OTHER INFORMATION: "n" is any nucleotide.
<220> FEATURE:
<221> NAME/KEY: misc_feature
<222> LOCATION: (368)..(368)
<223> OTHER INFORMATION: "n" is any nucleotide.
<220> FEATURE:
<221> NAME/KEY: misc_feature
<222> LOCATION: (376)..(376)
<223> OTHER INFORMATION: "n" is any nucleotide.

<400> SEQUENCE: 95

| | | | | |
|---|---|---|---|---|
| cggggctgtt | cgtgatggtg | ttgatcctct | tcctgggagc | ctccatggtc | tacctgatcc | 60 |
| gggtggcacg | gaggaaccag | gagcgtgccc | tgcgcaccgt | ctggagctcc | ggagatgaca | 120 |
| aggagcagct | ggtgaagaac | acatatgtcc | tgtgaccgcc | ctgtcgccaa | gaggactggg | 180 |
| gaagggaggg | gagactatgt | gtgagctttt | tttaaataga | gggattgact | cggatttgag | 240 |
| tgatcattag | ggctgaggtc | tgtttctctg | ggaggtagga | cggctgcttc | ctgggtcttg | 300 |
| gcagggatgg | ggtttgcttt | gggaaatcct | cttngaggc | tcctccttcg | catgggcctt | 360 |
| gcagtctngg | cagcanccc | cgagtttttt | tccttcgctg | atccgatttc | ttttcctcca | 420 |
| ggtaagaatt | tttctttt | | | | | 438 |

<210> SEQ ID NO 96
<211> LENGTH: 448
<212> TYPE: DNA
<213> ORGANISM: Homo sapiens
<220> FEATURE:
<221> NAME/KEY: misc_feature
<222> LOCATION: (108)..(108)
<223> OTHER INFORMATION: "n" is any nucleotide.
<220> FEATURE:
<221> NAME/KEY: misc_feature
<222> LOCATION: (261)..(261)
<223> OTHER INFORMATION: "n" is any nucleotide.

<400> SEQUENCE: 96

| | | | | |
|---|---|---|---|---|
| gggaaccagg | agcgtgccct | gcgcaccggt | ctggagctcc | ggagatgaca | aggagcagct | 60 |
| ggtgaagaac | acatatgtcc | tgtgaccgcc | ctgtcgccaa | gaggactngg | gaagggaggg | 120 |
| gagactatgt | gtgagctttt | tttaaataga | gggattgact | cggatttgag | tgatcattag | 180 |
| ggctgaggtc | tgtttctctg | ggaggtagga | cggctgcttc | ctggtctggc | agggatgggt | 240 |
| ttgctttgga | gaatcctcta | ngaggctcct | cctcgcatgg | cctgcagtct | ggcagcagcc | 300 |
| ccgagttgtt | tcctcgctga | tcgatttctt | tcctccaggt | agagttttct | ttgcttatgt | 360 |
| tgaattccat | tgcctctttt | ctcatcacag | aagtgatgtt | ggaatcgttt | cttttgtttt | 420 |
| gtctgattta | tgggtttttt | ttaagtat | | | | 448 |

<210> SEQ ID NO 97
<211> LENGTH: 331
<212> TYPE: DNA
<213> ORGANISM: Homo sapiens
<220> FEATURE:
<221> NAME/KEY: misc_feature
<222> LOCATION: (20)..(20)
<223> OTHER INFORMATION: "n" is any nucleotide.
<220> FEATURE:

```
<221> NAME/KEY: misc_feature
<222> LOCATION: (30)..(30)
<223> OTHER INFORMATION: "n" is any nucleotide.

<400> SEQUENCE: 97
attagggctg aggtctgttn ctctgggagn taggacggct gccttcctgg tctggcaggg      60
atgggtttgc tttggaaatc ctctaggagg ctcctcctcg catggcctgc agttctgcag     120
cagccccgag ttgtttcctc gctgatcgat ttctttcctc caggtagagt tttctttgct     180
tatgttgaat tccattgcct cttttctcat cacagaagtg atgttggaat cgtttctttt     240
gtttgtctga tttatggttt ttttaagtat aaacaaaagt ttttattag cattctgaaa      300 gaaggaaagt aaaatgtaca agtttaataa a                                    331

<210> SEQ ID NO 98
<211> LENGTH: 373
<212> TYPE: DNA
<213> ORGANISM: Homo sapiens
<220> FEATURE:
<221> NAME/KEY: misc_feature
<222> LOCATION: (45)..(45)
<223> OTHER INFORMATION: "n" is any nucleotide.
<220> FEATURE:
<221> NAME/KEY: misc_feature
<222> LOCATION: (102)..(102)
<223> OTHER INFORMATION: "n" is any nucleotide.
<220> FEATURE:
<221> NAME/KEY: misc_feature
<222> LOCATION: (105)..(105)
<223> OTHER INFORMATION: "n" is any nucleotide.
<220> FEATURE:
<221> NAME/KEY: misc_feature
<222> LOCATION: (159)..(159)
<223> OTHER INFORMATION: "n" is any nucleotide.
<220> FEATURE:
<221> NAME/KEY: misc_feature
<222> LOCATION: (174)..(174)
<223> OTHER INFORMATION: "n" is any nucleotide.
<220> FEATURE:
<221> NAME/KEY: misc_feature
<222> LOCATION: (213)..(213)
<223> OTHER INFORMATION: "n" is any nucleotide.
<220> FEATURE:
<221> NAME/KEY: misc_feature
<222> LOCATION: (337)..(337)
<223> OTHER INFORMATION: "n" is any nucleotide.

<400> SEQUENCE: 98
gattgactcg gatttgagtg atcattaggg ctgaggtctg tttcnctggg aggtaggacg      60
gctgctcccc tggtctggca gggatgggtt tgctttggaa anccnctagg aggctcctcc     120
tcgcatggcc tgcagtctgg cagcagcccc gagttgttnc ctcgctgatc gatntctttc     180
ccccaggtag agttttcttt gcttatgttg aantccattg cctctttcct catcacagaa     240
gtgatgttgg aatcgtttct tttgtttgtc tgatttatgg ttttttttaag tataaacaaa     300 agttttttat tagcattctg aaagaaggaa agtaaantgt acaagtttaa taaaagggg      360 ccttccccctt taa                                                       373

<210> SEQ ID NO 99
<211> LENGTH: 380
<212> TYPE: DNA
<213> ORGANISM: Homo sapiens

<400> SEQUENCE: 99
gattgactcg gatttggagt gatcattagg gctgaggtct gtttctctgg gaggtaggac      60
ggctgcttcc tggtctggca gggatgggtt tgctttggaa atcctctagg aggctcctcc     120
```

```
ttcgcatggc ctgcagtctg gcagcagccc cgagttgttt cctcgctgat cgatttcttt    180
cctccaggta gagttttctt tgcttatgtt gaattccatt gcctcttttc tcatcacaga    240
agtgatgttg gaatcgtttc ttttgtttgt ctgatttatg gttttttaa gtataaacaa    300 aagttttta ttagcattct gaaagaagga agtaaaatg tacaagttta ataaaaaggg    360
gccttcccct ttagaataaa                                               380
```

<210> SEQ ID NO 100
<211> LENGTH: 320
<212> TYPE: DNA
<213> ORGANISM: Homo sapiens
<220> FEATURE:
<221> NAME/KEY: misc_feature
<222> LOCATION: (304)..(304)
<223> OTHER INFORMATION: "n" is any nucleotide.
<220> FEATURE:
<221> NAME/KEY: misc_feature
<222> LOCATION: (309)..(309)
<223> OTHER INFORMATION: "n" is any nucleotide.

<400> SEQUENCE: 100

```
tctggcaggg atgggtttgc tttggaaatc ctctaggagg ctcctcctcg catggcctgc    60
agtctggcag cagcccgagt tgtttcctcg ctgatcgatt tctttcctcc aggtagagtt   120
ttctttgctt atgttgaatt ccattgcctc ttttctcatc acagaagtga tgttggaatc   180
gtttcttttg tttgtctgat ttatggtttt tttaagtata acaaaagtt ttattagc    240 attctgaaag aaggaaagta aaatgtacaa gtttaataaa aaggggcctt ccccctttagg   300 aatnaaaana aaaagggtg                                                320
```

<210> SEQ ID NO 101
<211> LENGTH: 397
<212> TYPE: DNA
<213> ORGANISM: Homo sapiens
<220> FEATURE:
<221> NAME/KEY: misc_feature
<222> LOCATION: (24)..(24)
<223> OTHER INFORMATION: "n" is any nucleotide.

<400> SEQUENCE: 101

```
gattgactcg gatttgagtg atcnattagg gctgaggtct gtttctctgg gaggtaggac    60
ggctgcttca tggtctggca gggatggtt tgctttggaa atcctctagg aggctcctcc   120
tcgcatggcc tgcagtctgc agcagccccg agttgtttcc tcgctgatcg atttcttcc   180 tccaggtaga gttttctttg cttatgttga attccattgc ctcttttctc atcacagaag   240
tgatgttgga atcgtttctt ttgtttgtct gatttatggt ttttttaagt ataaacaaaa   300
gttttttatt agcattctga agaaggaaa gtaaaatgta caagtttaat aaaaagggc   360 cttccccttt agaataaatt tcagcatgtg ctttcaa                            397
```

<210> SEQ ID NO 102
<211> LENGTH: 289
<212> TYPE: DNA
<213> ORGANISM: Homo sapiens
<220> FEATURE:
<221> NAME/KEY: misc_feature
<222> LOCATION: (61)..(61)
<223> OTHER INFORMATION: "n" is any nucleotide.
<220> FEATURE:
<221> NAME/KEY: misc_feature
<222> LOCATION: (74)..(74)
<223> OTHER INFORMATION: "n" is any nucleotide.
<220> FEATURE:

```
<221> NAME/KEY: misc_feature
<222> LOCATION: (122)..(122)
<223> OTHER INFORMATION: "n" is any nucleotide.
<220> FEATURE:
<221> NAME/KEY: misc_feature
<222> LOCATION: (184)..(184)
<223> OTHER INFORMATION: "n" is any nucleotide.

<400> SEQUENCE: 102
gaggctcctc ctcgcatggc ctgcagtctt ggcagcagcc ccgagttgtt tcctcgctga      60
ncgatttctt tccnccaggt agagttttct ttgcttatgt tgaattccat tgcctctttt     120
cncatcacag aagtgatgtt ggaatcgttt cttttgtttg tctgatttat ggtttttta     180 agtntaaaca aaagtttttt attagcattc tgaagaagg aaagtaaaat gtacaagttt      240
aataaaaagg ggccttcccc tttagaataa aaaaaaaaa aaaaaaaa                   289

<210> SEQ ID NO 103
<211> LENGTH: 311
<212> TYPE: DNA
<213> ORGANISM: Homo sapiens
<220> FEATURE:
<221> NAME/KEY: misc_feature
<222> LOCATION: (7)..(7)
<223> OTHER INFORMATION: "n" is any nucleotide.

<400> SEQUENCE: 103
cttttgnaaa tcctctagga ggctcctcct cgcatggcct gcagtctgca gcagccccga     60
gttgtttcct cgctgatcgg atttctttcc tccaggtaga gttttctttg cttatgttga    120
attccattgc ctcttttctc atcacagaag tgatgttgga atcgtttctt ttgtttgtct    180
gatttatggt ttttttaagt ataaacaaaa gttttttatt agcattctga agaaggaaa    240 gtaaatgta caagtttaat aaaagggggc cttcccctt agaataaatt tcagcatgtg     300
ctttcaaaaa a                                                         311

<210> SEQ ID NO 104
<211> LENGTH: 338
<212> TYPE: DNA
<213> ORGANISM: Homo sapiens
<220> FEATURE:
<221> NAME/KEY: misc_feature
<222> LOCATION: (32)..(32)
<223> OTHER INFORMATION: "n" is any nucleotide.
<220> FEATURE:
<221> NAME/KEY: misc_feature
<222> LOCATION: (67)..(67)
<223> OTHER INFORMATION: "n" is any nucleotide.
<220> FEATURE:
<221> NAME/KEY: misc_feature
<222> LOCATION: (136)..(136)
<223> OTHER INFORMATION: "n" is any nucleotide.

<400> SEQUENCE: 104
ggtctggcag ggatgggttt gcctttggaa ancctctagg aggctcctcc tcgcatggcc     60
tgcagtnctg gcagcagacc ccgagttgtt tcctcgctga tcgatttctt tacccccagg    120
tagagttttc ctttgncta tgttgaattc cattgcctct tttactcatc acagaagtga     180
tgttggaatc gtttcttttg tttgtctgat ttatggtttt tttaagtata aacaaaagtt     240
ttttattagc attctgaaag aaggaaagta aaatgtacaa gtttaataaa aaggggcctt    300
cccctttaga ataaaaaaaa aaaaaaaaa aaaaaaa                              338

<210> SEQ ID NO 105
<211> LENGTH: 343
```

```
<212> TYPE: DNA
<213> ORGANISM: Homo sapiens
<220> FEATURE:
<221> NAME/KEY: misc_feature
<222> LOCATION: (13)..(13)
<223> OTHER INFORMATION: "n" is any nucleotide.
<220> FEATURE:
<221> NAME/KEY: misc_feature
<222> LOCATION: (19)..(19)
<223> OTHER INFORMATION: "n" is any nucleotide.
<220> FEATURE:
<221> NAME/KEY: misc_feature
<222> LOCATION: (107)..(107)
<223> OTHER INFORMATION: "n" is any nucleotide.

<400> SEQUENCE: 105
ccctgggtcc tgncaaggna tggggtttgc tttggaaatc ctcttaggag gctcctcctc      60
gcatggcctg cagtctggca gcagccccga gttgtttcct cgctgancga tttctttcct    120
ccaggtagag ttttctttgc ttatgttgaa ttccattgcc tcttttctca tcacagaagt    180
gatgttggaa tcgtttcttt tgtttgtctg atttatggtt tttttaagta taaacaaaag    240
ttttttatta gcattctgaa agaaggaaag taaaatgtac aagtttaata aaaagggggcc   300
ttccccttta gaataaaaaa aaaaaaaaaa aaaaaaaaa aaa                       343
```

What is claimed is:

1. A functionalized heparin-binding protein comprising a heparin-binding protein and at least one sugar chain covalently bonded thereto,
   said at least one covalently bonded sugar chain being selected from the group consisting of a sulfated polysaccharide, a glycosaminoglycan and an O-linked sugar chain,
   said heparin-binding protein comprising (a) a proteoglycan core protein or a part thereof, to which said sugar chain is bonded, and (b) the portion of the amino acid sequence of SEQ ID NO: 1 starting with Asn at number 88 and ending with Asp at number 221,
   wherein the DNA synthesis promoting activity of the heparin-binding protein is increased by adding the at least one covalently bonded sugar chain.

2. The functionalized heparin-binding protein of claim 1, wherein the at least one sugar chain is heparan sulfate.

3. The functionalized heparin-binding protein of claim 1, wherein the functionalized heparin-binding protein has improved stability over an unmodified heparin-binding protein.

4. The functionalized heparin-binding protein of claim 3, wherein the stability is chosen from among the group consisting of thermostability, acid resistance, alkalai resistance and resistance to proteolytic enzymes.

5. A pharmaceutical composition containing the functionalized heparin-binding protein of claim 1 as an active ingredient.

* * * * *

UNITED STATES PATENT AND TRADEMARK OFFICE
CERTIFICATE OF CORRECTION

| | | |
|---|---|---|
| PATENT NO. | : 7,005,415 B1 | Page 1 of 25 |
| APPLICATION NO. | : 09/121017 | |
| DATED | : February 28, 2006 | |
| INVENTOR(S) | : Imamura et al. | |

It is certified that error appears in the above-identified patent and that said Letters Patent is hereby corrected as shown below:

Please delete column 1 line 1 through column 100 line 41 and insert column 1 line 1 through column 48 line 62 as attached Signed and Sealed this
Twenty-eighth Day of December, 2010

David J. Kappos
*Director of the United States Patent and Trademark Office*

HEPARIN-BINDING PROTEINS MODIFIED WITH SUGAR CHAINS, METHOD OF PRODUCING THE SAME AND PHARMACEUTICAL COMPOSITIONS CONTAINING THE SAME

BACKGROUND OF THE INVENTION

The present invention relates to a heparin-binding protein functionalized by covalently bonding thereto sugar chain(s), a method for producing the protein and a pharmaceutical composition containing the protein.

It has been known that heparin-binding proteins, among all, those proteins classified into the fibroblast growth factor (hereinafter, referred to as "FGF") family and fibroblast growth factor homologous factors strongly bind to heparin and heparan sulfate (sulfated polysaccharides) by a non-covalent bond. It has been also known that when a heparin-binding protein such as fibroblast growth factor is mixed with a sulfated polysaccharide such as heparin, the biological activity and physical properties of the heparin-binding protein are altered to change its function; sometimes, such a heparin-binding protein may acquire higher function. However, even if a sulfated polysaccharide was mixed with, the expected functionalization of the protein has been limited. Besides, when such a mixture is used as a pharmaceutical composition, unfavorable physiological activity attributable to a free sulfated polysaccharide has caused a problem. To date, there has been reported no protein in which a heparin-binding protein is joined with sulfated polysaccharide(s) by a covalent bond for the purpose of functionalization of the heparin-binding protein.

In addition, it has never been known to date that artificial addition of asparagine-linked sugar chain(s) (hereinafter, referred to as "N-linked sugar chain(s)") or serine/threonine-linked sugar chain(s) (hereinafter, referred to as an "O-linked sugar chain(s)") to a heparin-binding protein, particularly a protein of the FGF family or a fibroblast growth factor homologous factor, by covalent bond(s) can functionalize the protein. Furthermore, the general effect which N-linked sugar chain(s) or O-linked sugar chain(s) could give has not been known. Exceptionally, with respect to FGF-6, the role of the N-linked sugar chain(s) it naturally has was suggested in an in vitro translation system, but has not been proved directly. To date, there has been reported no example of joining a heparin-binding protein with N-linked or O-linked sugar chain(s) by covalent bond(s) for the purpose of functionalizing the heparin-binding protein.

It is an object of the present invention to improve the function of heparin-binding proteins. It is another object of the invention to establish a heparin-binding protein to which sugar chain(s) are covalently bonded and a method for producing the protein. It is still another object of the invention to provide a pharmaceutical composition containing the above protein.

SUMMARY OF THE INVENTION

The present inventors have made intensive and extensive researches toward the solution of the above problems. As a result, the inventors have noted the fact that sulfated polysaccharide(s), glycosaminoglycan(s), N-linked sugar chain(s) and O-linked sugar chain(s) are individually synthesized in living animal bodies as sugar chain(s) of a glycoprotein. Then, the inventors have found that it is possible to produce a heparin-binding protein having in its molecule sulfated polysaccharide(s), glycosaminoglycan(s), N-linked sugar chain(s) or O-linked sugar chain(s) covalently bonded thereto by ensuring that a cDNA coding for a peptide to which any of the above sugar chains can be added is ligated to a cDNA coding for the heparin-binding protein, and by then allowing an animal cell to produce the gene product of the ligated cDNA. Furthermore, the inventors have confirmed that the function of the resultant sugar chain(s)-added heparin-binding protein is improved. Thus, the present invention has been achieved based on these findings.

The present invention provides a heparin-binding protein functionalized by covalently bonding thereto sugar chain(s). The sugar chain(s) may be selected from the group consisting of sulfated polysaccharide(s), glycosaminoglycan(s), N-linked sugar chain(s), O-linked sugar chain(s) and a combination thereof. The heparin-binding protein may be a factor belonging to the FGF family or its allied factor. The heparin-binding protein may be covalently bonded to the sugar chain(s) through a peptide to which the sugar chain(s) can be added. For example, the heparin-binding protein to which the sugar chain(s) are to be covalently bonded may be the following (a) or (b):

(a) a protein consisting of the amino acid sequence of SEQ ID NO: 1, 3, 5, 17, 19, 21, 23, 25, 27 or 29;

(b) a protein which consists of the amino acid sequence of SEQ ID NO:1, 3, 5, 17, 19, 21, 23, 25, 27 or 29 having deletion, substitution, addition or modification of one or several amino acids, which has FGF activity and to which the sugar chain can be added.

In the heparin-binding protein of the invention, the sugar chain(s) may be bonded to the heparin-binding protein at a site forming a turn in the secondary structure or a site near one of the ends, or a site which would not change the tertiary structure of the protein greatly by addition of the sugar chain(s).

The present invention also provides a method for producing a heparin-binding protein functionalized by covalently bonding thereto sugar chain(s), comprising the following steps:

(a) a step in which a cDNA coding for a peptide to which sugar chain(s) can be added is ligated to a cDNA coding for a heparin-binding protein;

(b) a step of incorporating the resultant ligated cDNA into an expression vector;

(c) a step of introducing the expression vector into a host cell having sugar chain(s) addition pathway; and (d) a step of expressing in the host cell a heparin-binding protein to which sugar chain(s) are covalently bonded through the peptide to which the sugar chain(s) can be added.

When the sugar chain(s) are sulfated polysaccharide(s) or glycosaminoglycan(s), the peptide to which the sugar chain(s) can be added may be a proteoglycan core protein or a part thereof. When the sugar chain(s) are N-linked sugar chain(s), the peptide to which the sugar chain(s) can be added may be a peptide comprising N-linked sugar chain(s)-added amino acid sequence. When the sugar chain(s) are O-linked sugar chain(s), the peptide to which the sugar chain(s) can be added may be a peptide comprising O-linked sugar chain(s)-added amino acid sequence. The present invention also provides a method for producing a heparin-binding protein functionalized by covalently bonding thereto sugar chain(s), comprising a step of allowing the sugar chain(s) to bind to the heparin-binding protein by a chemical binding method. The sugar chain(s) may be selected from the group consisting of sulfated polysaccharide(s), glycosaminoglycan(s), N-linked sugar chain(s), O-linked sugar chain(s) and a combination thereof, and the heparin-binding protein may be a factor belonging to the FGF family or its allied factor. The present invention further provides a pharmaceutical composition containing, as an active ingredient, a heparin-binding protein functionalized by covalently bonding thereto sugar chain(s). The present invention also provides a method for functionalizing a natural protein having no sugar chain(s) by covalently bonding thereto sugar chain(s).

The novel sugar chain(s)-added heparin-binding protein of the invention is excellent in stabilities such as thermostability, acid resistance, alkali resistance and resistance to proteolytic enzymes. Thus, by using the sugar chain(s)-added heparin-binding protein of the invention in a pharmaceutical product, it is possible to design such a pharmaceutical product that is excellent in in vivo stabilities, in particular acid resistance and alkali resistance, and applicable to an oral medicine.

BRIEF DESCRIPTION OF THE DRAWINGS

FIG. 1 shows typical examples of sulfated polysaccharide and glycosaminoglycan sugar chains.

FIG. 2 shows typical examples of N-linked sugar chains.

FIG. 3 shows typical examples of O-linked sugar chains.

FIG. 4A shows SDS-denatured electrophoregrams of S/FGF-1a-II Protein.

FIG. 4B shows SDS-denatured electrophoregrams of N-FGF-1a-IV and O-FGF-1a Proteins.

FIG. 5A shows the DNA synthesis promoting activity on HUVEC of S/FGF-1a-II.

FIG. 5B shows the DNA synthesis promoting activity on HUVEC of E. coli-derived FGF-1a.

FIG. 6A shows the thermostability, acid resistance and alkali resistance of S/FGF-1a-II.

FIG. 6B shows the thermostability, acid resistance and alkali resistance of E. coli-derived FGF-1a.

FIG. 7 shows the resistance to trypsin of S/FGF-1a-II and E. coli-derived FGF-1a.

FIG. 8 shows the DNA synthesis promoting activity on HUVEC of N-FGF-6/1a-IV and E. coli-derived FGF-1a.

FIG. 9 shows the heparin affinity of S/FGF-1a-II.

DESCRIPTION OF PREFERRED EMBODIMENTS

Hereinbelow, the present invention will be described in detail.

In the present invention, the heparin-binding protein to which sugar chain(s) are to be covalently bonded is a protein having heparin binding property. For example, factors belonging to the FGF family or allied factors, or other proteins with heparin-binding property but without structural similarity to the former proteins may be enumerated. Examples of the other proteins include, but are not limited to, heparin-binding epidermal growth factor-like factor (HB-EGF) and platelet-derived growth factor (PDGF). As specific examples of the factors belonging to the FGF family or allied factors, FGF-1 to −10 and FHF (fibroblast growth factor homologous factor)-1 to −4 are known. The heparin-binding protein of the invention may be covalently bonded to sugar chain(s) through a peptide to which the sugar chain(s) can be added. For example, the heparin-binding protein to which the sugar chain(s) are to be covalently bonded may be the following (a) or (b):

(a) a protein consisting of the amino acid sequence of SEQ ID NO: 1, 3, 5, 17, 19, 21, 23, 25, 27 or 29;

(b) a protein which consists of the amino acid sequence of SEQ ID NO: 1, 3, 5, 17, 19, 21, 23, 25, 27 or 29 having deletion, substitution, addition or modification of one or several amino acids, which has FGF activity and to which the sugar chain(s) can be added.

Proteins having the amino acid sequences of SEQ ID NOS: 1, 3, 5, 17, 19, 21, 23, 25, 27 and 29 are encoded by, for example, the DNA sequences of SEQ ID NOS: 2, 4, 6, 18, 20, 22, 24, 26, 28 and 30, respectively. These proteins contain a peptide sequence to which sugar chain(s) can be added and a sequence for a signal peptide in addition to a peptide sequence for a factor belonging to the FGF family. The heparin-binding protein of the present invention includes not only the protein primarily defined by a cDNA shown in the sequence listing but also a protein in which a peptide sequence for secretion (called the signal peptide) located at the amino terminal when secreted from cells is cut off. The utility of a heparin-binding protein which is contained in the pharmaceutical composition of the invention as an active ingredient will not vary even if the protein is produced in a form lacking the signal peptide from the beginning.

The sugar chain(s) to be covalently bonded to the heparin-binding protein may be any sugar chain(s) as long as the protein is functionalized by covalently bonding the sugar chain(s). Examples of the sugar chain(s) include, but are not limited to, sulfated polysaccharides such as heparan sulfate, chondroitin sulfate, glycosaminoglycans, N-linked sugar chains and O-linked sugar chains. The term "functionalize" used herein means increasing the activity of a protein of interest. As an example of functionalization, there may be given a case in which the residual activity of a protein after treatment with heat, acid or alkali is increased by adding sugar chain(s) to the protein by covalent bond(s). The "sulfated polysaccharide(s)" used herein is a general term for various sugar chain structures which are elongating from xylose linked to a serine residue present in the primary structure of proteins or elongating on the non-reducing end side of N-linked sugar chains or O-linked sugar chains to be described later, or which are present in a free form.

Many of such sugar chains are composed of repeating disaccharides of aminosugar and uronic acid (or galactose), and some of their hydroxyl groups or amino groups are substituted with sulfate groups. Glycosaminoglycans are polysaccharides having a structure similar to those described above, but they include those which do not have any substitution with sulfate groups. All of the above-mentioned polysaccharides are designated herein generically "sulfated polysaccharides or the like".

Their specific structures are described, for example, in Destiny of Sugar Chains in Cells, Nagai, Hakomori and Kobata (Eds.), Kodansha Scientific Co. FIG. 1 shows their typical sugar chain sequences. The "N-linked sugar chain(s)" used herein is a general term for various sugar chain(s) structures elongating from N-acetylglucosamine linked to an asparagine residue present in the primary structure of proteins. Their specific structures are described, for example, in Destiny of Sugar Chains in Cells, Nagai, Hakomori and Kobata (Eds.), Kodansha Scientific Co. FIG. 2 shows their typical sugar chain sequences. The "O-linked sugar chain(s)" used herein is a general term for various sugar chain(s) structures elongating from N-acetylgalactosamine linked to a serine or threonine residue present in the primary structure of proteins. Their specific structures are described, for example, in Destiny of Sugar Chains in Cells, Nagai, Hakomori and Kobata (Eds.), Kodansha Scientific Co. FIG. 3 shows their typical sugar chain sequences. These sulfated polysaccharides or the like, N-linked sugar chains and O-linked sugar chains may have addition, deletion, substitution or modification in a part of their sugar chain sequences as long as they retain their functions.

When sugar chain(s) are attached to a heparin-binding protein, the sugar chain(s) alone may be covalently bonded to the heparin-binding protein directly. Alternatively, a peptide chain of any length to which sugar chain(s) are covalently bonding may be covalently bonded to a heparin-binding protein.

In order to produce the heparin-binding protein of the invention to which sugar chain(s) are covalently bonded (hereinafter, referred to as the "sugar chain(s)-added heparin-binding protein"), first, a cDNA coding for a peptide to which sugar chain(s) can be added is ligated to a cDNA coding for a heparin-binding protein. The ligated cDNA is incorporated into an appropriate expression vector, which is then introduced into a host cell having sugar chain(s) addition pathway to thereby express sugar chain(s)-added heparin-binding protein.

cDNAs coding for various heparin-binding proteins can be obtained by designing appropriate primers from a sequence registered in a gene bank such as DDBJ (DNA Data Bank of Japan) and performing RT-PCR (reverse transcription PCR) with the primers and mRNA from the relevant tissue of the relevant animal.

In order to produce a sulfated polysaccharide or the like-added heparin-binding protein, first, a cDNA coding for a heparin-binding protein is ligated to a cDNA coding for a peptide which is known to undergo addition of a sulfated polysaccharide or the like. The ligated cDNA is incorporated into an appropriate host cell expression vector, which is then introduced into a host cell to thereby express the sulfated polysaccharide or the like-added heparin-binding protein. As the peptide which is known to undergo addition of a sulfated polysaccharide or the like, the core protein or a part thereof of various proteoglycans (e.g. syndecan, glypican, perlecan) may be used. As a part of the core protein of a proteoglycan, a peptide comprising a Ser-Gly repeat sequence (which is believed to be the sugar chain(s) addition site in proteoglycans) may be used.

In order to produce an N-linked sugar chain(s)-added heparin-binding protein, first, a cDNA coding for a heparin-binding protein is ligated to a cDNA coding for a peptide which is known to undergo addition of N-linked sugar chain(s). The ligated cDNA is incorporated into an appropriate host cell expression vector, which is then introduced into a host cell to thereby express the N-linked sugar chain(s)-added heparin-binding protein. Specific examples of the peptide which is known to undergo addition of N-linked sugar chain(s) include Asn-X-Thr and Asn-X-Ser (wherein X is any amino acid except proline).

In order to produce O-linked sugar chain(s)-added heparin-binding protein, first, a cDNA coding for a heparin-binding protein is ligated to a cDNA coding for a peptide which is known to undergo addition of O-linked sugar chain(s). The ligated cDNA is incorporated into an appropriate host cell expression vector, which is then introduced into a host cell to thereby express the O-linked sugar chain(s)-added heparin-binding protein. As a specific examples of the peptide which is known to undergo addition of O-linked sugar chain(s), Ala-Thr-Pro-Ala-Pro may be given.

As the site to which sugar chain(s) are bonded, a site forming a turn in the secondary structure of a heparin-binding protein or a site near one of the ends, or a site which would not change the tertiary structure of the protein greatly by addition of the sugar chain(s) is preferable.

One example of the method for producing sugar chain(s)-added heparin-binding protein of the invention will be described below.

First, an oligonucleotide coding for a secretion signal and a peptide which is known to undergo addition of sugar chain(s) is synthesized or amplified by PCR. The resultant oligonucleotide is incorporated at the 5' end of a plasmid coding for a heparin-binding protein.

As the secretion signal and the peptide which is known to undergo addition of sugar chain(s), an amino terminal of a typical secretion-type glycoprotein may be used, for example. Specifically, the amino acid consisting of the N terminal 40 residues of mouse FGF-6 may be used.

The plasmid coding for a heparin-binding protein can be prepared by incorporating a DNA coding for the heparin-binding protein into an appropriate plasmid. As the plasmid into which a DNA coding for a heparin-binding protein is to be incorporated, any plasmid may be used as long as it is replicated and maintained in a host. For example, pBR322 and pUC18 from E. coli and pET-3c which was constructed based on these plasmids may be enumerated.

As a method for incorporating the above-described oligonucleotide into the plasmid coding for a heparin-binding protein, the method described in T. Maniatis et al.: Molecular Cloning, Cold Spring Harbor Laboratory, p. 239 (1982) may be given, for example.

From the thus prepared plasmid, a region comprising a nucleotide sequence coding for a secretion signal, a peptide which is known to undergo addition of sugar chain(s) and a heparin-binding protein (hereinafter, referred to as a "region comprising a nucleotide sequence coding for sugar chain(s)-added heparin-binding protein") is cut out. This region is ligated to the downstream of a promoter in a vector suitable for expression to thereby obtain an expression vector.

The above-described region comprising a nucleotide sequence coding for sugar chain(s)-added heparin-binding protein may have ATG at its 5' end as a translation initiation codon and TAA, TGA or TAG at its 3' end as a translation termination codon. In order to express the protein encoded in the coding region, a promoter is ligated to the upstream of the region. As the promoter to be used in the present invention, any promoter may be used as long as it is appropriate to the host used for the expression of the gene. When the host to be transformed is a *bacillus*, SPO1 promoter, SPO2 promoter, penP promoter or the like may be used. When the host is a yeast, PHO5 promoter, PGK promoter, GAP promoter, ADH promoter or the like may be used. When the host is an animal cell, a promoter from SV40 or a promoter from a retrovirus may be used.

As the plasmid into which the thus constructed recombinant DNA comprising a nucleotide sequence coding for sugar chain(s)-added heparin-binding protein is to be incorporated, any plasmid may be used as long as it can be expressed in the host cell. For example, those vectors which were constructed based on E. coli-derived pBR322 and pUC18 may be given.

As a method for incorporating the recombinant DNA into a plasmid, the method described in T. Maniatis et al.: *Molecular Cloning*, Cold Spring Harbor Laboratory, p. 239 (1982) may be given, for example.

By introducing a vector comprising the above-described recombinant DNA into a host cell, a transformant carrying the vector is prepared.

As the host cell, any cell may be used as long as it has sugar chain(s) addition pathway. Specific examples include, but are not limited to, bacilli (e.g. *Bacillus subtilis* DB105), yeasts (e.g. *Pichia pastoris, Saccharomyces cerevisiae*), animal cells (e.g. COS cell, CHO cell, BHK cell, NIH3T3 cell, BALB/c3T3 cell, HUVE cell, LEII cell) and insect cells (e.g. SF-9 cell, Tn cell).

The above-mentioned transformation may be performed by a conventional method commonly used for each host. Alternatively, an applicable method may be used though it is not commonly used. For example, when the host is a yeast, a vector comprising the recombinant DNA is introduced into competent cells (prepared by the lithium method or the like) by the temperature shock method or electroporation. When the host is an animal cell, a vector comprising the recombinant DNA is introduced into cells at the logarithmic growth phase or the like by the calcium phosphate method, lipofection or electroporation.

By culturing the thus obtained transformant in a medium, a sugar chain(s)-added heparin-binding protein is produced. As the medium for culturing the transformant, a conventional medium commonly used for each host may be used. Alternatively, an applicable medium may be used even if it is not commonly used. For example, when the host is a yeast, YPD medium or the like may be used. When the host is an animal cell, Dulbecco's MEM supplemented with animal serum, or the like may be used. The cultivation may be performed under conditions commonly employed for each host. Alternatively, applicable conditions may be used even if they are not commonly used. For example, when the host is a yeast, the cultivation is carried out at about 25–37° C. for about 12 hours to 2 weeks. If necessary, aeration or agitation may be carried out. When the host is an animal cell, the cultivation is carried out at about 32–37° C. under 5% $CO_2$ and 100% humidity for about 24 hours to 2 weeks. If necessary, the conditions of the gas phase may be changed or agitation may be carried out.

In order to obtain a sugar-chain(s) added heparin-binding protein from the culture of the above-described transformant, the protein released into the culture fluid may be directly recovered from a supernatant after centrifugation. Alternatively, when the protein is to be extracted from the cultured microorganisms or cells, the protein may be obtained by disrupting the cultured microorganisms or cells with a homogenizer, a French press, ultrasonic waves, lysozyme and/or by freeze-thawing to thereby elute the protein of interest to the outside of the cells, and then recovering the protein from soluble fractions. If the protein of interest is contained in insoluble fractions, insoluble fractions may be recovered by centrifugation after disruption of the microorganisms or cells and then solubilized with a buffer containing guanidine hydrochloride or the like, to thereby recover the protein of interest from the resultant soluble fractions. Alternatively, the cultured microorganisms or cells may be disrupted by a direct treatment with a buffer containing a protein denaturing agent such as guanidine hydrochloride to thereby elute the protein of interest to the outside of the cells.

In order to purify a sugar chain(s)-added heparin-binding protein from the above-mentioned supernatant, known separation/purification methods may be used in an appropriate combination. Specific examples of these known separation/purification methods include salting out, solvent precipitation, dialysis, ultrafiltration, gel filtration, SDS-polyacrylamide gel electrophoresis, ion exchange chromatography, affinity chromatography, reversed phase high performance liquid chromatography and isoelectric focusing. Further, affinity chromatography using heparin sepharose as a carrier may be applicable to a large number of heparin-binding proteins.

The thus obtained sample may be dialyzed and freeze-dried to obtain dry powder if the activity of the sugar chain(s)-added heparin-binding protein is not damaged by such processing. Further, in storing the sample, addition of serum albumin to the sample is effective for preventing adsorption of the sample to the container.

The inclusion of an extremely small amount of a reducing agent in the purification process or the storing process is preferable for preventing oxidation of the sample. As the reducing agent, β-mercaptoethanol, dithiothreitol, glutathione or the like may be used.

The sugar chain(s)-added heparin-binding protein of the invention may also be produced by attaching sugar chain(s) to a heparin-binding protein by a chemical method. As the specific method, the following a) or b), or a combination thereof may be used.

a) For example, first, sugar chain(s) are completed by a biological method, a chemical synthesis method or a combination thereof. At that time, a residue appropriate for protein binding may be introduced at one end of the sugar chain(s). For example, an aldehyde group is formed by reducing and partially oxidizing the reducing end of the completed sugar chain(s). Then, this aldehyde group is attached to an amino group in a protein by an amino bond to thereby complete the joining of the sugar chain(s) and the protein.

b) For example, first, an aldehyde group is formed by reducing and partially oxidizing the reducing end of a monosaccharide or a residue appropriate for protein binding which is bound to a monosaccharide. Then, this aldehyde group is attached to an amino group in a protein by an amino bond to thereby complete the joining of the monosaccharide and the protein. An additional monosaccharide or sugar chain(s) are attached to a hydroxyl group or the like of the above monosaccharide to thereby complete sugar chain(s). For this attachment, a biological method, a chemical synthesis method or a combination thereof may be considered.

A heparin-binding protein functionalized by covalently bonding thereto sugar chain(s) can be used as a medicine. For example, the sugar chain(s)-added heparin-binding protein of the invention regulates the physiological function of FGF. Specifically, the physiological function of FGF is to promote or inhibit the growth of fibroblast, vascular endothelial cell, myoblast, cartilage cell, osteoblast and glia cell. Therefore, the sugar chain(s)-added heparin-binding protein of the invention is effective for promoting cell growth and tissue regeneration in liver or the like; for curing wounds and regulating nervous function; and for regulating the growth of fibroblast or the like. The protein of the invention is useful for preventing or treating various diseases such as fibroblastoma, angioma, osteoblastoma, death of neurocytes, Alzheimer's disease, Parkinson's disease, neuroblastoma, amnesia, demensia and myocardial infarction. The protein of the invention can also be used as a trichogenous agent or a hair-growing agent.

The sugar chain(s)-added heparin-binding protein obtained as described above may be formulated into pharmaceutical compositions such as liquid, lotions, aerosols, injections, powder, granules, tablets, suppositories, enteric coated tablets and capsule, by mixing the protein with pharmaceutically acceptable solvents, vehicles, carriers, adjuvants, etc. according to conventional formulation methods.

The content of the sugar chain(s)-added heparin-binding protein, which is an active ingredient, in the pharmaceutical composition may be about 0.0000000001 to 1.0% by weight.

The pharmaceutical composition can be administered parenterally or orally to mammals, e.g. human, mouse, rat, rabbit, dog, cat, etc. in a safe manner. The dose of the pharmaceutical composition may be appropriately changed depending on the dosage form, administration route, conditions of the patient and the like. For example, for administration to mammals including human, 0.0001 to 100 mg of the sugar chain(s)-added heparin-binding protein may be applied to the diseased part several times a day.

The present invention has been described so far taking heparin-binding proteins as an example. However, it should be noted that besides the heparin-binding proteins, natural proteins having no sugar chain(s) can also be functionalized by covalently bonding thereto sugar chain(s).

Deposit of Microorganisms

Clones of *E. coli* DH5 α carrying plasmids incorporating genes coding for the sugar chain(s)-added heparin-binding proteins of the invention (having the DNA sequences of SEQ ID NOS: 2, 4, 18, 20, 22, 24, 26, 28 and 30, respectively) were deposited at the National Institute of Bioscience and Human-technology, Agency of Industrial Science and Technology under Accession Numbers of FERM BP-6428, FERM BP-6424, FERM BP-6427, FERM BP-6431, FERM BP-6429, FERM BP-6430, FERM BP-6423, FERM BP-1625 and FERM BP-6426 on Sep. 10, 1997.

Hereinbelow, the present invention will be described specifically with reference to the following Example. However, the present invention is not limited to this Examples.

EXAMPLE 1

1) Construction of S/FGF-1a-II Plasmid

1. Preparation of a Human Ryudocan cDNA Fragment phR7A8 is a plasmid obtained by inserting a human ryudocan cDNA (PCR product) into the EcoR V site of pBluescript II (KS+) cloning vector. This plasmid contains a partial sequence from position 7 to position 2610 in the mRNA sequence shown under Accession No. D13292 (see B.B.R.C. Vol. 190, No. 3, pp. 814-822, 1993).

This plasmid was digested with Pvu II. Using the resultant DNA fragment of 2,232 base pairs as a template, a PCR (polymerase chain reaction) was performed. As primers, #109 (5'-TTG TCG ACC CAC CAT GGC CCC CGC CCG TCT-3') (SEQ ID NO: 7) and #111 (5'-TTG ATA TCT AGA GGC ACC AAG GGA TG-3')(SEQ ID NO: 8) were used. The specifically amplified 276 bp band was separated by electrophoresis. After extraction, this fragment was double-digested with EcoR V and Sal I. The resultant 268 bp band was separated, extracted and then used in the ligation described below.

2. FGF-1a/pBluescript II (KS+)

A PCR was performed using human FGF-1 cDNA as a template and #967 (5'-GCG TCG ACA GCG CTA ATT ACA AGA AGC CCA AAC TC-3') (SEQ ID NO: 9) and #630 (5'-CCG AAT TCG AAT TCT TTA ATC AGA AGA GAC TGG-3')(SEQ ID NO: 10) as primers. The specifically amplified 434 bp band was separated by electrophoresis. After extraction, this fragment was double-digested with EcoR I and Sal I. The resultant 422 bp band was separated, extracted and then inserted into pBluescript II (KS+) cloning vector (2934 bp) double-digested with EcoR I and Sal I, where upon FGF-1a/pBluescript 1a/pBluescript II (KS+) was produced.

FGF-1a/pBluescript II (KS+) was digested with Aor51H I and Sal I in this order. The resultant 2626 bp band was separated, extracted and then used in the ligation described below.

3. Preparation of S/FGF-1a-II Chimeric Gene EcoR V/Sal I fragment (a PCR product from human ryudocan) and Aor51H I/Sal I fragment from FGF-1a/pBluescript II (KS+) were subjected to a DNA ligation to produce S/FGF-1a-II/pBluescript II (KS+) vector. Subsequently, this vector was double-digested with EcoR I and Sal I to give a 678 bp band, which was then separated and extracted. The resultant fragment was inserted into pMEXneo expression vector (5916 bp) double-digested with EcoR I and Sal I, where upon S/FGF-1a-II/pMEXneo was produced. This expression vector comprises the nucleotide sequence shown in SEQ ID NO: 2.

2) Expression of S/FGF-1a-II

The resultant S/FGF-1a-II/pMEXneo was transferred into CHO-K1 cells (Chinese hamster ovary cell K1 substrain) by lipofection. Then, the cells were cultured in the presence of Geneticin to select gene-transferred cells. The selected cells were grown until the culture plate became almost full. Then, the medium was exchanged with a serum-free medium to increase the substance productivity of the cells. Thereafter, the medium was exchanged with a fresh one every two days. The resultant conditioned medium was subjected to low speed centrifugation, and the resultant supernatant was stored at 4° C.

3) Construction of N-FGF6/1a-IV Plasmid

1. Preparation of a Mouse FGF-6 cDNA Fragment

A PCR was performed using mouse FGF-6 cDNA as a template and #1048 (5'-GCG TCG ACC CAC CAT GTC CCG GGG AGC AGG ACG TGT TCA GGG CAC GCTGCA GGC TCT CGT CTT C-3')(SEQ ID NO: 11) and #968 (5'-GCG ATA TCC AGT AGC GTG CCG TTG GCG CG-3') (SEQ ID NO: 12) as primers. The specifically amplified 138 bp band was separated by electrophoresis. After extraction, this fragment was double-digested with EcoR V and Sal I. The resultant 130 bp band was separated, extracted and then used in the ligation described below.

2. Preparation of N-FGF6/1a-IV Chimeric Gene

EcoR V/Sal I fragment (a PCR product from mouse FGF-6) and Aor51H I/Sal I fragment from FGF-1a/pBluescript II (KS+) were subjected to a DNA ligation to produce N-FGF-6/1a-IV/pBluescript II (KS+) vector. Subsequently, this vector was double-digested with EcoR I and Sal I to give a 540 bp band, which was then separated and extracted. The resultant fragment was inserted into pMEXneo expression vector (5916 bp) double-digested with EcoR I and Sal I, where upon N-FGF-6/1a-IV/pMEXneo was produced. This expression vector comprises the nucleotide sequence shown in SEQ ID NO: 4.

4) Expression of N-FGF-6/1a-IV

N-FGF-6/1a-IV was secreted into a culture supernatant by transferring N-FGF-6/1a-IV/pMEXneo into CHO-K1 cells in the same manner as described above for S/FGF6/1a-II.

5) Construction of O-FGF-6/1a Plasmid

1. Preparation of N-FGF6/1a<NQ> Chimeric Gene

A PCR was performed using N-FGF6/1a/pBluescript II (KS+) vector as a template and #105 (5'-GCG TCG ACC CAC CAT GTC-3')(SEQ ID NO: 13) and #124 (5'-GCG ATA TCC AGT AGC GTG CCT TGG GCG CG-3')(SEQ ID NO: 14) as primers. The specifically amplified 138 bp band was separated by electrophoresis. After extraction, this fragment was double-digested with EcoR V and Sal I. The resultant 130 bp band was subjected to the ligation described below together with Aor51H I/Sal I fragment from FGF-1a/pBluescript II (KS+), to thereby yield N-FGF-6/1a<NQ>/pBluescript II (KS+) vector.

2. Preparation of O-FGF-6/1a Chimeric Gene

A primary PCR was performed using N-FGF6/1a<NQ>/pBluescript II (KS+) vector as a template and #098 (5'-GCT GGA GGA GGC TGC TAC TCC AGC TTC AAA CCA TTA CA-3') (SEQ ID NO: 15) and #116 (5=-GCC GCT CTA GAA CTA GTG GAT-3') (SEQ ID NO: 16) as primers. The specifically amplified 210 bp band was purified. Using this PCR product and #115 (5'-AAC AAA AGC TGG GTA CCG GG-3') as primers, a secondary PCR was performed. The specifically amplified 631 bp band was separated by electrophoresis. After extraction and purification, this fragment was double-digested with EcoR I and Sal I. The resultant 558 bp band was separated, extracted and then inserted into pMEXneo expression vector (5916 bp) double-digested with EcoR I and Sal I, to thereby yield O-FGF-6/1a/pMEXneo. This expression vector comprises the nucleotide sequence shown in SEQ ID NO: 6.

6) Expression of O-FGF-6/1a

O-FGF-6/1a was secreted into a culture supernatant by transferring O-FGF6/1a/pMEXneo into CHO-K1 cells in the same manner as described above for S/FGF-1a-II.

7) Expression of FGF-1a in *E. coli*

The fragment from human FGF-1a cDNA obtained by double digestion with Eco RI and Sal I as described above was incorporated into an *E. coli* expression vector pET3c. *E. coli* BL21 (DE3)pLysS was transformed with the resultant vector. Subsequently, the transformant at the logarithmic growth phase was stimulated with IPTG (isopropylthio-β-galactoside) to induce the expression of the transferred gene. The cells were collected and sonicated for disruption to thereby release FGF-1a, which was then recovered in a centrifugation supernatant.

8) Removal of N-Linked Sugar Chains by Peptide N-Glycosidase F Treatment

N-FGF6/1a-II concentrated with heparin-Sepharose beads was boiled and eluted in an electrophoresis buffer, as will be described later (see Test Example 1). To a part of the resultant solution, NP-40 (final concentration: 1%), Tris-HCl buffer (pH 7.5) and peptide N-glycosidase F (0.3 U) were added and the mixture was kept at 37° C. overnight. Then, the solution was heated at 100° C. for 3 min to terminate the enzyme reaction. This reaction solution was analyzed by SDS-denatured electrophoresis, as will be described later.

Various S/FGF-1a and N-FGF-6/1a genes can be prepared by appropriately altering the PCR primers (#111 and #968) used in "1. Preparation of a Human Ryudocan cDNA Fragment" and "1. Preparation of a Mouse FGF-6 cDNA Fragment" in the above Example and by replacing the restriction enzyme EcoR V with an appropriate enzyme which would generate a blunt end. Examples of such cDNA sequences are shown in SEQ ID NOS: 8, 20, 22, 24, 26 and 28.

Various O-FGF-6/1a genes can be prepared by replacing the template used in the PCR in "2. Preparation of O-FGF-6/1a Chimeric Gene" above with S/FGF-1a-II/pBluescript II (KS+), N-FGF6/1a-IV/pBluescript II (KS+) or the like, or by appropriately altering the PCR primers (#098, #116 and #115), or by a combination of the both methods. An example of such a cDNA sequence is shown in SEQ ID NO: 30.

TEST EXAMPLE 1

SDS-Denatured Electrophoresis

Heparin Sepharose beads added to conditioned media of various FGF-1a-like proteins-secreting cells were individually washed and then boiled directly with an electrophoresis buffer (containing SDS and 2-' mercaptoethanol). The eluted protein was used as a sample. This sample was electrophoresed on 12.5% acrylamide gel in the presence of SDS and 2-mercaptoethanol. After being electrically transferred onto a nitrocellulose membrane, the protein was stained with anti-FGF-1 monoclonal antibody and horseradish peroxidase-labelled anti-mouse IgG antibody, followed by detection by the chemiluminescence method (FIG. 4). In the Figure, the arrows at the left side indicate the locations of standard proteins with known molecular weights and their molecular weights (in daltons). Panel A) shows an SDS-denatured electrophoregram of S/FGF-1a-II. Panel B) shows SDS-denatured electrophoregrams of FGF-1a produced in *E. coli* (lane a); N-FGF-1a-IV obtained by treating N-FGF-6/1a-IV with peptide N-glycosidase F for removal of N-linked sugar chains (lane b); N-FGF6/1a-IV (lane c) and O-FGF-6/1a (lane d).

TEST EXAMPLE 2

DNA Synthesis Promoting Activity

The cell cycle of HUVEC (human umbilical cord-derived vascular endothelial cell) stops even in the presence of 15% serum if growth factors such as FGF are lacking. S/FGF-1a-II, N-FGF6/1a-IV, O-FGF-6/1a, or FGF-1a produced in *E. coli* was added to HUVEC in such a state. Eighteen hours later, radio-labelled thymidine was allowed to be taken up for 6 hours. The amount of radioactivity taken up into DNA during this period was regarded as indicating the amount of the newly synthesized DNA.

1. DNA Synthesis Promoting Effect (Heparin Non-Dependent) of S/FGF-1a-II on Human Vascular Endothelial Cell A conditioned medium was prepared from a serum-free medium of S/FGF-1a-II gene-transferred cells. This conditioned medium was dialyzed against PBS and then added to HUVEC in the presence (5 µg/ml) or absence of heparin, for examining the DNA synthesis promoting activity of S/FGF-1a-II on HUVEC (FIG. 5A). As a result, unlike FGF-1a produced in *E. coli*(FIG. 5B), S/FGF-1a-II promoted the DNA synthesis of HUVEC in a non-heparin-dependent manner (FIG. 5).

2. DNA Synthesis Promoting Effect of N-FGF6/1a-IV on Human Vascular Endothelial Cell A conditioned medium was prepared from a serum-free medium of N-FGF-6/1a-IV gene-transferred cells. This conditioned medium was dialyzed against PBS and then added to HUVEC in the presence (5 µg/ml) or absence of heparin, for examining the DNA synthesis promoting activity of N-FGF6/1a-IV on HUVEC. As a result, like FGF-1a produced in *E=coli*, N-FGF6/1a-IV promoted the DNA synthesis of HUVEC. However, its heparin dependency was weak, and N-FGF6/1a-IV exhibited stronger DNA synthesis promoting activity than FGF-1a from *E=coli* in the absence of heparin (FIG. 8).

TEST EXAMPLE 3

Heparin Affinity Chromatography

The heparin affinity of S/FGF-1a-II obtained in 2) in the above Example was examined. Heparin-Sepharose beads were added to a conditioned medium of S/FGF-1a-II-secreting cells and agitated at 4° C. for 2 hours or more. Beads precipitating by low speed centrifugation were recovered and washed sufficiently in physiological PBS (phosphate buffered saline, pH 7.4), followed by elution of the protein bound to heparin-fixed beads with PBS containing 2.5 M NaCl. After addition of distilled water to lower the salt concentration, this eluate was again applied to a high performance liquid chromatography column packed with heparin affinity beads. S/FGF-1a-II was eluted using NaCl density gradient.

While FGF-1a from *E. coli* was eluted at about 1.0 M NaCl, S/FGF-1a-II was eluted at about 0.4 M NaCl. Thus, it appears that affinity to the fixed heparin is lowered in S/FGF-1a-II (FIG. 9). The small peak seen around 1.0 M NaCl in FIG. 9 is considered to be a degradation product from S/FGF-1a-II as analyzed by SDS-denatured electrophoresis.

TEST EXAMPLE 4

Thermostability of FGF-1a-Like Proteins

Conditioned media of various FGF-1a-like protein-secreting cells were individually dialyzed against PBS sufficiently. A part of each of the resultant media was retained in PBS kept at 56° C. or 70° C. for 30 minutes, or retained at room temperature for 12 hours. Thereafter, the medium was re-dialyzed against PBS at 4° C. to prepare a sample. The stability of S/FGF-1a-II was determined by subjecting it to DNA synthesis promoting activity test on HUVEC after various treatments and then comparing the resultant activity with the activity of an S/FGF-1a-II sample dialyzed against PBS at 4° C. for 12 hours (FIG. 6A).

After retention at room temperature for 12 hours, even the activity of E. coli-derived FGF-1a was protected by heparin, but the activity of S/FGF-1a-II was protected regardless of the presence or absence of heparin (FIG. 6A).

After heat treatment at 56° C. for 30 minutes, E. coli-derived FGF-1a was almost deactivated, but S/FGF-1a-II retained about 50% of the activity. Thus, it was considered that its thermostability was improved (FIG. 6B).

TEST EXAMPLE 5

Acid Resistance and Alkali Resistance of FGF-1a-Like Proteins

Conditioned media of various FGF-1a-like protein-secreting cells were individually dialyzed against PBS sufficiently. A part of each of the resultant media was dialyzed in a citrate buffer (pH 4.0) or a sodium carbonate buffer (pH 10.0) for 12 hours and then re-dialyzed against PBS at 4° C. to prepare a sample. The stability of S/FGF-1a-II was determined by subjecting it to DNA synthesis promoting activity test on HUVEC after various treatments and then comparing the resultant activity with the activity of an S/FGF-1a-II sample dialyzed against PBS at 4° C. for 12 hours.

The activity of S/FGF-1a-II decreased little even after acid treatment at pH 4.0 regardless of the presence or absence of heparin; thus, an improvement in acid resistance was recognized (FIG. 6A). After alkali treatment at pH 10.0, E. coli-derived FGF-1a was almost deactivated, but S/FGF-1a-II retained about 50% of the activity; thus, an improvement was also recognized in alkali resistance (FIGS. 6A and 6B).

TEST EXAMPLE 6

Stability of FGF-1a-Like Proteins Against Proteolytic Enzymes

Conditioned media of various FGF-1a-like protein-secreting cells were individually dialyzed against PBS sufficiently. To a part of each of the resultant media, trypsin solutions of varying concentrations (0.0001–0.1%) were added and kept at 37° C. for 1 hour. The thus obtained sample was subjected to the SDS-denatured electrophoresis described previously. The intensity of the remaining band was compared to the intensity of the band generated by the sample before trypsin treatment to give an indicator of stability.

As a result, as shown in FIG. 7, 88% and 35% of the band intensity remained in S/FGF-1a-II after 0.001% and 0.01% trypsin treatment, respectively; however, the band intensity of E. coli-derived FGF-1a decreased to 58% and even to 6% after 0.001% and 0.01% trypsin treatment, respectively. Thus, it was considered that the resistance of S/FGF-1a-II to proteolytic enzymes was increased (FIG. 7).

---

SEQUENCE LISTING

<160> NUMBER OF SEQ ID NOS: 31

<210> SEQ ID NO 1
<211> LENGTH: 221
<212> TYPE: PRT
<213> ORGANISM: Artificial Sequence
<220> FEATURE:
<223> OTHER INFORMATION: Description of Artificial Sequence: fusion of sequence for a part of human rydocan and a part of human fibroblast growth factor 1

<400> SEQUENCE: 1

Met Ala Pro Ala Arg Leu Phe Ala Leu Leu Leu Phe Phe Val Gly Gly
 1               5                  10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Asp Phe Glu Leu Ser Gly Ser Gly
    50                  55                  60

Asp Leu Asp Asp Leu Glu Asp Ser Met Ile Gly Pro Glu Val Val His
65                  70                  75                  80

Pro Leu Val Pro Leu Asp Ala Asn Tyr Lys Lys Pro Lys Leu Leu Tyr

-continued

```
                        85                  90                  95
        Cys Ser Asn Gly Gly His Phe Leu Arg Ile Leu Pro Asp Gly Thr Val
                        100                 105                 110

Asp Gly Thr Arg Asp Arg Ser Asp Gln His Ile Gln Leu Gln Leu Ser
                        115                 120                 125

Ala Glu Ser Val Gly Glu Val Tyr Ile Lys Ser Thr Glu Thr Gly Gln
                130                 135                 140

Tyr Leu Ala Met Asp Thr Asp Gly Leu Leu Tyr Gly Ser Gln Thr Pro
        145                 150                 155                 160

Asn Glu Glu Cys Leu Phe Leu Glu Arg Leu Glu Glu Asn His Tyr Asn
                        165                 170                 175

Thr Tyr Ile Ser Lys Lys His Ala Glu Lys Asn Trp Phe Val Gly Leu
                        180                 185                 190

Lys Lys Asn Gly Ser Cys Lys Arg Gly Pro Arg Thr His Tyr Gly Gln
                        195                 200                 205

Lys Ala Ile Leu Phe Leu Pro Leu Pro Val Ser Ser Asp
        210                 215                 220

<210> SEQ ID NO 2
<211> LENGTH: 663
<212> TYPE: DNA
<213> ORGANISM: Artificial Sequence
<220> FEATURE:
<223> OTHER INFORMATION: Description of Artificial Sequence: fusion of
      sequence for a part of human rydocan and a part of human
      fibroblast growth factor 1
<221> NAME/KEY: CDS
<222> LOCATION: (1)..(663)

<400> SEQUENCE: 2 atg gcc ccc gcc cgt ctg ttc gcg ctg ctg ctg ttc ttc gta ggc gga    48
Met Ala Pro Ala Arg Leu Phe Ala Leu Leu Leu Phe Phe Val Gly Gly
1               5                   10                  15 gtc gcc gag tcg atc cga gag act gag gtc atc gac ccc cag gac ctc    96
Val Ala Glu Ser Ile Arg Glu Thr Glu Val Ile Asp Pro Gln Asp Leu
                20                  25                  30 cta gaa ggc cga tac ttc tcc gga gcc cta cca gac gat gag gat gta   144
Leu Glu Gly Arg Tyr Phe Ser Gly Ala Leu Pro Asp Asp Glu Asp Val
            35                  40                  45 gtg ggg ccc ggg cag gaa tct gat gac ttt gag ctg tct ggc tct gga   192
Val Gly Pro Gly Gln Glu Ser Asp Asp Phe Glu Leu Ser Gly Ser Gly
        50                  55                  60 gat ctg gat gac ttg gaa gac tcc atg atc ggc cct gaa gtt gtc cat   240
Asp Leu Asp Asp Leu Glu Asp Ser Met Ile Gly Pro Glu Val Val His
65                  70                  75                  80 ccc ttg gtg cct cta gat gct aat tac aag aag ccc aaa ctc ctc tac   288
Pro Leu Val Pro Leu Asp Ala Asn Tyr Lys Lys Pro Lys Leu Leu Tyr
                85                  90                  95 tgt agc aac ggg ggc cac ttc ctg agg atc ctt ccg gat ggc aca gtg   336
Cys Ser Asn Gly Gly His Phe Leu Arg Ile Leu Pro Asp Gly Thr Val
                100                 105                 110 gat ggg aca agg gac agg agc gac cag cac att cag ctg cag ctc agt   384
Asp Gly Thr Arg Asp Arg Ser Asp Gln His Ile Gln Leu Gln Leu Ser
            115                 120                 125 gcg gaa agc gtg ggg gag gtg tat ata aag agt acc gag act ggc cag   432
Ala Glu Ser Val Gly Glu Val Tyr Ile Lys Ser Thr Glu Thr Gly Gln
        130                 135                 140 tac ttg gcc atg gac acc gac ggg ctt tta tac ggc tca cag aca cca   480
Tyr Leu Ala Met Asp Thr Asp Gly Leu Leu Tyr Gly Ser Gln Thr Pro
145                 150                 155                 160
```

-continued

```
aat gag gaa tgt ttg ttc ctg gaa agg ctg gag gag aac cat tac aac      528
Asn Glu Glu Cys Leu Phe Leu Glu Arg Leu Glu Glu Asn His Tyr Asn
                165                 170                 175 acc tat ata tcc aag aag cat gca gag aag aat tgg ttt gtt ggc ctc      576
Thr Tyr Ile Ser Lys Lys His Ala Glu Lys Asn Trp Phe Val Gly Leu
            180                 185                 190 aag aag aat ggg agc tgc aaa cgc ggt cct cgg act cac tat ggc cag      624
Lys Lys Asn Gly Ser Cys Lys Arg Gly Pro Arg Thr His Tyr Gly Gln
        195                 200                 205 aaa gca atc ttg ttt ctc ccc ctg cca gtc tct tct gat                  663
Lys Ala Ile Leu Phe Leu Pro Leu Pro Val Ser Ser Asp
    210                 215                 220
```

<210> SEQ ID NO 3
<211> LENGTH: 175
<212> TYPE: PRT
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth factor 1

<400> SEQUENCE: 3

```
Met Ser Arg Gly Ala Gly Arg Val Gln Gly Thr Leu Gln Ala Leu Val
 1               5                  10                  15

Phe Leu Gly Val Leu Val Gly Met Val Val Pro Ser Pro Ala Gly Ala
            20                  25                  30

Arg Ala Asn Gly Thr Leu Leu Asp Ala Asn Tyr Lys Lys Pro Lys Leu
        35                  40                  45

Leu Tyr Cys Ser Asn Gly Gly His Phe Leu Arg Ile Leu Pro Asp Gly
    50                  55                  60

Thr Val Asp Gly Thr Arg Asp Arg Ser Asp Gln His Ile Gln Leu Gln
65                  70                  75                  80

Leu Ser Ala Glu Ser Val Gly Glu Val Tyr Ile Lys Ser Thr Glu Thr
                85                  90                  95

Gly Gln Tyr Leu Ala Met Asp Thr Asp Gly Leu Leu Tyr Gly Ser Gln
            100                 105                 110

Thr Pro Asn Glu Glu Cys Leu Phe Leu Glu Arg Leu Glu Glu Asn His
        115                 120                 125

Tyr Asn Thr Tyr Ile Ser Lys Lys His Ala Glu Lys Asn Trp Phe Val
    130                 135                 140

Gly Leu Lys Lys Asn Gly Ser Cys Lys Arg Gly Pro Arg Thr His Tyr
145                 150                 155                 160

Gly Gln Lys Ala Ile Leu Phe Leu Pro Leu Pro Val Ser Ser Asp
                165                 170                 175
```

<210> SEQ ID NO 4
<211> LENGTH: 525
<212> TYPE: DNA
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth factor 1
<221> NAME/KEY: CDS
<222> LOCATION: (1)..(525)

<400> SEQUENCE: 4

```
atg tcc cgg gga gca gga cgt gtt cag ggc acg ctg cag gct ctc gtc      48
Met Ser Arg Gly Ala Gly Arg Val Gln Gly Thr Leu Gln Ala Leu Val
 1               5                  10                  15
```

-continued

```
ttc tta ggc gtc cta gtg ggc atg gtg gtg ccc tca cct gcc ggc gcc      96
Phe Leu Gly Val Leu Val Gly Met Val Val Pro Ser Pro Ala Gly Ala
             20                  25                  30 cgc gcc aac ggc acg cta ctg gac gct aat tac aag aag ccc aaa ctc     144
Arg Ala Asn Gly Thr Leu Leu Asp Ala Asn Tyr Lys Lys Pro Lys Leu
         35                  40                  45 ctc tac tgt agc aac ggg ggc cac ttc ctg agg atc ctt ccg gat ggc     192
Leu Tyr Cys Ser Asn Gly Gly His Phe Leu Arg Ile Leu Pro Asp Gly
     50                  55                  60 aca gtg gat ggg aca agg gac agg agc gac cag cac att cag ctg cag     240
Thr Val Asp Gly Thr Arg Asp Arg Ser Asp Gln His Ile Gln Leu Gln
 65                  70                  75                  80 ctc agt gcg gaa agc gtg ggg gag gtg tat ata aag agt acc gag act     288
Leu Ser Ala Glu Ser Val Gly Glu Val Tyr Ile Lys Ser Thr Glu Thr
                 85                  90                  95 ggc cag tac ttg gcc atg gac acc gac ggg ctt tta tac ggc tca cag     336
Gly Gln Tyr Leu Ala Met Asp Thr Asp Gly Leu Leu Tyr Gly Ser Gln
             100                 105                 110 aca cca aat gag gaa cgt ttg ttc ctg gaa agg ctg gag gag aac cat     384
Thr Pro Asn Glu Glu Cys Leu Phe Leu Glu Arg Leu Glu Glu Asn His
         115                 120                 125 tac aac acc tat ata tcc aag aag cat gca gag aag aat tgg ttt gtt     432
Tyr Asn Thr Tyr Ile Ser Lys Lys His Ala Glu Lys Asn Trp Phe Val
     130                 135                 140 ggc ctc aag aag aat ggg agc tgc aaa cgc ggt cct cgg act cac tat     480
Gly Leu Lys Lys Asn Gly Ser Cys Lys Arg Gly Pro Arg Thr His Tyr
145                 150                 155                 160 ggc cag aaa gca atc ttg ttt ctc ccc ctg cca gtc tct tct gat         525
Gly Gln Lys Ala Ile Leu Phe Leu Pro Leu Pro Val Ser Ser Asp
                 165                 170                 175
```

<210> SEQ ID NO 5
<211> LENGTH: 181
<212> TYPE: PRT
<213> ORGANISM: Artificial Sequence
<220> FEATURE:
<223> OTHER INFORMATION: Description of Artificial Sequence: fusion of
      sequence for a part of mouse fibroblast growth factor 6,
      a part of human fibroblast growth factor 1 and an artificial
      sequence

<400> SEQUENCE: 5

```
Met Ser Arg Gly Ala Gly Arg Val Gln Gly Thr Leu Gln Ala Leu Val
 1               5                  10                  15

Phe Leu Gly Val Leu Val Gly Met Val Val Pro Ser Pro Ala Gly Ala
             20                  25                  30

Arg Ala Gln Gly Thr Leu Leu Asp Ala Asn Tyr Lys Lys Pro Lys Leu
         35                  40                  45

Leu Tyr Cys Ser Asn Gly Gly His Phe Leu Arg Ile Leu Pro Asp Gly
     50                  55                  60

Thr Val Asp Gly Thr Arg Asp Arg Ser Asp Gln His Ile Gln Leu Gln
 65                  70                  75                  80

Leu Ser Ala Glu Ser Val Gly Glu Val Tyr Ile Lys Ser Thr Glu Thr
                 85                  90                  95

Gly Gln Tyr Leu Ala Met Asp Thr Asp Gly Leu Leu Tyr Gly Ser Gln
             100                 105                 110

Thr Pro Asn Glu Glu Cys Leu Phe Leu Glu Arg Leu Glu Glu Ala Ala
         115                 120                 125
```

```
            130                 135                 140
Glu Lys Asn Trp Phe Val Gly Leu Lys Lys Asn Gly Ser Cys Lys Arg
145                 150                 155                 160

Gly Pro Arg Thr His Tyr Gly Gln Lys Ala Ile Leu Phe Leu Pro Leu
                165                 170                 175

Pro Val Ser Ser Asp
                180

<210> SEQ ID NO 6
<211> LENGTH: 543
<212> TYPE: DNA
<213> ORGANISM: Artificial Sequence
<220> FEATURE:
<223> OTHER INFORMATION: Description of Artificial Sequence: fusion of
      sequence for a part of mouse fibroblast growth factor 6,
      a part of human fibroblast growth factor 1 and an artificial
      sequence
<221> NAME/KEY: CDS
<222> LOCATION: (1)..(543)

<400> SEQUENCE: 6 atg tcc cgg gga gca gga cgt gtt cag ggc acg ctg cag gct ctc gtc      48
Met Ser Arg Gly Ala Gly Arg Val Gln Gly Thr Leu Gln Ala Leu Val
 1               5                  10                  15 ttc tta ggc gtc cta gtg ggc atg gtg gtg ccc tca cct gcc ggc gcc      96
Phe Leu Gly Val Leu Val Gly Met Val Val Pro Ser Pro Ala Gly Ala
                20                  25                  30 cgc gcc caa ggc acg cta ctg gac gct aat tac aag aag ccc aaa ctc     144
Arg Ala Gln Gly Thr Leu Leu Asp Ala Asn Tyr Lys Lys Pro Lys Leu
            35                  40                  45 ctc tac tgt agc aac ggg ggc cac ttc ctg agg atc ctt ccg gat ggc     192
Leu Tyr Cys Ser Asn Gly Gly His Phe Leu Arg Ile Leu Pro Asp Gly
        50                  55                  60 aca gtg gat ggg aca agg gac agg agc gac cag cac att cag ctg cag     240
Thr Val Asp Gly Thr Arg Asp Arg Ser Asp Gln His Ile Gln Leu Gln
 65                  70                  75                  80 ctc agt gcg gaa agc gtg ggg gag gtg tat ata aag agt acc gag act     288
Leu Ser Ala Glu Ser Val Gly Glu Val Tyr Ile Lys Ser Thr Glu Thr
                85                  90                  95 ggc cag tac ttg gcc atg gac acc gac ggg ctt tta tac ggc tca cag     336
Gly Gln Tyr Leu Ala Met Asp Thr Asp Gly Leu Leu Tyr Gly Ser Gln
            100                 105                 110 aca cca aat gag gaa tgt ttg ttc ctg gaa agg ctg gag gag gct gct     384
Thr Pro Asn Glu Glu Cys Leu Phe Leu Glu Arg Leu Glu Glu Ala Ala
        115                 120                 125 act cca gct cca aac cat tac aac acc tat ata tcc aag aag cat gca     432
Thr Pro Ala Pro Asn His Tyr Asn Thr Tyr Ile Ser Lys Lys His Ala
130                 135                 140 gag aag aat tgg ttt gtt ggc ctc aag aag aat ggg agc tgc aaa cgc     480
Glu Lys Asn Trp Phe Val Gly Leu Lys Lys Asn Gly Ser Cys Lys Arg
145                 150                 155                 160 ggt cct cgg act cac tat ggc cag aaa gca atc ttg ttt ctc ccc ctg     528
Gly Pro Arg Thr His Tyr Gly Gln Lys Ala Ile Leu Phe Leu Pro Leu
                165                 170                 175 cca gtc tct tct gat                                                 543
Pro Val Ser Ser Asp
                180

<210> SEQ ID NO 7
<211> LENGTH: 30
<212> TYPE: DNA
<213> ORGANISM: Artificial Sequence
```

-continued

```
<220> FEATURE:
<223> OTHER INFORMATION: Description of Artificial Sequence:primer for
      PCR

<400> SEQUENCE: 7 ttgcgaccc accatggccc ccgcccgtct                                    30

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:primer for
      PCR

<400> SEQUENCE: 8
ttgatatcta gaggcaccaa gggatg                                       26

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence:primer for
      PCR

<400> SEQUENCE: 9
gcgtcgacag cgctaattac aagaagccca aactc                             35

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:primer for
      PCR

<400> SEQUENCE: 10
ccgaattcga attctttaat cagaagagac tgg                               33

<210> SEQ ID NO 11
<211> LENGTH: 64
<212> TYPE: DNA
<213> ORGANISM: Artificial Sequence
<220> FEATURE:
<223> OTHER INFORMATION: Description of Artificial Sequence:primer for
      PCR

<400> SEQUENCE: 11
gcgtcgaccc accatgtccc ggggagcagg acgtgttcag ggcacgctgc aggctctcgt  60
cttc                                                               64

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:primer for
      PCR

<400> SEQUENCE: 12
gcgatatcca gtagcgtgcc gttggcgcg                                    29

<210> SEQ ID NO 13
<211> LENGTH: 18
<212> TYPE: DNA
```

```
<213> ORGANISM: Artificial Sequence
<220> FEATURE:
<223> OTHER INFORMATION: Description of Artificial Sequence:primer for
      PCR

<400> SEQUENCE: 13
gcgtcgaccc accatgtc                                                   18

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:primer for
      PCR

<400> SEQUENCE: 14
gcgatatcca gtagcgtgcc ttgggcgcg                                       29

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence:primer for
      PCR

<400> SEQUENCE: 15
gctggaggag gctgctactc cagctccaaa ccattaca                             38

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:primer for
      PCR

<400> SEQUENCE: 16
gccgctctag aactagtgga t                                               21

<210> SEQ ID NO 17
<211> LENGTH: 200
<212> TYPE: PRT
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1

<400> SEQUENCE: 17

Met Ala Pro Ala Arg Leu Phe Ala Leu Leu Leu Phe Phe Val Gly Gly
 1               5                  10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Asp Phe Glu Leu Ser Gly Ser Gly
    50                  55                  60

Asp Ala Asn Tyr Lys Lys Pro Lys Leu Leu Tyr Cys Ser Asn Gly Gly
65                  70                  75                  80

His Phe Leu Arg Ile Leu Pro Asp Gly Thr Val Asp Gly Thr Arg Asp
                85                  90                  95

Arg Ser Asp Gln His Ile Gln Leu Gln Leu Ser Ala Glu Ser Val Gly
```

|  | 100 |  |  |  | 105 |  |  |  | 110 |  |  |  |
|---|---|---|---|---|---|---|---|---|---|---|---|---|

Glu Val Tyr Ile Lys Ser Thr Glu Thr Gly Gln Tyr Leu Ala Met Asp
        115                 120                 125

Thr Asp Gly Leu Leu Tyr Gly Ser Gln Thr Pro Asn Glu Glu Cys Leu
        130                 135                 140

Phe Leu Glu Arg Leu Glu Glu Asn His Tyr Asn Thr Tyr Ile Ser Lys
145                 150                 155                 160

Lys His Ala Glu Lys Asn Trp Phe Val Gly Leu Lys Lys Asn Gly Ser
                165                 170                 175

Cys Lys Arg Gly Pro Arg Thr His Tyr Gly Gln Lys Ala Ile Leu Phe
                180                 185                 190

Leu Pro Leu Pro Val Ser Ser Asp
        195                 200

<210> SEQ ID NO 19
<211> LENGTH: 600
<212> TYPE: DNA
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1
<221> NAME/KEY: CDS
<222> LOCATION: (1)..(600)

<400> SEQUENCE: 19

```
atg gcc ccc gcc cgt ctg ttc gcg ctg ctg ttc ttc gta ggc gga        48
Met Ala Pro Ala Arg Leu Phe Ala Leu Leu Leu Phe Phe Val Gly Gly
  1               5                  10                  15 gtc gcc gag tcg atc cga gag act gag gtc atc gac ccc cag gac ctc    96
Val Ala Glu Ser Ile Arg Glu Thr Glu Val Ile Asp Pro Gln Asp Leu
             20                  25                  30 cta gaa ggc cga tac ttc tcc gga gcc cta cca gac gat gag gat gta   144
Leu Glu Gly Arg Tyr Phe Ser Gly Ala Leu Pro Asp Asp Glu Asp Val
         35                  40                  45 gtg ggg ccc ggg cag gaa tct gat gac ttt gag ctg tct ggc tct gga   192
Val Gly Pro Gly Gln Glu Ser Asp Asp Phe Glu Leu Ser Gly Ser Gly
     50                  55                  60 gat gct aat tac aag aag ccc aaa ctc ctc tac tgt agc aac ggg ggc   240
Asp Ala Asn Tyr Lys Lys Pro Lys Leu Leu Tyr Cys Ser Asn Gly Gly
 65                  70                  75                  80 cac ttc ctg agg atc ctt ccg gat ggc aca gtg gat ggg aca agg gac   288
His Phe Leu Arg Ile Leu Pro Asp Gly Thr Val Asp Gly Thr Arg Asp
                 85                  90                  95 agg agc gac cag cac att cag ctg cag ctc agt gcg gaa agc gtg ggg   336
Arg Ser Asp Gln His Ile Gln Leu Gln Leu Ser Ala Glu Ser Val Gly
            100                 105                 110 gag gtg tat ata aag agt acc gag act ggc cag tac ttg gcc atg gac   384
Glu Val Tyr Ile Lys Ser Thr Glu Thr Gly Gln Tyr Leu Ala Met Asp
        115                 120                 125 acc gac ggg ctt tta tac ggc tca cag aca cca aat gag gaa tgt ttg   432
Thr Asp Gly Leu Leu Tyr Gly Ser Gln Thr Pro Asn Glu Glu Cys Leu
        130                 135                 140 ttc ctg gaa agg ctg gag gag aac cat tac aac acc tat ata tcc aag   480
Phe Leu Glu Arg Leu Glu Glu Asn His Tyr Asn Thr Tyr Ile Ser Lys
145                 150                 155                 160 aag cat gca gag aag aat tgg ttt gtt ggc ctc aag aag aat ggg agc   528
Lys His Ala Glu Lys Asn Trp Phe Val Gly Leu Lys Lys Asn Gly Ser
                165                 170                 175 tgc aaa cgc ggt cct cgg act cac tat ggc cag aaa gca atc ttg ttt   576
```

```
Cys Lys Arg Gly Pro Arg Thr His Tyr Gly Gln Lys Ala Ile Leu Phe
            180                 185                 190 ctc ccc ctg cca gtc tct tct gat                                         600
Leu Pro Leu Pro Val Ser Ser Asp
        195                 200
```

<210> SEQ ID NO 19
<211> LENGTH: 200
<212> TYPE: PRT
<213> ORGANISM: Artificial Sequence
<220> FEATURE:
<223> OTHER INFORMATION: Description of Artificial Sequence: fusion of
      sequence for a part of human ryudocan mutant and a part of human
      fibroblast growth factor 1

<400> SEQUENCE: 19

```
Met Ala Pro Ala Arg Leu Phe Ala Leu Leu Leu Phe Phe Val Gly Gly
  1               5                  10                  15

Val Ala Glu Ser Ile Arg Glu Thr Glu Val Ile Asp Pro Gln Asp Leu
             20                  25                  30

Leu Glu Gly Arg Tyr Phe Ser Gly Ala Leu Ser Asp Asp Glu Asp Val
         35                  40                  45

Val Gly Pro Gly Gln Glu Ser Asp Asp Phe Glu Leu Ser Gly Ser Gly
     50                  55                  60

Asp Ala Asn Tyr Lys Lys Pro Lys Leu Leu Tyr Cys Ser Asn Gly Gly
 65                  70                  75                  80

His Phe Leu Arg Ile Leu Pro Asp Gly Thr Val Asp Gly Thr Arg Asp
                 85                  90                  95

Arg Ser Asp Gln His Ile Gln Leu Gln Leu Ser Ala Glu Ser Val Gly
            100                 105                 110

Glu Val Tyr Ile Lys Ser Thr Glu Thr Gly Gln Tyr Leu Ala Met Asp
        115                 120                 125

Thr Asp Gly Leu Leu Tyr Gly Ser Gln Thr Pro Asn Glu Glu Cys Leu
    130                 135                 140

Phe Leu Glu Arg Leu Glu Glu Asn His Tyr Asn Thr Tyr Ile Ser Lys
145                 150                 155                 160

Lys His Ala Glu Lys Asn Trp Phe Val Gly Leu Lys Lys Asn Gly Ser
                165                 170                 175

Cys Lys Arg Gly Pro Arg Thr His Tyr Gly Gln Lys Ala Ile Leu Phe
            180                 185                 190

Leu Pro Leu Pro Val Ser Ser Asp
        195                 200
```

<210> SEQ ID NO 20
<211> LENGTH: 600
<212> TYPE: DNA
<213> ORGANISM: Artificial Sequence
<220> FEATURE:
<223> OTHER INFORMATION: Description of Artificial Sequence: fusion of
      sequence for a part of human ryudocan mutant and a part of human
      fibroblast growth factor 1
<221> NAME/KEY: CDS
<222> LOCATION: (1)..(600)

<400> SEQUENCE: 20

```
atg gcc ccc gcc cgt ctg ttc gcg ctg ctg ctg ttc ttc gta ggc gga    48
Met Ala Pro Ala Arg Leu Phe Ala Leu Leu Leu Phe Phe Val Gly Gly
  1               5                  10                  15 gtc gcc gag tcg atc cga gag act gag gtc atc gac ccc cag gac ctc    96
Val Ala Glu Ser Ile Arg Glu Thr Glu Val Ile Asp Pro Gln Asp Leu
             20                  25                  30
```

```
                                                                    -continued cta gaa ggc cga tac ttc tcc gga gcc cta tca gac gat gag gat gta        144
Leu Glu Gly Arg Tyr Phe Ser Gly Ala Leu Ser Asp Asp Glu Asp Val
             35                  40                  45 gtg ggg ccc ggg cag gaa tct gat gac ttt gag ctg tct ggc tct gga        192
Val Gly Pro Gly Gln Glu Ser Asp Asp Phe Glu Leu Ser Gly Ser Gly
     50                  55                  60 gat gct aat tac aag aag ccc aaa ctc ctc tac tgt agc aac ggg ggc        240
Asp Ala Asn Tyr Lys Lys Pro Lys Leu Leu Tyr Cys Ser Asn Gly Gly
 65                  70                  75                  80 cac ttc ctg agg atc ctt ccg gat ggc aca gtg gat ggg aca agg gac        288
His Phe Leu Arg Ile Leu Pro Asp Gly Thr Val Asp Gly Thr Arg Asp
                 85                  90                  95 agg agc gac cag cac att cag ctg cag ctc agt gcg gaa agc gtg ggg        336
Arg Ser Asp Gln His Ile Gln Leu Gln Leu Ser Ala Glu Ser Val Gly
            100                 105                 110 gag gtg tat ata aag agt acc gag act ggc cag tac ttg gcc atg gac        384
Glu Val Tyr Ile Lys Ser Thr Glu Thr Gly Gln Tyr Leu Ala Met Asp
            115                 120                 125 acc gac ggg ctt tta tac ggc tca cag aca cca aat gag gaa tgt ttg        432
Thr Asp Gly Leu Leu Tyr Gly Ser Gln Thr Pro Asn Glu Glu Cys Leu
130                 135                 140 ttc ctg gaa agg ctg gag gag aac cat tac aac acc tat ata tcc aag        480
Phe Leu Glu Arg Leu Glu Glu Asn His Tyr Asn Thr Tyr Ile Ser Lys
145                 150                 155                 160 aag cat gca gag aag aat tgg ttt gtt ggc ctc aag aag aat ggg agc        528
Lys His Ala Glu Lys Asn Trp Phe Val Gly Leu Lys Lys Asn Gly Ser
                165                 170                 175 tgc aaa cgc ggt cct cgg act cac tat ggc cag aaa gca atc ttg ttt        576
Cys Lys Arg Gly Pro Arg Thr His Tyr Gly Gln Lys Ala Ile Leu Phe
            180                 185                 190 ctc ccc ctg cca gtc tct tct gat                                        600
Leu Pro Leu Pro Val Ser Ser Asp
            195                 200

<210> SEQ ID NO 21
<211> LENGTH: 254
<212> TYPE: PRT
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1

<400> SEQUENCE: 21

Met Ala Pro Ala Arg Leu Phe Ala Leu Leu Leu Phe Phe Val Gly Gly
  1               5                  10                  15

Val Ala Glu Ser Ile Arg Glu Thr Glu Val Ile Asp Pro Gln Asp Leu
             20                  25                  30

Leu Glu Gly Arg Tyr Phe Ser Gly Ala Leu Pro Asp Asp Glu Asp Val
         35                  40                  45

Val Gly Pro Gly Gln Glu Ser Asp Asp Phe Glu Leu Ser Gly Ser Gly
     50                  55                  60

Asp Leu Asp Asp Leu Glu Asp Ser Met Ile Gly Pro Glu Val Val His
 65                  70                  75                  80

Pro Leu Val Pro Leu Asp Asn His Ile Pro Glu Arg Ala Gly Ser Gly
                 85                  90                  95

Ser Gln Val Pro Thr Glu Pro Lys Lys Leu Glu Glu Asn Glu Val Ile
            100                 105                 110

Pro Lys Arg Ile Ser Pro Val Ala Asn Tyr Lys Lys Pro Lys Leu Leu
```

```
                    115                 120                 125

Tyr Cys Ser Asn Gly Gly His Phe Leu Arg Ile Leu Pro Asp Gly Thr
            130                 135                 140

Val Asp Gly Thr Arg Asp Arg Ser Asp Gln His Ile Gln Leu Gln Leu
    145                 150                 155                 160

Ser Ala Glu Ser Val Gly Glu Val Tyr Ile Lys Ser Thr Glu Thr Gly
                    165                 170                 175

Gln Tyr Leu Ala Met Asp Thr Asp Gly Leu Leu Tyr Gly Ser Gln Thr
                180                 185                 190

Pro Asn Glu Glu Cys Leu Phe Leu Glu Arg Leu Glu Glu Asn His Tyr
                195                 200                 205

Asn Thr Tyr Ile Ser Lys Lys His Ala Glu Lys Asn Trp Phe Val Gly
            210                 215                 220

Leu Lys Lys Asn Gly Ser Cys Lys Arg Gly Pro Arg Thr His Tyr Gly
    225                 230                 235                 240

Gln Lys Ala Ile Leu Phe Leu Pro Leu Pro Val Ser Ser Asp
                    245                 250

<210> SEQ ID NO 22
<211> LENGTH: 762
<212> TYPE: DNA
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1
<221> NAME/KEY: CDS
<222> LOCATION: (1)..(762)

<400> SEQUENCE: 22 atg gcc ccc gcc cgt ctg ttc gcg ctg ctg ctg ttc ttc gta ggc gga        48
Met Ala Pro Ala Arg Leu Phe Ala Leu Leu Leu Phe Phe Val Gly Gly
1               5                   10                  15 gtc gcc gag tcg atc cga gag act gag gtc atc gac ccc cag gac ctc        96
Val Ala Glu Ser Ile Arg Glu Thr Glu Val Ile Asp Pro Gln Asp Leu
                20                  25                  30 cta gaa ggc cga tac ttc tcc gga gcc cta cca gac gat gag gat gta       144
Leu Glu Gly Arg Tyr Phe Ser Gly Ala Leu Pro Asp Asp Glu Asp Val
            35                  40                  45 gtg ggg ccc ggg cag gaa tct gat gac ttt gag ctg tct ggc tct gga       192
Val Gly Pro Gly Gln Glu Ser Asp Asp Phe Glu Leu Ser Gly Ser Gly
        50                  55                  60 gat ctg gat gac ctg gaa gac tcc atg atc ggc cct gaa gtt gtc cat       240
Asp Leu Asp Asp Leu Glu Asp Ser Met Ile Gly Pro Glu Val Val His
65                  70                  75                  80 ccc ttg gtg cct cta gat aac cat atc cct gag agg gca ggg tct ggg       288
Pro Leu Val Pro Leu Asp Asn His Ile Pro Glu Arg Ala Gly Ser Gly
                85                  90                  95 agc caa gtc ccc acc gaa ccc aag aaa cta gag gag aat gag gtt atc       336
Ser Gln Val Pro Thr Glu Pro Lys Lys Leu Glu Glu Asn Glu Val Ile
                100                 105                 110 ccc aag aga atc tca ccc gtt gct aat tac aag aag ccc aaa ctc ctc       384
Pro Lys Arg Ile Ser Pro Val Ala Asn Tyr Lys Lys Pro Lys Leu Leu
            115                 120                 125 tac tgt agc aac ggg ggc cac ttc ctg agg atc ctt ccg gat ggc aca       432
Tyr Cys Ser Asn Gly Gly His Phe Leu Arg Ile Leu Pro Asp Gly Thr
        130                 135                 140 gtg gat ggg aca agg gac agg agc gac cag cac att cag ctg cag ctc       480
Val Asp Gly Thr Arg Asp Arg Ser Asp Gln His Ile Gln Leu Gln Leu
145                 150                 155                 160
```

```
agt gcg gaa agc gtg ggg gag gtg tat ata aag agt acc gag act ggc       528
Ser Ala Glu Ser Val Gly Glu Val Tyr Ile Lys Ser Thr Glu Thr Gly
                165                 170                 175 cag tac ttg gcc atg gac acc gac ggg ctt tta tac ggc tca cag aca       576
Gln Tyr Leu Ala Met Asp Thr Asp Gly Leu Leu Tyr Gly Ser Gln Thr
            180                 185                 190 cca aat gag gaa tgt ttg ttc ctg gaa agg ctg gag gag aac cat tac       624
Pro Asn Glu Glu Cys Leu Phe Leu Glu Arg Leu Glu Glu Asn His Tyr
        195                 200                 205 aac acc tat ata tcc aag aag cat gca gag aag aat tgg ttt gtt ggc       672
Asn Thr Tyr Ile Ser Lys Lys His Ala Glu Lys Asn Trp Phe Val Gly
    210                 215                 220 ctc aag aag aat ggg agc tgc aaa cgc ggt cct cgg act cac tat ggc       720
Leu Lys Lys Asn Gly Ser Cys Lys Arg Gly Pro Arg Thr His Tyr Gly
225                 230                 235                 240 cag aaa gca atc ttg ttt ctc ccc ctg cca gtc tct tct gat               762
Gln Lys Ala Ile Leu Phe Leu Pro Leu Pro Val Ser Ser Asp
                245                 250

<210> SEQ ID NO 23
<211> LENGTH: 281
<212> TYPE: PRT
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1

<400> SEQUENCE: 23

Met Ala Pro Ala Arg Leu Phe Ala Leu Leu Leu Phe Phe Val Gly Gly
 1               5                  10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Asp Phe Glu Leu Ser Gly Ser Gly
    50                  55                  60

Asp Leu Asp Asp Leu Glu Asp Ser Met Ile Gly Pro Glu Val Val His
65                  70                  75                  80

Pro Leu Val Pro Leu Asp Asn His Ile Pro Glu Arg Ala Gly Ser Gly
                85                  90                  95

Ser Gln Val Pro Thr Glu Pro Lys Lys Leu Glu Asn Glu Val Ile
            100                 105                 110

Pro Lys Arg Ile Ser Pro Val Glu Glu Ser Glu Asp Val Ser Asn Lys
        115                 120                 125

Val Ser Met Ser Ser Thr Val Gln Gly Ser Asn Ile Phe Glu Arg Thr
    130                 135                 140

Glu Val Ala Asn Tyr Lys Lys Pro Lys Leu Leu Tyr Cys Ser Asn Gly
145                 150                 155                 160

Gly His Phe Leu Arg Ile Leu Pro Asp Gly Thr Val Asp Gly Thr Arg
                165                 170                 175

Asp Arg Ser Asp Gln His Ile Gln Leu Gln Leu Ser Ala Glu Ser Val
            180                 185                 190

Gly Glu Val Tyr Ile Lys Ser Thr Glu Thr Gly Gln Tyr Leu Ala Met
        195                 200                 205

Asp Thr Asp Gly Leu Leu Tyr Gly Ser Gln Thr Pro Asn Glu Glu Cys
    210                 215                 220
```

```
Leu Phe Leu Glu Arg Leu Glu Glu Asn His Tyr Asn Thr Tyr Ile Ser
225                 230                 235                 240

Lys Lys His Ala Glu Lys Asn Trp Phe Val Gly Leu Lys Lys Asn Gly
            245                 250                 255

Ser Cys Lys Arg Gly Pro Arg Thr His Tyr Gly Gln Lys Ala Ile Leu
        260                 265                 270

Phe Leu Pro Leu Pro Val Ser Ser Asp
        275                 280

<210> SEQ ID NO 24
<211> LENGTH: 843
<212> TYPE: DNA
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1
<221> NAME/KEY: CDS
<222> LOCATION: (1)..(843)

<400> SEQUENCE: 24 atg gcc ccc gcc cgt ctg ttc gcg ctg ctg ctg ttc ttc gta ggc gga      48
Met Ala Pro Ala Arg Leu Phe Ala Leu Leu Leu Phe Phe Val Gly Gly
1               5                   10                  15 gtc gcc gag tcg atc cga gag act gag gtc atc gac ccc cag gac ctc      96
Val Ala Glu Ser Ile Arg Glu Thr Glu Val Ile Asp Pro Gln Asp Leu
                20                  25                  30 cta gaa ggc cga tac ttc tcc gga gcc cta cca gac gat gag gat gta     144
Leu Glu Gly Arg Tyr Phe Ser Gly Ala Leu Pro Asp Asp Glu Asp Val
            35                  40                  45 gtg ggg ccc ggg cag gaa tct gat gac ttt gag ctg tct ggc tct gga     192
Val Gly Pro Gly Gln Glu Ser Asp Asp Phe Glu Leu Ser Gly Ser Gly
        50                  55                  60 gat ctg gat gac ttg gaa gac tcc atg atc ggc cct gaa gtt gtc cat     240
Asp Leu Asp Asp Leu Glu Asp Ser Met Ile Gly Pro Glu Val Val His
65                  70                  75                  80 ccc ttg gtg cct cta gat aac cat atc cct gag agg gca ggg tct ggg     288
Pro Leu Val Pro Leu Asp Asn His Ile Pro Glu Arg Ala Gly Ser Gly
                85                  90                  95 agc caa gtc ccc acc gaa ccc aag aaa cta gag gag aat gag gtt atc     336
Ser Gln Val Pro Thr Glu Pro Lys Lys Leu Glu Glu Asn Glu Val Ile
            100                 105                 110 ccc aag aga atc tca ccc gtt gaa gag agt gag gat gtg tcc aac aag     384
Pro Lys Arg Ile Ser Pro Val Glu Glu Ser Glu Asp Val Ser Asn Lys
        115                 120                 125 gtg tca atg tcc agc act gtg cag ggc agc aac atc ttt gag aga acg     432
Val Ser Met Ser Ser Thr Val Gln Gly Ser Asn Ile Phe Glu Arg Thr
130                 135                 140 gag gtc gct aat tac aag aag ccc aaa ctc ctc tac tgt agc aac ggg     480
Glu Val Ala Asn Tyr Lys Lys Pro Lys Leu Leu Tyr Cys Ser Asn Gly
145                 150                 155                 160 ggc cac ttc ctg agg atc ctt ccg gat ggc aca gtg gat ggg aca agg     528
Gly His Phe Leu Arg Ile Leu Pro Asp Gly Thr Val Asp Gly Thr Arg
                165                 170                 175 gac agg agc gac cag cac att cag ctg cag ctc agt gcg gaa agc gtg     576
Asp Arg Ser Asp Gln His Ile Gln Leu Gln Leu Ser Ala Glu Ser Val
            180                 185                 190 ggg gag gtg tat ata aag agt acc gag act ggc cag tac ttg gcc atg     624
Gly Glu Val Tyr Ile Lys Ser Thr Glu Thr Gly Gln Tyr Leu Ala Met
        195                 200                 205 gac acc gac ggg ctt tta tac ggc tca cag aca cca aat gag gaa tgt     672
```

```
Asp Thr Asp Gly Leu Leu Tyr Gly Ser Gln Thr Pro Asn Glu Glu Cys
    210                 215                 220 ctg ttc ctg gaa agg ctg gag gag aac cat tac aac acc tat ata tcc     720
Leu Phe Leu Glu Arg Leu Glu Glu Asn His Tyr Asn Thr Tyr Ile Ser
225                 230                 235                 240 aag aag cat gca gag aag aat tgg ttt gtt ggc ctc aag aag aat ggg     768
Lys Lys His Ala Glu Lys Asn Trp Phe Val Gly Leu Lys Lys Asn Gly
                245                 250                 255 agc tgc aaa cgc ggt cct cgg act cac tat ggc cag aaa gca atc ttg     816
Ser Cys Lys Arg Gly Pro Arg Thr His Tyr Gly Gln Lys Ala Ile Leu
            260                 265                 270 ttt ctc ccc ctg cca gtc tct tct gat                                 843
Phe Leu Pro Leu Pro Val Ser Ser Asp
275                 280
```

<210> SEQ ID NO 25
<211> LENGTH: 172
<212> TYPE: PRT
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth factor 1

<400> SEQUENCE: 25

```
Met Ser Arg Gly Ala Gly Arg Val Gln Gly Thr Leu Gln Ala Leu Val
1               5                   10                  15

Phe Leu Gly Val Leu Val Gly Met Val Val Pro Ser Pro Ala Gly Ala
                20                  25                  30

Arg Ala Asn Gly Ser Ala Asn Tyr Lys Lys Pro Lys Leu Leu Tyr Cys
            35                  40                  45

Ser Asn Gly Gly His Phe Leu Arg Ile Leu Pro Asp Gly Thr Val Asp
        50                  55                  60

Gly Thr Arg Asp Arg Ser Asp Gln His Ile Gln Leu Gln Leu Ser Ala
65                  70                  75                  80

Glu Ser Val Gly Glu Val Tyr Ile Lys Ser Thr Glu Thr Gly Gln Tyr
                85                  90                  95

Leu Ala Met Asp Thr Asp Gly Leu Leu Tyr Gly Ser Gln Thr Pro Asn
                100                 105                 110

Glu Glu Cys Leu Phe Leu Glu Arg Leu Glu Glu Asn His Tyr Asn Thr
            115                 120                 125

Tyr Ile Ser Lys Lys His Ala Glu Lys Asn Trp Phe Val Gly Leu Lys
        130                 135                 140

Lys Asn Gly Ser Cys Lys Arg Gly Pro Arg Thr His Tyr Gly Gln Lys
145                 150                 155                 160

Ala Ile Leu Phe Leu Pro Leu Pro Val Ser Ser Asp
                165                 170
```

<210> SEQ ID NO 26
<211> LENGTH: 516
<212> TYPE: DNA
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth factor 1
<221> NAME/KEY: CDS
<222> LOCATION: (1)..(516)

<400> SEQUENCE: 26

```
atg tcc cgg gga gca gga cgt gtt cag ggc acg ctg cag gct ctc gtc     48
```

|  |  |
|---|---|
| Met Ser Arg Gly Ala Gly Arg Val Gln Gly Thr Leu Gln Ala Leu Val<br>1                5                        10                 15 | |
| ttc tta ggc gtc cta gtg ggc atg gtg gtg ccc tca cct gcc ggc gcc<br>Phe Leu Gly Val Leu Val Gly Met Val Val Pro Ser Pro Ala Gly Ala<br>                20                   25                 30 | 96 |
| cgc gcc aac ggc tcg gct aat tac aag aag ccc aaa ctc ctc tac tgt<br>Arg Ala Asn Gly Ser Ala Asn Tyr Lys Lys Pro Lys Leu Leu Tyr Cys<br>                35                   40                 45 | 144 |
| agc aac ggg ggc cac ttc ctg agg atc ctt ccg gat ggc aca gtg gat<br>Ser Asn Gly Gly His Phe Leu Arg Ile Leu Pro Asp Gly Thr Val Asp<br>    50                   55                 60 | 192 |
| ggg aca agg gac agg agc gac cag cac att cag ctg cag ctc agt gcg<br>Gly Thr Arg Asp Arg Ser Asp Gln His Ile Gln Leu Gln Leu Ser Ala<br>65                   70                   75                 80 | 240 |
| gaa agc gtg ggg gag gtg tat ata aag agt acc gag act ggc cag tac<br>Glu Ser Val Gly Glu Val Tyr Ile Lys Ser Thr Glu Thr Gly Gln Tyr<br>                        85                   90                 95 | 288 |
| ttg gcc atg gac acc gac ggg ctt tta tac ggc tca cag aca cca aat<br>Leu Ala Met Asp Thr Asp Gly Leu Leu Tyr Gly Ser Gln Thr Pro Asn<br>                100                 105              110 | 336 |
| gag gaa tgt ttg ttc ctg gaa agg ctg gag gag aac cat tac aac acc<br>Glu Glu Cys Leu Phe Leu Glu Arg Leu Glu Glu Asn His Tyr Asn Thr<br>            115                 120              125 | 384 |
| tat ata tcc aag aag cat gca gag aag aat tgg ttt gtt ggc ctc aag<br>Tyr Ile Ser Lys Lys His Ala Glu Lys Asn Trp Phe Val Gly Leu Lys<br>    130                 135              140 | 432 |
| aag aat ggg agc tgc aaa cgc ggt cct cgg act cac tat ggc cag aaa<br>Lys Asn Gly Ser Cys Lys Arg Gly Pro Arg Thr His Tyr Gly Gln Lys<br>145                   150                 155              160 | 480 |
| gca atc ttg ttt ctc ccc ctg cca gtc tct tct gat<br>Ala Ile Leu Phe Leu Pro Leu Pro Val Ser Ser Asp<br>                 165                 170 | 516 |

<210> SEQ ID NO 27
<211> LENGTH: 210
<212> TYPE: PRT
<213> ORGANISM: Artificial Sequence
<220> FEATURE:
<223> OTHER INFORMATION: Description of Artificial Sequence: fusion of
     sequence for a part of mouse fibroblast growth factor 6 and
     a part of human fibroblast growth 1

<400> SEQUENCE: 27

Met Ser Arg Gly Ala Gly Arg Val Gln Gly Thr Leu Gln Ala Leu Val
1                5                        10                 15

Phe Leu Gly Val Leu Val Gly Met Val Val Pro Ser Pro Ala Gly Ala
              20                   25                 30

Arg Ala Asn Gly Thr Leu Leu Asp Ser Arg Gly Trp Gly Thr Leu Leu
              35                   40                 45

Ser Arg Ser Arg Ala Gly Leu Ala Gly Glu Ile Ser Gly Val Asn Trp
    50                   55                 60

Glu Ser Gly Tyr Leu Val Gly Ile Lys Arg Gln Ala Asn Tyr Lys Lys
65                   70                   75                 80

Pro Lys Leu Leu Tyr Cys Ser Asn Gly Gly His Phe Leu Arg Ile Leu
                85                   90                 95

Pro Asp Gly Thr Val Asp Gly Thr Arg Asp Arg Ser Asp Gln His Ile
            100                 105              110

Gln Leu Gln Leu Ser Ala Glu Ser Val Gly Glu Val Tyr Ile Lys Ser
          115                 120              125

-continued

```
Thr Glu Thr Gly Gln Tyr Leu Ala Met Asp Thr Asp Gly Leu Leu Tyr
    130                 135                 140

Gly Ser Gln Thr Pro Asn Glu Glu Cys Leu Phe Leu Glu Arg Leu Glu
145                 150                 155                 160

Glu Asn His Tyr Asn Thr Tyr Ile Ser Lys Lys His Ala Glu Lys Asn
                165                 170                 175

Trp Phe Val Gly Leu Lys Lys Asn Gly Ser Cys Lys Arg Gly Pro Arg
            180                 185                 190

Thr His Tyr Gly Gln Lys Ala Ile Leu Phe Leu Pro Leu Pro Val Ser
        195                 200                 205

Ser Asp
    210

<210> SEQ ID NO 28
<211> LENGTH: 630
<212> TYPE: DNA
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth 1
<221> NAME/KEY: CDS
<222> LOCATION: (1)...(630)

<400> SEQUENCE: 28
```

| | | | | | | | | | | | | | | | | |
|---|---|---|---|---|---|---|---|---|---|---|---|---|---|---|---|---|
| atg tcc cgg gga gca gga cgt gtt cag ggc acg ctg cag gct ctc gtc | | | | | | | | | | | | | | | | 48 |
| Met Ser Arg Gly Ala Gly Arg Val Gln Gly Thr Leu Gln Ala Leu Val | | | | | | | | | | | | | | | | |
| 1   5                  10                  15 | | | | | | | | | | | | | | | | |

```
ttc tta ggc gtc cta gtg ggc atg gtg gtg ccc tca cct gcc ggc gcc      96
Phe Leu Gly Val Leu Val Gly Met Val Val Pro Ser Pro Ala Gly Ala
            20                  25                  30 cgc gcc aac ggc acg cta ctg gac tcc aga ggc tgg ggc acc ctc ttg      144
Arg Ala Asn Gly Thr Leu Leu Asp Ser Arg Gly Trp Gly Thr Leu Leu
        35                  40                  45 tcc agg tct cga gct ggg cta gct gga gag att tcg ggt gtg aat tgg      192
Ser Arg Ser Arg Ala Gly Leu Ala Gly Glu Ile Ser Gly Val Asn Trp
    50                  55                  60 gaa agc ggc tat ttg gtg ggc att aag cga cag gct aat tac aag aag      240
Glu Ser Gly Tyr Leu Val Gly Ile Lys Arg Gln Ala Asn Tyr Lys Lys
65                  70                  75                  80 ccc aaa ctc ctc tac tgt agc aac ggg ggc cac ttc ctg agg atc ctt      288
Pro Lys Leu Leu Tyr Cys Ser Asn Gly Gly His Phe Leu Arg Ile Leu
                85                  90                  95 ccg gat ggc aca gtg gat ggg aca agg gac agg agc gac cag cac att      336
Pro Asp Gly Thr Val Asp Gly Thr Arg Asp Arg Ser Asp Gln His Ile
            100                 105                 110 cag ctg cag ctc agt gcg gaa agc gtg ggg gag gtg tat ata aag agt      384
Gln Leu Gln Leu Ser Ala Glu Ser Val Gly Glu Val Tyr Ile Lys Ser
        115                 120                 125 acc gag act ggc cag tac ttg gcc atg gac acc gac ggg ctt tta tac      432
Thr Glu Thr Gly Gln Tyr Leu Ala Met Asp Thr Asp Gly Leu Leu Tyr
    130                 135                 140 ggc tca cag aca cca aat gag gaa tgt ttg ttc ctg gaa agg ctg gag      480
Gly Ser Gln Thr Pro Asn Glu Glu Cys Leu Phe Leu Glu Arg Leu Glu
145                 150                 155                 160 gag aac cat tac aac acc tat ata tcc aag aag cat gca gag aag aat      528
Glu Asn His Tyr Asn Thr Tyr Ile Ser Lys Lys His Ala Glu Lys Asn
                165                 170                 175 tgg ttt gtt ggc ctc aag aag aat ggg agc tgc aaa cgc ggt cct cgg      576
Trp Phe Val Gly Leu Lys Lys Asn Gly Ser Cys Lys Arg Gly Pro Arg
            180                 185                 190
```

-continued

```
act cac tat ggc cag aaa gca atc ttg ttt ctc ccc ctg cca gtc tct    624
Thr His Tyr Gly Gln Lys Ala Ile Leu Phe Leu Pro Leu Pro Val Ser
        195                 200                 205 tct gat                                                            630
Ser Asp
    210
```

<210> SEQ ID NO 29
<211> LENGTH: 180
<212> TYPE: PRT
<213> ORGANISM: Artificial Sequence
<220> FEATURE:
<223> OTHER INFORMATION: Description of Artificial Sequence: fusion of
      sequence for a part of mouse fibroblast growth factor 6,
      a part of human fibroblast growth factor 1 and an artificial
      sequence

<400> SEQUENCE: 29

```
Met Ser Arg Gly Ala Gly Arg Val Gln Gly Thr Leu Gln Ala Leu Val
  1               5                  10                  15

Phe Leu Gly Val Leu Val Gly Met Val Val Pro Ser Pro Ala Gly Ala
             20                  25                  30

Arg Ala Asn Gly Thr Leu Leu Asp Ala Asn Tyr Lys Lys Pro Lys Leu
         35                  40                  45

Leu Tyr Cys Ser Asn Gly Gly His Phe Leu Arg Ile Leu Pro Asp Gly
     50                  55                  60

Thr Val Asp Gly Thr Arg Asp Arg Ser Asp Gln His Ile Gln Leu Gln
 65                  70                  75                  80

Leu Ser Ala Glu Ser Val Gly Glu Val Tyr Ile Lys Ser Thr Glu Thr
                 85                  90                  95

Gly Gln Tyr Leu Ala Met Asp Thr Asp Gly Leu Leu Tyr Gly Ser Gln
            100                 105                 110

Thr Pro Asn Glu Glu Cys Leu Phe Leu Glu Arg Leu Glu Glu Asn Ala
        115                 120                 125

Thr Pro Ala Pro His Tyr Asn Thr Tyr Ile Ser Lys Lys His Ala Glu
    130                 135                 140

Lys Asn Trp Phe Val Gly Leu Lys Lys Asn Gly Ser Cys Lys Arg Gly
145                 150                 155                 160

Pro Arg Thr His Tyr Gly Gln Lys Ala Ile Leu Phe Leu Pro Leu Pro
                165                 170                 175

Val Ser Ser Asp
            180
```

<210> SEQ ID NO 30
<211> LENGTH: 540
<212> TYPE: DNA
<213> ORGANISM: Artificial Sequence
<220> FEATURE:
<223> OTHER INFORMATION: Description of Artificial Sequence: fusion of
      sequence for a part of mouse fibroblast growth factor 6,
      a part of human fibroblast growth factor 1 and an artificial
      sequence
<221> NAME/KEY: CDS
<222> LOCATION: (1)..(540)

<400> SEQUENCE: 30

```
atg tcc cgg gga gca gga cgt gtt cag ggc acg ctg cag gct ctc gtc    48
Met Ser Arg Gly Ala Gly Arg Val Gln Gly Thr Leu Gln Ala Leu Val
  1               5                  10                  15 ttc tta ggc gtc cta gtg ggc atg gtg gtg ccc tca cct gcc ggc gcc    96
Phe Leu Gly Val Leu Val Gly Met Val Val Pro Ser Pro Ala Gly Ala
```

-continued

```
                    20                   25                    30 cgc gcc aac ggc acg cta ctg gac gct aat tac aag aag ccc aaa ctc      144
Arg Ala Asn Gly Thr Leu Leu Asp Ala Asn Tyr Lys Lys Pro Lys Leu
         35                       40                    45 ctc tac tgt agc aac ggg ggc cac ttc ctg agg atc ctt ccg gat ggc      192
Leu Tyr Cys Ser Asn Gly Gly His Phe Leu Arg Ile Leu Pro Asp Gly
     50                       55                    60 aca gtg gat ggg aca agg gac agg agc gac cag cac att cag ctg cag      240
Thr Val Asp Gly Thr Arg Asp Arg Ser Asp Gln His Ile Gln Leu Gln
 65                       70                    75                80 ctc agt gcg gaa agc gtg ggg gag gtg tat ata aag agt acc gag act      288
Leu Ser Ala Glu Ser Val Gly Glu Val Tyr Ile Lys Ser Thr Glu Thr
             85                       90                    95 ggc cag tac ttg gcc atg gac acc gac ggg ctt tta tac ggc tca cag      336
Gly Gln Tyr Leu Ala Met Asp Thr Asp Gly Leu Leu Tyr Gly Ser Gln
                100                      105                   110 aca cca aat gag gaa tgt ttg ttc ctg gaa agg ctg gag gag aac gct      384
Thr Pro Asn Glu Glu Cys Leu Phe Leu Glu Arg Leu Glu Glu Asn Ala
                    115                      120                  125 act cca gct cca cat tac aac acc tat ata tcc aag aag cat gca gag      432
Thr Pro Ala Pro His Tyr Asn Thr Tyr Ile Ser Lys Lys His Ala Glu
    130                      135                   140 aag aat tgg ttt gtt ggc ctc aag aag aat ggg agc tgc aaa cgc ggt      480
Lys Asn Trp Phe Val Gly Leu Lys Lys Asn Gly Ser Cys Lys Arg Gly
145                      150                   155                  160 cct cgg act cac tat ggc cag aaa gca atc ttg ttt ctc ccc ctg cca      528
Pro Arg Thr His Tyr Gly Gln Lys Ala Ile Leu Phe Leu Pro Leu Pro
                165                      170                   175 gtc tct tct gat                                                      540
Val Ser Ser Asp
            180
```

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:primer for PCR

<400> SEQUENCE: 31
aacaaaagct gggtaccggg                                                 20

What is claimed is:

1. A functionalized heparin-binding protein comprising a heparin-binding protein and at least one sugar chain covalently bonded thereto,
    said at least one covalently bonded sugar chain being selected from the group consisting of a sulfated polysaccharide, a glycosaminoglycan and an O-linked sugar chain,
    said heparin-binding protein comprising (a) a proteoglycan core protein or a part thereof, to which said sugar chain is bonded, and (b) the portion of the amino acid sequence of SEQ ID NO: 1 starting with Asn at number 88 and ending with Asp at number 221,
    wherein the DNA synthesis promoting activity of the heparin-binding protein is increased by adding the at least one covalently bonded sugar chain.

2. The functionalized heparin-binding protein of claim 1, wherein the at least one sugar chain is heparan sulfate.

3. The functionalized heparin-binding protein of claim 1, wherein the functionalized heparin-binding protein has improved stability over an unmodified heparin-binding protein.

4. The functionalized heparin-binding protein of claim 3, wherein the stability is chosen from among the group consisting of thermostability, acid resistance, alkalai resistance and resistance to proteolytic enzymes.

5. A pharmaceutical composition containing the functionalized heparin-binding protein of claim 1 as an active ingredient.

* * * * *